United States Patent
Sin et al.

(10) Patent No.: US 10,942,188 B2
(45) Date of Patent: Mar. 9, 2021

(54) METHODS AND SYSTEMS OF DETECTING PLASMA PROTEIN BIOMARKERS FOR DIAGNOSING ACUTE EXACERBATION OF COPD

(71) Applicant: THE UNIVERSITY OF BRITISH COLUMBIA, Vancouver (CA)

(72) Inventors: Don D. Sin, Vancouver (CA); Raymond T. Ng, Vancouver (CA); Bruce McManus, Delta (CA); Zsuzsanna Hollander, Vancouver (CA); Virginia Chen, Vancouver (CA)

(73) Assignee: The University of British Columbia, Vancouver (CA)

( * ) Notice: Subject to any disclaimer, the term of this patent is extended or adjusted under 35 U.S.C. 154(b) by 279 days.

(21) Appl. No.: 15/575,307

(22) PCT Filed: May 17, 2016

(86) PCT No.: PCT/IB2016/052872
§ 371 (c)(1),
(2) Date: Nov. 17, 2017

(87) PCT Pub. No.: WO2016/185385
PCT Pub. Date: Nov. 24, 2016

(65) Prior Publication Data
US 2019/0383830 A1    Dec. 19, 2019

Related U.S. Application Data

(60) Provisional application No. 62/235,390, filed on Sep. 30, 2015, provisional application No. 62/163,210, filed on May 18, 2015.

(51) Int. Cl.
*G01N 33/68* (2006.01)

(52) U.S. Cl.
CPC ... *G01N 33/6884* (2013.01); *G01N 2800/122* (2013.01)

(58) Field of Classification Search
None
See application file for complete search history.

(56) References Cited

U.S. PATENT DOCUMENTS

| | | | | |
|---|---|---|---|---|
| 2008/0026949 A1* | 1/2008 | Hoidal | .......... | C12Q 1/6883 506/6 |
| 2009/0324591 A1* | 12/2009 | Crump | .......... | C12N 15/1136 424/133.1 |
| 2011/0137131 A1* | 6/2011 | Adourian | .......... | G01N 33/6893 600/300 |
| 2013/0183684 A1* | 7/2013 | Gibson | .......... | G01N 33/6893 435/7.4 |

FOREIGN PATENT DOCUMENTS

| | | | | |
|---|---|---|---|---|
| CN | 102253220 | 11/2011 | | |
| EP | 2637023 | 9/2013 | | |
| EP | 2637023 A1 * | 9/2013 | ......... | G01N 33/6884 |
| KR | 101458821 | 11/2014 | | |
| WO | 2016185385 | 11/2016 | | |

OTHER PUBLICATIONS

Cornwell et al., Alternatively Activated Macrophage (M2) Marker, 2010, D13 Virus Host Interactions in Asthma and Chronic Obstructive Pulmonary Disease, 1-3 (Year: 2010).*
York et al., High-resolution mass spectrometry proteomics for the identification of candidate plasma protein biomarkers for chronic obstructive pulmonary disease, Biomarkers, 2010; 15(4): 367-377 (Year: 2010).*
De Jong et al., Oral or IV Prednisolone in the Treatment of COPD Exacerbations, Chest 2007;132;1741-1747. (Year: 2007).*
Chen et al., "Selection of disease-specific biomarkers by integrating inflammatory mediators with clinical informatics in AECOPD patients: a preliminary study", J Cell Mol Med, vol. 16, No. 6, Jun. 2012, pp. 1286-1297.
Husebø et al., "Predictors of exacerbations in chronic obstructive pulmonary disease—results from the Bergen COPD cohort study", PLOS One, vol. 9, No. 10, 2014, p. e109721.
Jin et al., "Low Serum retinol-binding protein-4 levels in acute exacerbations of chronic obstructive pulmonary disease at intensive care unit admission is a predictor of mortality in elderly patients", Journal of Inflammation, vol. 10, No. 1, 2013.
PCT/IB2016/052872 , "International Search Report and Written Opinion", dated Jul. 25, 2016, 11 pages.
PCT/IB2016/052872 , "Invitation to Pay Add'l Fees and Partial Search Report", dated Jun. 2, 2016, 2 pages.
Shaw et al., "Biomarkers of progression of chronic obstructive pulmonary disease (COPD)", J Thorac Dis, vol. 6, No. 11, 2014, pp. 1532-1547.

* cited by examiner

*Primary Examiner* — Andrea S Grossman
(74) *Attorney, Agent, or Firm* — Kilpatrick Townsend & Stockton LLP

(57) ABSTRACT

Described are compositions and methods for diagnosing acute exacerbations of chronic obstructive pulmonary disease (AECOPD). Multiple reaction monitoring mass spectrometry (MRM-MS) was used to quantify the amount of protein biomarkers in plasma samples from human subjects. The amount of the biomarkers in the sample can distinguish AECOPD from a stable or convalescent state of COPD, or from a subject without COPD.

6 Claims, 12 Drawing Sheets
Specification includes a Sequence Listing.

METHODS AND SYSTEMS OF DETECTING PLASMA PROTEIN BIOMARKERS FOR DIAGNOSING ACUTE EXACERBATION OF COPD

CROSS-REFERENCE

This application is a U.S. National Stage entry of PCT/IB2016/052872, filed May 17, 2016, titled "METHODS AND SYSTEMS OF DETECTING PLASMA PROTEIN BIOMARKERS FOR DIAGNOSING ACUTE EXACERBATION OF COPD", which claims priority to U.S. Provisional Application No. 62/163,210, filed May 18, 2015, titled "METHODS AND SYSTEMS OF DETECTING PLASMA PROTEIN BIOMARKERS FOR DIAGNOSING ACUTE EXACERBATION OF COPD" and U.S. Provisional Application No. 62/235,390, filed Sep. 30, 2015, titled "METHODS AND SYSTEMS OF DETECTING PLASMA PROTEIN BIOMARKERS FOR DIAGNOSING ACUTE EXACERBATION OF COPD", the entire disclosures of each of which are incorporated by reference herein.

SEQUENCE LISTING

The instant application contains a Sequence Listing which has been submitted electronically in ASCII format and is hereby incorporated by reference in its entirety. Said ASCII copy, created on May 17, 2016, is named 97513-1008745-000310PC_SL.txt and is 153,175 bytes in size.

BACKGROUND OF THE INVENTION

In patients with chronic obstructive pulmonary disease (COPD), fixed airflow limitation often results in symptoms such as dyspnea, cough, and sputum production. The periodic worsening of these symptoms are known as acute exacerbations (AECOPD), events that can have lasting detrimental effects on lung function (1), respiratory-related quality of life (2), and mortality (3). Economically, the impact of AECOPD is profound as annual AECOPD-related costs in the United States alone amount to $30 billion (4). The diagnosis of an AECOPD, largely made on the basis of clinical gestalt, is fraught with imprecision (5). In recent years, the search for a blood-based biomarker to distinguish AECOPD from states of relative clinical stability has focused on common inflammatory markers such as plasma C-reactive protein (CRP) (6) and serum amyloid protein (7). Such a restrictive strategy, however, overlooks the fundamental heterogeneity of AECOPD in which respiratory viruses, bacterial infection, air pollution; and cardiac dysfunction can all conspire in distinct pathways to incite an event (8-11).

A comprehensive approach to biomarkers could potentially revolutionize the diagnosis and management of AECOPD, ideally revealing a panel of biomarkers that could accurately identify AECOPD early in the clinical course. Shotgun proteomics, requiring no a priori hypothesis, offers an unbiased platform to detect biomarker candidates, yet is limited by low-throughput efficiency, poor accuracy and suboptimal quantitation. Multiple reaction monitoring-mass spectrometry (MRM-MS) offers an inexpensive, high-throughput platform with the ability to quantify hundreds of targeted proteins based on precursor-product ion pairs (12) and in 2012 was selected by Nature as "Method of the Year" (13). MRM-MS has since been employed to verify and validate biomarker panels in lung cancer amongst many other diseases (14). As described herein, the instant inventors used MRM-MS to identify new clinically applicable biomarkers for AECOPD.

BRIEF SUMMARY OF THE INVENTION

The present disclosure provides compositions and methods for diagnosing, providing a prognosis, or determining if a subject is at risk for AECOPD. Surprisingly, a panel or combination of biomarkers was found to reliably distinguish subjects with AECOPD from subjects in a stable or convalescent state of COPD, or from subjects without COPD.

In a first aspect, a method for diagnosing AECOPD in a subject is described, the method comprising: obtaining a dataset associated with a sample obtained from a subject, wherein the dataset comprises at least one, two, three, four, or five or more markers selected from Table 2, Table 3, Table 4, Table 6, Table 7, or Table 10; and analyzing the dataset to determine data for the markers, wherein the data is positively correlated or negatively correlated with AECOPD in the subject. The dataset can also comprise one or more combinations of markers from Table 2, Table 3, Table 4, Table 6, Table 7, or Table 10. In some embodiments, the dataset comprises a plurality of markers selected from Table 2, Table 3, Table 4, Table 6, Table 7, or Table 10.

In some embodiments, the dataset comprises data for at least two, three, four, five, six, seven, eight, nine, ten, eleven, twelve, thirteen, fourteen, fifteen, sixteen, seventeen, eighteen or more markers selected from Table 2. In some embodiments, the method further comprises analyzing the dataset to determine the expression level or abundance of the at least two, three, four, five, six, seven, eight, nine, ten, eleven, twelve, thirteen, fourteen, fifteen, sixteen, seventeen, eighteen or more markers selected from Table 2.

In some embodiments of the methods described herein, the dataset comprises or consists of the peptide markers in Table 4. In some embodiments of the methods described herein, the dataset comprises or consists of the protein markers in Table 4, or peptide fragments thereof. In some embodiments of the methods described herein, the dataset comprises or consists of the peptide markers in Table 6. In some embodiments of the methods described herein, the dataset comprises or consists of the protein markers in Table 3, or a peptide fragment thereof. In some embodiments of the methods described herein, the dataset comprises or consists of the protein markers in Table 7, or a peptide fragment thereof. In some embodiments of the methods described herein, the dataset comprises or consists of the markers in Table 10, or a peptide fragment thereof.

In some embodiments, the method further comprises determining AECOPD in the subject according to the relative number of positively correlated and negatively correlated marker expression level or marker abundance data present in the dataset. In some embodiments, the expression level or abundance of a marker is positively correlated with AECOPD if the expression level or abundance of the marker increases in patients with AECOPD. In some embodiments, the expression level or abundance of a marker is negatively correlated with AECOPD if the expression level or abundance of the marker decreases in patients with AECOPD.

In some embodiments, the expression level or abundance of a marker is increased (e.g. upregulated) or decreased (e.g. downregulated) relative to the same marker in a control sample. For example, in some embodiments, the expression level or abundance of a protein, or peptide fragment thereof, is increased or decreased relative to the same marker in a control sample. In some embodiments, the expression level or abundance of a protein, or peptide fragment thereof, from Table 2, Table 3, Table 4, Table 6, Table 7, or Table 10 is increased or decreased relative to the same marker in a control sample. In some embodiments, the expression level or abundance of a peptide selected from the group consisting of SEQ ID NOs: 1-9, 12, 14, 16-18 and 21 is decreased or down regulated relative to a control sample (e.g., a sample from a subject without AECOPD). In some embodiments, the expression level or abundance of a peptide selected from the group consisting of SEQ ID NOs: 11, 13, and 15 is increased or upregulated relative to a control sample (e.g., a sample from a subject without AECOPD). In some embodiments, the marker comprises a peptide fragment of a protein selected from the group consisting of SEQ ID NOs: 22-42. In some embodiments, the marker comprises or consists of a set of peptide fragments from a protein selected from the group consisting of SEQ ID NOs: 22-42. In some embodiments, marker comprises or consists of a set or combination of peptides comprising peptide fragments from a protein selected from Table 3. In one embodiment, the set or combination of peptides comprises a peptide fragment from a protein selected from SEQ ID NOs: 22-30, 32-39, and 42. In one embodiment, the marker comprises or consists of a set or combination of peptides selected from SEQ ID NOs: 1-21, or SEQ ID NOs: 1-9, 11-18, and 21. In some embodiments, the expression level or abundance of a peptide selected from the group consisting of SEQ ID NOs: 1-9, 12, 14, 16-18 and 21 is decreased or down regulated relative to a control sample, and the expression level or abundance of a peptide selected from the group consisting of SEQ ID NOs: 11, 13, and 15 is increased or upregulated relative to a control sample (e.g., a sample from a subject without AECOPD).

In some embodiments, a biomarker score is calculated based on the weighted contributions of the marker proteins shown in Table 3, or peptide fragments thereof in some embodiments, the biomarker score is significantly greater in a subject with AECOPD than in a control subject without AECOPD.

In some embodiments, a biomarker score is calculated based on the weighted contributions of the marker proteins shown in Table 7, or peptide fragments thereof. In some embodiments, the biomarker score is significantly greater in a subject with AECOPD than in a control subject without AECOPD.

In some embodiments, a biomarker score is calculated based on the weighted contributions of the marker proteins shown in Table 10, or peptide fragments thereof. In some embodiments, the biomarker score is significantly greater in a subject with AECOPD than in a control subject without AECOPD.

In some embodiments, the control sample is from a subject without AECOPD. In some embodiments, the subject without AECOPD is a subject in the stable or convalescent state of COPD, or a subject without COPD. In some embodiments, the sample obtained from the subject is a blood sample, e.g., a plasma sample or a serum sample.

In some embodiments, the data in the dataset comprises protein expression or protein abundance data. In some embodiments, the protein abundance data is obtained using mass spectrometry. In one embodiment, the data is obtained using multiple reaction monitoring-mass spectrometry (MRM-MS). In some embodiments, the data is obtained using an antibody-based assay, such as an ELISA.

In some embodiments, the method is implemented using one or more computers.

In some embodiments, the method further comprises obtaining the sample from the subject.

In some embodiments, the above methods further comprise providing a course of treatment based on the diagnosis.

In a second aspect, a method for determining the risk of acute exacerbations of chronic obstructive pulmonary disease (AECOPD) is described, the method comprising:
measuring the expression level or abundance of at least one marker in Table 2, Table 3, Table 4, Table 6, Table 7, or Table 10 in a sample obtained from a subject;
comparing the expression level or abundance with the expression level or abundance of the at least one marker in Table 2 in a control sample; and
determining if the subject has a risk of AECOPD if the expression level or abundance of the at least one marker in the sample from the subject is statistically different from the expression level in the control sample.

In some embodiments, the control sample is obtained from a subject in the stable or convalescent state of COPD, or a subject without COPD.

In some embodiments of the aspects described herein, the at least one marker from Table 2 comprises:
(i) a peptide selected from SEQ ID NOs: 1-21, or
(ii) a protein selected from the group consisting of Apolipoprotein C-II (SEQ ID NO: 22), Afamin (SEQ ID NO: 23), Apolipoprotein A-I (SEQ ID NO: 24), Retinol-binding protein 4 (SEQ ID NO: 25), Apolipoprotein A-II (SEQ ID NO: 26), Beta-2-glycoprotein 1 (SEQ ID NO: 27), Protein AMBP (SEQ ID NO: 28), Pigment epithelium-derived factor (SEQ ID NO: 29), Transthyretin (SEQ ID NO: 30), Plasma serine protease inhibitor (SEQ ID NO: 31), Complement component C6 (SEQ ID NO: 32), Heparin cofactor 2 (SEQ ID NO: 33), Complement component C9 (SEQ ID NO: 34), Inter-alpha-trypsin inhibitor heavy chain H2 (SEQ ID NO: 35), C-reactive protein (SEQ ID NO: 36), Histidine-rich glycoprotein (SEQ ID NO: 37), Beta-2-microglobulin (SEQ ID NO: 38), Gelsolin (SEQ ID NO: 39), Plasma kallikrein (SEQ ID NO: 40), Insulin-like growth factor-binding protein 3 (SEQ ID NO: 41), and Hemopexin (SEQ ID NO: 42), or a peptide fragment thereof.

In some embodiments, the at least one marker from Table 2 comprises:
(i) a peptide selected from SEQ ID NOs: 1-9, 11-18, and 21, or
(ii) a protein selected from the group consisting of SEQ ID NOs: 2-30, 32-39, and 42, or a peptide fragment thereof.

In some embodiments, the at least one marker from Table 6 comprises:
(i) a peptide selected from SEQ ID NOs: 69, 13, 160, 1, 15, 9, and/or 191; or
(ii) a protein selected from the group consisting of Apolipoprotein A-IV (SEQ ID NO: 275), Apolipoprotein C-II (SEQ ID NO: 22), Complement component C9 (SEQ ID NO: 34), Fibronectin (FN1; SEQ ID NO: 276), C-reactive protein (CRP; SEQ ID NO: 273), Transthyretin (TTR; SEQ ID NO: 30), and Lipopolysaccharide-binding protein (LBP; SEQ ID NO: 277), or a peptide fragment thereof.

In some embodiments, the markers comprise C-reactive protein (CRP; SEQ ID NO: 273) and NT-proBNP (SEQ ID NO: 274), or peptide fragments thereof.

In a third aspect, a method for determining if a subject suffers from acute exacerbations of chronic obstructive pulmonary disease (AECOPD) is described, the method comprising:
  contacting a sample obtained from the subject with a reagent;
  generating a complex between the reagent and the markers;
  detecting the complex to obtain a dataset associated with the sample, wherein the dataset comprises expression level data for at least one marker selected from Table 2, Table 3, Table 4, Table 6, Table 7, or Table 10; and
  analyzing the expression level data for the markers, wherein the expression level of the markers is positively correlated or negatively correlated with AECOPD in the subject.

In a fourth aspect, a computer-implemented method is described, the method comprising:
  storing, in a storage memory, a dataset associated with a sample obtained from the subject, wherein the dataset comprises data for at least one marker selected from Table 2, Table 3, Table 4, Table 6, Table 7, or Table 10; and
  analyzing, by a computer processor, the dataset to determine the expression levels of the markers, wherein the expression levels are positively correlated or negatively correlated with AECOPD in the subject.

In a fifth aspect, a system is described, the system comprising:
  a storage memory for storing a dataset associated with a sample obtained from the subject, wherein the dataset comprises data for at least one marker selected from Table 2, Table 3, Table 4, Table 6, Table 7, or Table 10; and
  a processor communicatively coupled to the storage memory for analyzing the dataset to determine the expression levels of the markers, wherein the expression levels are positively correlated or negatively correlated with AECOPD in the subject.

In a sixth aspect, a computer-readable storage medium storing computer-executable program code is described, the program code comprising:
  program code for storing a dataset associated with a sample obtained from a subject, wherein the dataset comprises data for at least one marker selected from Table 2, Table 3, Table 4, Table 6, Table 7, or Table 10; and
  program code for analyzing the dataset to determine the expression levels of the markers, wherein the expression levels of the markers are positively correlated or negatively correlated with AECOPD in the subject.

In a seventh aspect, a kit for detecting AECOPD is provided, the kit comprising:
  (i) a plurality of reagents for determining data for at least one marker selected from Table 2, Table 3, Table 4, Table 6, Table 7, or Table 10 in a sample obtained from a subject;
  (ii) a positive control sample; and instructions for using the plurality of reagents to determine data from the sample.

In some embodiments, the plurality of reagents comprise antibodies that specifically bind a protein or peptide listed in Table 2, Table 3, Table 4, Table 6, Table 7, or Table 10; or a peptide fragment of a protein listed in Table 2, Table 3, Table 4, Table 6, Table 7, or Table 10. In some embodiments, the plurality of reagents comprise reagents for performing a mass spectrometry assay. In some embodiments, the instructions comprise instructions for conducting a protein-based assay or a mass spectrometry assay. In some embodiments, the kit provides a diagnostic accuracy having a sensitivity of at least 90% and/or a specificity of at least 86%.

In an eighth aspect, a method for determining if a subject suffers from acute exacerbations of chronic obstructive pulmonary disease (AECOPD) is described, the method comprising:
  measuring the expression level or abundance of at least one marker selected from Table 2, Table 3, Table 4, Table 6, Table 7, or Table 10 in a first sample obtained from the subject;
  comparing the expression level or abundance with the expression level or abundance of the at least one marker selected from Table 2, Table 3, Table 4, Table 6, Table 7, or Table 10 in a second sample obtained from the subject in a stable or convalescent state; and
  determining that the subject suffers from AECOPD if the expression level or abundance in the first sample is statistically different from the expression level or abundance in the second sample.

In some embodiments, measuring the expression level or abundance of at least one marker selected from Table 2 or Table 3 comprises measuring the expression level or abundance of a peptide selected from SEQ ID NOs: 1-21, or a peptide fragment of a protein selected from SEQ ID NOs: 22-42, in a first sample obtained from the subject;
  comparing the expression level or abundance with the expression level or abundance of the peptide selected from SEQ ID NOs: 1-21, or a peptide fragment of a protein selected from SEQ ID NOs: 22-42, in a second sample obtained from the subject in a stable or convalescent state; and
  determining that the subject suffers from AECOPD if the expression level or abundance in the first sample is statistically different from the expression level or abundance in the second sample.

In some embodiments, measuring the expression level or abundance of at least one marker selected from Table 6 or Table 7 comprises measuring the expression level or abundance of
  (i) a peptide selected from SEQ ill NOs: 1, 13, 69, 160, and/or 191; or
  (ii) a protein selected from the group consisting of Apolipoprotein C-II (SEQ ID NO: 22), Complement component C9 (SEQ ID NO: 34), Apolipoprotein A-IV (SEQ ID NO: 275), Fibronectin (SEQ ID NO: 276), and Lipopolysaccharide Binding Protein (SEQ ID NO: 277), or a peptide fragment thereof.

In some embodiments, measuring the expression level or abundance of at least one marker selected from Table 10 comprises measuring C-reactive protein (SEQ ID NO: 273) and NT-proBNP (SEQ ID NO: 274), or peptide fragments thereof.

In a ninth aspect, a method for determining if a subject suffers from acute exacerbations of chronic obstructive pulmonary disease (AECOPD) is described, the method comprising:
  obtaining a first dataset associated with a first sample obtained from a subject suspected of suffering from AECOPD, wherein the first dataset comprises at least one marker selected from Table 2, Table 3, Table 4, Table 6, Table 7, or Table 10;
  obtaining a second dataset associated with a second sample obtained from the subject during a convalescent state, wherein the second dataset comprises at least one marker selected from Table 2, Table 3, Table 4, Table 6, Table 7, or Table 10;

analyzing the first and second datasets to determine data for the markers, wherein the data is positively correlated or negatively correlated with AECOPD in the subject.

In some embodiments, the first dataset comprises data for at least two, three, four, five, six, seven, eight, nine, ten, eleven, twelve, thirteen, fourteen, fifteen, sixteen, seventeen, eighteen or more markers selected from Table 2, and the second dataset comprises data for at least two, three, four, five, six, seven, eight, nine, ten, eleven, twelve, thirteen, fourteen, fifteen, sixteen, seventeen, eighteen or more markers selected from Table 2. In some embodiments, the method further comprises analyzing the first and second datasets to determine the expression level of the at least two, three, four, five, six, seven, eight, nine, ten, eleven, twelve, thirteen, fourteen, fifteen, sixteen, seventeen, eighteen or more markers selected from Table 2.

In some embodiments, the first and second datasets comprise data for at least one marker selected from Table 4. In one embodiment, the method further comprises analyzing the first and second datasets to determine the expression level or abundance of the at least one marker from Table 4.

In some embodiments, the first and second datasets comprise data for at least two, three, four, or five markers selected from Table 6 or Table 7. In one embodiment, the method further comprises analyzing the first and second datasets to determine the expression level or abundance of the at least two, three, four, or five markers selected from Table 6 or 7.

In some embodiments, the at least two, three, four, or five markers from Table 6 or Table 7 comprises:
 (i) a peptide selected from SEQ ID NOs: 1, 13, 69, 160, and/or 191; or
 (ii) a protein selected from the group consisting of Apolipoprotein C-II (SEQ ID NO: 22), Complement component C9 (SEQ ID NO: 34), Apolipoprotein A-IV (SEQ ID NO: 275), Fibronectin (SEQ ID NO: 276), and Lipopolysaccharide Binding Protein (SEQ ID NO: 277), or a peptide fragment thereof.

In some embodiments, the first and second datasets comprise data for at least one marker selected from Table 3 or Table 10, or a peptide fragment thereof. In one embodiment, the method further comprises analyzing the first and second datasets to determine the expression level or abundance of the at least one marker selected from Table 3 or 10.

In some embodiments, the method further comprises determining if the subject suffers from AECOPD according to the relative number of positively correlated and negatively correlated marker expression level data present in the first and second datasets. In some embodiments, the method provides a sensitivity of at least 90% and/or a specificity of at least 86% for determining if the subject suffers from AECOPD.

In another aspect, a composition for use in diagnosing AECOPD is described, the composition comprising:
 (i) a reagent for detecting at least one peptide or protein in Table 2, Table 3, Table 4, Table 6, Table 7, or Table 10; or
 (ii) a reagent for detecting a peptide fragment of a protein in Table 2, Table 3, Table 4, Table 6, Table 7, or Table 10.
In some embodiments, the reagent is an antibody or an ion.

In another aspect, a composition for use in diagnosing AECOPD is described, the composition comprising at least one peptide or protein selected from Table 2, Table 3, Table 4, Table 6, Table 7, or Table 10; or
 a peptide fragment of a protein selected from Table 2, Table 3, Table 4, Table 6, Table 7, or Table 10.

In some embodiments, the composition for use in diagnosing AECOPD comprises:
 (i) a set of peptides selected from SEQ ID NOs 1-21;
 (ii) a peptide fragment of a protein selected from SEQ ID NOs: 22-42;
 (iii) a peptide selected from SEQ ID NOs: 1, 13, 69, 160, or 191;
 (iv) a protein selected from the group consisting of Apolipoprotein C-II (SEQ ID NO: 22), Complement component C9 (SEQ ID NO: 34), Apolipoprotein A-IV, (SEQ ID NO: 275), Fibronectin (SEQ ID NO: 276), and Lipopolysaccharide Binding Protein (SEQ ID NO: 277), or a peptide fragment thereof; or
 (v) a protein selected from CRP (SEQ ID NO: 273) or NT-proBNP (SEQ ID NO: 274), or a peptide fragment thereof.

In some embodiments, composition comprises (i) a set of peptides consisting of SEQ ID NOs 1-9, 11-18, and 21, or
 (ii) a peptide fragment of a protein selected from SEQ ID NOs: 22-30, or 32-39.

In any of the aspects described herein, the at least one marker from Table 2 can comprise:
 (i) a peptide selected from SEQ ID NOs: 1-21, or
 (ii) a protein selected from the group consisting of Apolipoprotein C-II (SEQ ID NO: 22), Afamin (SEQ ID NO: 23), Apolipoprotein A-I (SEQ ID NO: 24), Retinol-binding protein 4 (SEQ ID NO: 25), Apolipoprotein A-II (SEQ ID NO: 26), Beta-2-glycoprotein 1 (SEQ ID NO: 27), Protein AMBP (SEQ ID NO: 28), Pigment epithelium-derived factor (SEQ ID NO: 29), Transthyretin (SEQ ID NO: 30), Plasma serine protease inhibitor (SEQ ID NO: 31), Complement component C6 (SEQ ID NO: 32), Heparin cofactor 2 (SEQ ID NO: 33), Complement component C9 (SEQ ID NO: 34), Inter-alpha-trypsin inhibitor heavy chain 112 (SEQ ID NO: 35), C-reactive protein (SEQ ID NO: 36), Histidine-rich glycoprotein (SEQ ID NO: 37), Beta-2-microglobulin (SEQ ID NO: 38), Gelsolin (SEQ ID NO: 39), Plasma kallikrein (SEQ ID NO: 40), insulin-like growth factor-binding protein 3 (SEQ ID NO: 41), and Hemopexin (SEQ ID NO: 42), or a peptide fragment thereof.

In some embodiments, the at least one marker from Table 2 comprises:
 (i) a peptide selected from SEQ ID NOs: 1-9, 11-18, and 21, or
 (ii) a protein selected from the group consisting of SEQ ID NOs: 22-30, 32-39, and 42, or a peptide fragment thereof.

In any of the aspects described herein, the at least one marker from Table 6 can comprise:
 (i) a peptide selected from SEQ ID NOs: 69, 13, 160, 1, 15, 9, and/or 191; or
 (ii) a protein selected from the group consisting of Apolipoprotein A-IV (SEQ ID NO: 275), Apolipoprotein C-II (SEQ ID NO: 22), Complement component C9 (SEQ ID NO: 34), Fibronectin (FN1; SEQ ID NO: 276), C-reactive protein (CRP; SEQ ID NO: 273), Transthyretin (TTR; SEQ ID NO: 30), and Lipopolysaccharide-binding protein (LBP; SEQ ID NO: 277), or a peptide fragment thereof.

In some embodiments, the at least one marker from Table 6 comprises:
- (i) a peptide selected from SEQ ID NOs: 69, 13, 160, 1, and/or 191; or
- (ii) a protein selected from the group consisting of Apolipoprotein A-IV (SEQ ID NO: 275), Apolipoprotein C-II (SEQ ID NO: 22), Complement component C9 (SEQ ID NO: 34), Fibronectin (FN1; SEQ ID NO: 276), and Lipopolysaccharide-binding protein (LBP; SEQ ID NO: 277), or a peptide fragment thereof.

In another aspect, a method of detecting a biomarker in a biological sample is described. In some embodiments, the method comprises measuring the abundance of a peptide comprising any one of SEQ ID NOs: 1-21, or a peptide fragment of SEQ ID NOs: 22-42, or 273-277 in the sample. In some embodiments, the method comprises measuring the abundance of a protein comprising SEQ ID NOs: 275, 22, 34, 276, 273, 30, and/or 277, or a peptide fragment thereof. In some embodiments, the method comprises measuring the abundance of a protein comprising SEQ ID NOs: 273 and 274, or a peptide fragment thereof. In some embodiments, the abundance of the peptide is measured using MRM-MS. For example, in some embodiments, the biological sample is blood, serum, or plasma, and the proteins in the sample are digested with trypsin to produce peptide fragments that are detected using mass spectrometry as described in the Examples. In some embodiments, the abundance of at least 18 peptides selected from the group consisting of SEQ ID NOs: 1-9, 11-18, and 21, is measured. In some embodiments, a set of peptides selected from Table 2 is measured. In some embodiments, the set of peptides comprises or consists of at least 18 peptides from Table 2. In some embodiments, the set of peptides comprises or consists of SEQ ID NOs: 1-9, 11-18, and 21. In some embodiments, the set of peptides comprises or consists of a peptide fragment selected from SEQ ID NOs: 22-30, 32-39, and 42. In some embodiments, a set of peptides selected from Table 4 is measured. In some embodiments, a set of peptides selected from Table 6 is measured. In some embodiments, the set of peptides from Table 6 comprises or consists of SEQ ID NOs: 69, 13, 160, 1, 15, 9, and/or 191. In some embodiments, the set of peptides from Table 6 comprises or consists of SEQ ID NOs: 69, 13, 160, 1, and/or 191. In some embodiments, the expression level or abundance of a peptide selected from the group consisting of SEQ ID NOs: 69, 160, 1 and 9 is decreased or down regulated relative to a control sample, and the expression level or abundance of a peptide selected from the group consisting of SEQ ID NOs: 13, 15, and 191 is increased or upregulated relative to a control sample (e.g., a sample from a subject without AECOPD). In some embodiments, a set of proteins selected from Tables 3, 7, or 10, or a peptide fragment thereof, is measured.

In some embodiments of the method for detecting a biomarker in a biological sample, the biomarker is selected from:
- (i) a set of peptides selected from SEQ ID NOs 1-21;
- (ii) a peptide fragment of a protein selected from SEQ ID NOs: 22-42;
- (iii) a peptide selected from SEQ ID NOs: 1, 13, 69, 160, or 191;
- (iv) a peptide fragment of a protein selected from the group consisting of Apolipoprotein C-II (SEQ ID NO: 22), Complement component C9 (SEQ ID NO: 34), Apolipoprotein A-IV, (SEQ ID NO: 275), Fibronectin (SEQ ID NO: 276), and Lipopolysaccharide Binding Protein (SEQ ID NO: 277); or
- (v) a peptide fragment of a protein selected from CRP (SEQ ID NO: 273) or NT-proBNP (SEQ ID NO: 274).

In another aspect, method for determining if a subject suffers from AECOPD is described, the method comprising:
- measuring the expression level or abundance of a peptide selected from SEQ ID NOs: 1-21, or a peptide fragment of a protein selected from SEQ ID NOs: 22-42, or 273-277 in a first sample obtained from the subject;
- comparing the expression level or abundance with the expression level or abundance of the peptide selected from SEQ ID NOs: 1-21, or a peptide fragment of a protein selected from SEQ ID NOs: 22-42 or 273-277, in a second sample obtained from the subject in a stable or convalescent state; and
- determining that the subject suffers from AECOPD if the expression level or abundance in the first sample is statistically different from the expression level or abundance in the second sample.

In another embodiment, a method for diagnosing acute exacerbations of chronic obstructive pulmonary disease (AECOPD) in a subject is described, the method comprising:
- obtaining a dataset associated with a sample obtained from a subject, wherein the dataset comprises a marker selected from CRP (SEQ ID NO: 273) and NT-proBNP (SEQ ID NO: 274), or a peptide fragment thereof; and
- analyzing the dataset to determine data for the markers, wherein the data is positively correlated or negatively correlated with AECOPD in the subject.

In some embodiments, the markers CRP (SEQ ID NO: 273) and NTproBNP (SEQ ID NO: 274), or a peptide fragment thereof, are upregulated.

In the embodiments described herein, at least one, two, three, four, or five or more markers selected from Table 2, Table 3, Table 4, Table 6, Table 7, or Table 10 can be measured and analyzed and included in the dataset. In some embodiments, the biomarker panel or dataset comprises or consists of all or a subset of the markers in Table 2, Table 3, Table 4, Table 6, Table 7, or Table 10. The biomarker panel or dataset can also comprise one or more combinations of markers from Table 2, Table 3, Table 4, Table 6, Table 7, or Table 10.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

DEFINITIONS

Figure 1:
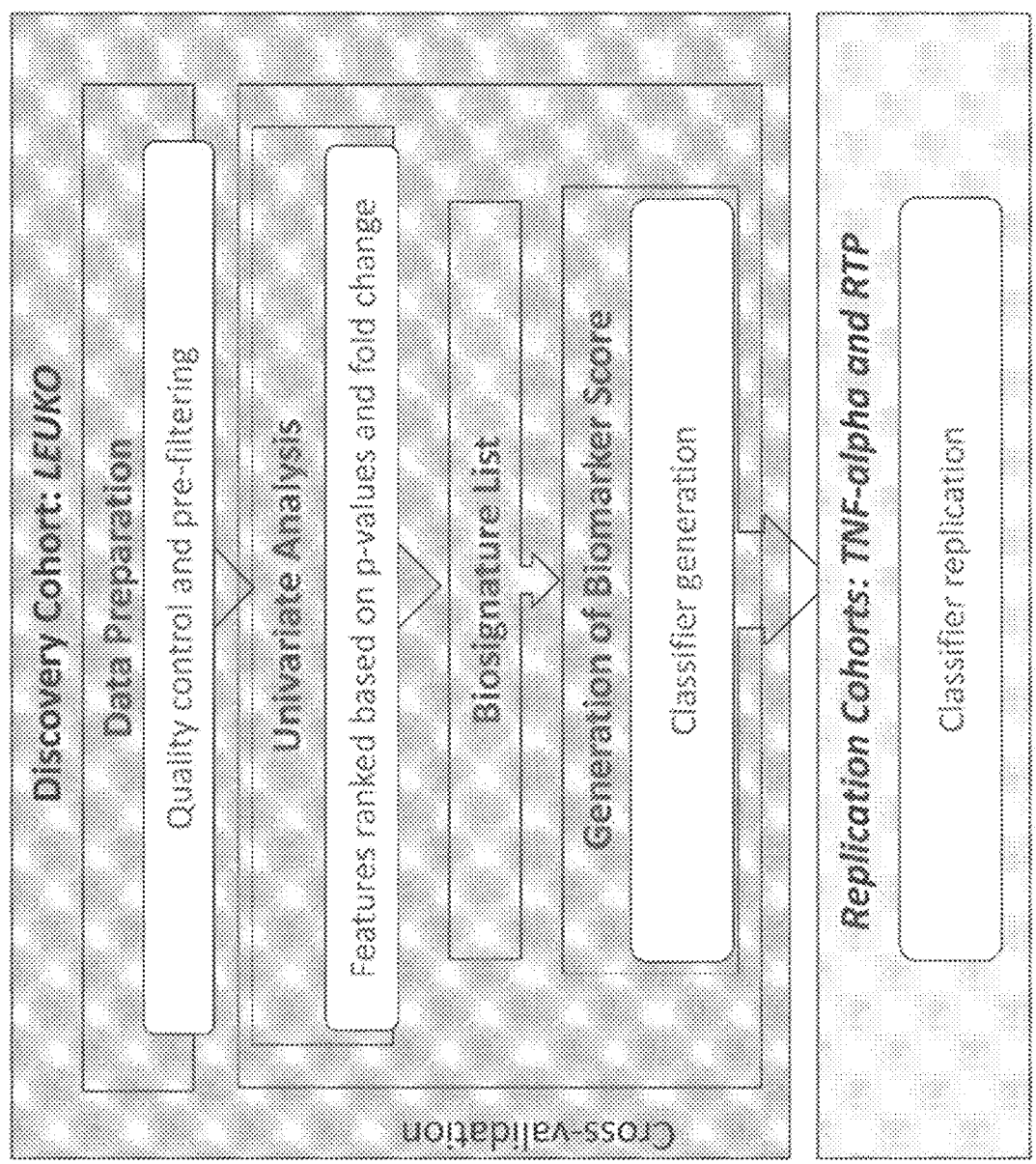
FIG. 1. Biomarker Discovery and Replication Strategy. Biomarker discovery steps, applied to the LEUKO cohort, are outlined in the blue box. After pre-processing, univariate analysis identifies candidate proteins based on statistically significant fold change at a false discovery rate <0.2. An elastic net model is applied to these candidate proteins with a final classifier model generated. This is subsequently followed by replication in the TNF-α and RTP cohorts (yellow box).

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control.

As used in the specification and the appended claims, the singular forms "a," "an," and "the" include plural referents unless the context clearly dictates otherwise.

Terms used in the claims and specification are defined as set forth below unless otherwise specified.

"Marker," "markers," "biomarker," or "biomarkers," refers generally to a molecule (e.g. a peptide, protein, carbohydrate, or lipid) that is expressed in a cell or tissue, which is useful for the prediction or diagnosis of AECOPD. A marker in the context of the present disclosure encompasses, for example, cytokines, chemokines, growth factors, proteins, peptides, and metabolites, together with their related metabolites, mutations, variants, modifications, fragments, subunits, degradation products, elements, and other analytes or sample-derived measures. Markers also encompass non-blood borne factors and non analyte physiological markers of health status, and/or other factors or markers not measured from samples (e.g., biological samples such as bodily fluids), such as clinical parameters and traditional factors for clinical assessments. Markers can also include any indices that are calculated and/or created mathematically.

Markers can also include combinations of any one or more of the foregoing measurements, including temporal trends and differences.

To "analyze" includes measurement and/or detection of data associated with a marker (such as, e.g., presence or absence of a peptide or protein, or constituent expression or abundance levels) in the sample (or, e.g., by obtaining a dataset reporting such measurements, as described below). In some aspects, an analysis can include comparing the measurement and/or detection of at least one marker in samples from a subject pre- and post-treatment or other control subject(s). The markers of the present teachings can be analyzed by any of various conventional methods known in the art.

A "subject" in the context of the present teachings is generally a mammal. The subject is generally a patient. The term "mammal" as used herein includes but is not limited to a human, non-human primate, dog, cat, mouse, rat, cow, horse, and pig. Mammals other than humans can be advantageously used as subjects that represent animal models of AECOPD. A subject can be male or female.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

In particular aspects, the sample s a blood sample from the subject.

A "dataset" is a set of data (e.g., numerical values) resulting from evaluation of a sample. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" encompasses obtaining a set of data determined from at least one sample.

In some embodiments, obtaining a dataset encompasses obtaining a sample, and processing the sample to experimentally determine the data, e.g., via measuring, microarray, one or more probes, antibody binding, ELISA, or mass spectometry. The phrase also encompasses receiving a set of data, e.g., from a third party that has processed the sample to experimentally determine the dataset. Additionally, the phrase encompasses mining data from at least one database or at least one publication or a combination of databases and publications.

"Measuring" or "measurement" in the context of the present teachings refers to determining the presence, absence, quantity, amount, or effective amount of a marker or other substance (e.g., peptide or protein) in a clinical or subject-derived sample, including the presence, absence, or concentration levels of such markers or substances, and/or evaluating the values or categorization of a subject's clinical parameters.

The term "expression level data" refers to a value that represents a direct, indirect, or comparative measurement of the level of expression or abundance of a peptide, polypeptide, or protein. For example, "expression data" can refer to a value that represents a direct, indirect, or comparative measurement of the protein (or peptide fragment thereof) expression level of a proteomic marker of interest. The term "expression level" can also include the relative or absolute amount, quantity or abundance of a proteomic marker (e.g. a peptide, polypeptide or protein) in a sample.

The term "receiver operating characteristic" (ROC) refers to the performance of a classifier system as its discrimination threshold is varied.

A biomarker is "positively correlated" with AECOPD if the expression level or abundance of the biomarker is increased in subjects suffering from or diagnosed with AECOPD. A biomarker is "negatively correlated" with AECOPD if the expression level or abundance of the biomarker is decreased in subjects suffering from or diagnosed with AECOPD.

DETAILED DESCRIPTION OF THE INVENTION

Acute exacerbations of chronic obstructive pulmonary disease (AECOPD) result in considerable morbidity and mortality. While early diagnosis of AECOPD could potentially prevent long-standing complications, a blood-based biomarker for AECOPD has yet to be developed for clinical practice. Described herein are compositions and methods useful for diagnosing AECOPD, and distinguishing AECOPD from stable or convalescent clinical states of COPD. In some embodiments, the biomarkers are proteins or peptides, for example, proteins or peptides found in blood plasma or serum.

The compositions described herein include biomarkers that provide greater predictive value or diagnostic accuracy in diagnosing a COPD exacerbation compared to current biomarkers, such as C-reactive protein. In some embodiments, a biomarker score is calculated based on the weighted contributions of the marker proteins shown in Table 3, Table 7, or Table 10 or peptide fragments thereof. In some embodiments, the biomarker score is significantly greater in a subject with AECOPD than in a control subject without AECOPD. In some embodiments, the biomarker score is optimized to detect AECOPD with a sensitivity of at least 90% and/or a specificity of at least 86%. In some embodiments, the sensitivity of the biomarkers described herein for diagnosing AECOPD is at least 60%, 65%, 70%, 75%, 80%, 85%, 86%, 87%, 88%, 89%, 90%, 91%, 92%, 93%, 94%, 95%, 96%, 97%, or 98%. In some embodiments, the specificity of the biomarkers described herein for diagnosing AECOPD is at least 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%. In some embodiments, the decision threshold for the biomarker score is optimized to detect AECOPD with a sensitivity of at least 90%, and the resulting sensitivity is at least 90% and the resulting specificity is at least 30%. In some embodiments, the predictive value or diagnostic accuracy (e.g., the sensitivity and/or specificity for diagnosing AECOPD, the ROC curve, or the area under the curve (AUC) estimate) of assays that use the biomarkers described herein is greater than using the marker C-reactive protein (CRP) alone.

In some embodiments, the biomarkers provide an area under the curve (AUC) plateau of greater than 0.79, Markers and Clinical Factors In an embodiment, the methods described herein include obtaining a first dataset associated with a sample obtained from the subject (e.g., a blood sample), wherein the first dataset comprises quantitative expression data for one or more peptide or protein markers (e.g., expression data for two or more, three or more, four or more, or five or more markers) In some embodiments, the peptide or protein markers are selected from Table 2, Table 3, Table 4, Table 6, Table 7, or Table 10. In some embodiments, the peptide marker is a fragment of a protein selected from Table 2, Table 3, Table 4, Table 6, Table 7, or Table 10. This first sample can be taken, for example, during the exacerbation state of COPD or before treatment for AECOPD. In some embodiments, the method further includes analyzing the first dataset to determine the expression level or abundance of the one or more peptide or protein markers, wherein the expression level or abundance of the markers positively or negatively correlates with AECOPD in a subject.

In another embodiment, the methods described herein include obtaining a second dataset associated with a sample obtained from the subject (e.g., another blood sample), wherein the second dataset comprises quantitative expression data for one or more peptide or protein markers. In some embodiments, the peptide or protein markers are selected from Table 2, Table 3, Table 4, Table 6, Table 7, or Table 10. In some embodiments, the peptide marker is a fragment of a protein selected from Table 2, Table 3, Table 4, Table 6, Table 7, or Table 10. This second sample can be taken, for example, during the stable or convalescent state of COPD, or after treatment for AECOPD. In some embodiments, the method further includes analyzing the second dataset to determine the expression level of the one or more peptide or protein markers, wherein the expression level or abundance of the markers positively or negatively correlates with AECOPD in a subject.

In additional embodiments, the analysis includes both the first dataset and second dataset, wherein the aggregate analysis of marker expression levels positively or negatively correlates with AECOPD in a subject.

The quantity of one or more markers described herein can be indicated as a value. A value can be one or more numerical values resulting from evaluation of a sample. The values can be obtained, for example, by experimentally obtaining measures from a sample by an assay performed in a laboratory, or alternatively, obtaining a dataset from a service provider such as a laboratory, or from a database or a server on which the dataset has been stored, e.g., on a storage memory.

In an embodiment, the quantity of one or more markers can be one or more numerical values associated with the expression levels of peptides and/or proteins shown in Table 2, Table 3, Table 4, Table 6, Table 7, or Table 10 below, e.g., resulting from evaluation of a patient derived sample.

A marker's associated value can be included in a dataset associated with a sample obtained from a subject. A dataset can include the marker expression value of two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more marker(s). The value of the one or more markers can be evaluated by the same party that performed the assay using the methods described herein or sent to a third party for evaluation using the methods described herein.

In some embodiments, one or more clinical factors in a subject can be assessed. In some embodiments, assessment of one or more clinical factors or variables in a subject can be combined with a marker analysis in the subject to determine AECOPD in a subject. Examples of relevant clinical factors or variables include, but are not limited to, forced expiratory volume in 1 second (FEV1) <60% predicted, FEV1/forced vital capacity (FVC) <or equal to 70%, acute increase in dyspnea, sputum volume, and/or sputum purulence without an alternative explanation.

Assays

Examples of assays for one or more markers include sequencing assays, microarrays (e.g. proteome arrays), antibody-binding assays, enzyme-linked immunosorbent assays (ELISAs), flow cytometry, protein assays, western blots, nephelometry, turbidimetry, chromatography, mass spectrometry (e.g., MRM-MS), immunoassays, including, by way of example, but not limitation, RIA, immunofluorescence, immunochemiluminescence, immunoelectrochemiluminescence, or competitive immunoassays, immunoprecipitation, and the assays described in the Examples section below. The information from the assay can be quantitative and sent to a computer system described herein. The information can also be qualitative, such as observing patterns or fluorescence, which can be translated into a quantitative measure by a user or automatically by a reader or computer system. In an embodiment, the subject can also provide information other than assay information to a computer system, such as race, height, weight, age, sex, eye color, hair color, family medical history and any other information that may be useful to a user, such as a clinical factor or variable described herein.

Antibodies

In some embodiments, the markers described herein are detected with antibodies that specifically bind to peptides and proteins described herein. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide described herein is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')2 fragments which can be generated by treating the antibody with an enzyme such as pepsin. Described herein are polyclonal and monoclonal antibodies that bind to a polypeptide or peptide disclosed herein. The term "monoclonal antibody" or "monoclonal antibody composition," as used herein, refers to a population of antibody molecules that contain only one species of an antigen binding site capable of immunoreacting with a particular epitope of a polypeptide or peptide disclosed herein. A monoclonal antibody composition thus typically displays a single binding affinity for a particular polypeptide or peptide disclosed herein with which it immunoreacts.

Polyclonal antibodies can be prepared by immunizing a suitable subject with a desired immunogen, e.g., a polypeptide disclosed herein or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, Nature 256:495-497 (1975), the human B cell hybridoma technique (Kozbor et al., Immunol. Today 4: 72 (1983)), the EBV-hybridoma technique (Cole et al., Monoclonal Antibodies and Cancer Therapy, Alan R. Liss, 1985, Inc., pp. 77-96) or trioma techniques. The technology for producing hybridomas is well known (see generally Current Protocols in Immunology (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide described herein.

Any of the many well-known protocols used for fusing lymphocytes and immortalized cell lines can be applied for the purpose of generating a monoclonal antibody to a polypeptide described herein (see, e.g., Current Protocols in Immunology, supra; Golfre et al., Nature 266:55052 (1977);

R. H. Kenneth, in Monoclonal Antibodies: A New Dimension In Biological Analyses, Plenum Publishing Corp., New York, N.Y. (1980); and Lerner, Yale J. Biol. Med. 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide or peptide disclosed herein can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9: 1370-1372 (1991); Hay et al., Hum. Antibod. Hybridomas 3:81-85 (1992); Huse et al., Science 246: 1275-1281 (1989); and Griffiths et al., EMBO J. 12:725-734 (1993).

Additionally, recombinant antibodies, such as chimeric and humanized monoclonal antibodies, comprising both human and non-human portions, which can be made using standard recombinant DNA techniques, are within the scope of the instant disclosure. Such chimeric and humanized monoclonal antibodies can be produced by recombinant DNA techniques known in the art.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

In general, antibodies (e.g., polyclonal or monoclonal antibodies) can be used to detect a polypeptide marker (e.g., in a blood sample) in order to evaluate the abundance and expression of the polypeptide. The antibody can be coupled to a detectable substance to facilitate its detection. Examples of detectable substances include various enzymes, prosthetic groups, fluorescent materials, luminescent materials, bioluminescent materials; and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Detection Assays

Antibodies such as those described herein can be used in a variety of methods to determine the expression levels or abundance of the markers disclosed herein, and thus, determine AECOPD. In one aspect, kits can be made which comprise antibodies or reagents that can be used to quantify the markers of interest.

In another aspect, expression levels or abundance of polypeptide markers can be measured using a variety of methods, including enzyme linked immunosorbent assays (ELISAs), western blots, immunoprecipitations immunofluorescence, and mass spectrometry. For example, a test sample from a subject is subjected to a measurement of protein expression levels using marker-specific antibodies. Variants of the protein markers described herein can be detected using polyclonal antibodies that bind the canononical or reference amino acid sequence.

Various means of examining expression, composition, or abundance of the peptides or polypeptides described herein can be used, including: spectroscopy, colorimetry, electrophoresis, isoelectric focusing, and immunoassays (e.g., David et al., U.S. Pat. No. 4,376,110) such as immunoblotting (see also Current Protocols in Molecular Biology, particularly Chapter 10). For example, in one aspect, an antibody capable of binding to the polypeptide (e.g., as described above), preferably an antibody with a detectable label, can be used. Antibodies can be polyclonal, or monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling a DNA probe with biotin such that it can be detected with fluorescently labeled streptavidin.

Computer Implementation

In one embodiment, a computer comprises at least one processor coupled to a chipset. A memory, a storage device, a keyboard, a graphics adapter, a pointing device, and a network adapter can be coupled to the chipset. In some embodiments, a display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), MID, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

TREATMENTS

In some embodiments, the above methods further comprise providing a course of treatment based on the results of the assay using the markers described herein. In some embodiments, the course of treatment comprises short-acting beta2-agonists, such as albuterol; anticholinergic bronchodilators, such as ipratropium bromide; methylxanthines such as aminophylline and theophylline; long-acting bronchodilators; oral steroids such as prednisone and methylprednisone, expectorants, oxygen therapy, and/or antibiotics if indicated for a lung infection.

Examples of antibiotics include, for mild to moderate exacerbations:
Doxycycline (Vibramycin), 100 mg twice daily
Trimethoprim-sulfamethoxazole (Bactrim DS, Septra DS), one tablet twice daily
Amoxicillin-clavulanate potassium (Augmentin), one 500 mg/125 mg tablet three times daily or one 875 mg/125 mg tablet twice daily
Macrolides:
Clarithromycin (Biaxin), 500 mg twice daily
Azithromycin (Zithromax), 500 mg initially, then 250 mg daily.
Fluoroquinolones:
Levofloxacin (Levaquin), 500 mg daily
Gatifloxacin (Tequin), 400 mg daily
Moxifloxacin (Avelox), 400 mg daily.
For moderate to severe exacerbations:
Cephalosporins:
Ceftriaxone (Rocephin), 1 to 2 g IV daily
Cefotaxime (Claforan), 1 g IV every 8 to 12 hours
Ceftazidime (Fortaz), 1 to 2 g IV every 8 to 12 hours
Antipseudomonal Penicillins:
Piperacillin-tazobactam (Zosyn), 3.375 g IV every 6 hours
Ticarcillin-clavulanate potassium (Timentin), 3.1 g IV every 4 to 6 hours
Fluoroquinolones:
Levofloxacin, 500 mg IV daily
Gatifloxacin, 400 mg IV daily
Aminoglycoside:
Tobramycin (Tobrex), 1 mg per kg IV every 8 to 12 hours, or 5 mg per kg IV daily

EXAMPLES

Example 1

This Example describes the development of a panel of biomarkers that can distinguish AECOPD from a convalescent state.
Methods
Study Populations.
Biomarker discovery took place in 37 patients from the previously described and studied cohort evaluating the use of zileuton in the treatment of AECOPD (LEUKO) (15). Briefly, inclusion criteria were age >45 years, admission to the hospital for AECOPD, ≥10 pack-years smoking history, and a forced expiratory volume in 1 second (FEV1) <60% predicted. AECOPD was defined as an acute increase in dyspnea, sputum volume, and/or sputum purulence without an alternative explanation. Plasma samples used in this analysis were collected at the beginning of the hospitalization period and at day 30. We considered the initial sample collection at hospitalization to indicate an AECOPD whereas the day 30 sample was used to indicate a convalescent state.

Biomarker replication occurred in patients from two other COPD cohorts. The first cohort studied the use of etanercept or prednisone in the treatment of AECOPD (TNF-α; n=81) (16); the second cohort (The Rapid Transition Program or RTP, n=109) prospectively enrolled patients hospitalized for AECOPD for the primary purpose of biomarker discovery to diagnose and track AECOPD. Inclusion criteria for the TNF-α, cohort were age >35 years, AECOPD presenting to a physician or emergency department, FEV1 ≤70% predicted, FEV1/forced vital capacity (FVC) ≤70%, and ≥10 pack-years smoking history. AECOPD was diagnosed when two of the following three criteria were met: increased dyspnea, sputum volume, and sputum purulence. Plasma samples used in this analysis were obtained at baseline and at 14 days. The baseline sample was considered to indicate an AECOPD whereas the 14 day sample was used to indicate a convalescent state. For the RTP cohort, subjects had to be ≥19 years of age and admitted to the hospital with an AECOPD as determined by general internists or pulmonologists. Blood samples were collected at the time of admission to the hospital (indicating an AECOPD state) and at either day 30 or day 90 following admission (indicating the convalescent state)

Sample Collection.

Blood samples were collected in P100 plasma tubes (BD, Franklin Lake, N.J.) and stored on ice until processing. Blood was spun down within two hours of collection and plasma was stored at −80° until selected for proteomic analysis. Patient plasma samples were analyzed using MRM-MS at the UVic Genome BC Proteomics Centre (Victoria, BC, Canada) according to methods described previously (17). There were 230 peptides measured corresponding to 129 proteins, chosen on the basis of both a literature search and from a previous untargeted iTRAQ mass spectrometry analysis on COPD patients. Further details regarding the MRM-MS process, the iTRAQ mass spectrometry analysis, and the peptides measured in this disclosure are provided in Example 2.

Statistical Analyses.

Pre-processing of the MRM-MS data involved several steps. All peptides that had more than 25% missing values across all samples or did not pass quality control metrics were removed. Missing values were imputed with a value half of the minimum peptide expression, for each peptide separately. Relative response of peptide abundance to stable isotopically-labeled peptide abundance were log-base 2 transformed and summarized at the protein level to create protein expression data.

Biomarker discovery was performed on the protein expression data using R (www.r-project.org) and Bioconductor (www.bioconductor.org). Proteins that passed all quality control metrics were analyzed for differential expression between the patients' exacerbation and convalescent samples, using limina (limina Bioconductor package). A false discovery rate (FDR) ≤0.2 was used as the criterion for selecting candidate proteins. An elastic net logistic regression model (18) (glmnet R package) was applied to the list of candidate proteins to build a classifier or biomarker score, which is the aggregation of the weighted contributions (linear predictors) of each protein in the model to the presence of AECOPD:

$$\text{Biomarker score} = w_0 + w_1 * \text{protein}_1 + w_2 * \text{protein}_2 + \ldots + w_N * \text{protein}_N$$

The performance characteristics of this biomarker score were estimated using leave-pair-out cross-validation (LPOCV). The LPOCV-based biomarker scores were also used to select decision thresholds, chosen such that convalescence or exacerbation would be detected with at least 90% success and Youden's index would be optimized. The classification model and decision thresholds obtained from LEUKO were applied to TNF-α and RTP data for external replication. A summary of the overall workflow is shown in FIG. 1. To determine the minimum number of proteins required to reach an AUC plateau, a stepwise AUC analysis was performed with the incremental addition of each protein to the model using data pooled from all three cohorts. Finally, enrichment analysis was performed using MetaCore (Thomson Reuters) on the biomarker proteins to determine relevant biological networks in plasma associated with AECOPD.

Results

Cohort Demographics.

The demographic characteristics comparing the LEUKO, TNF-α, and RTP cohorts are shown in Table 1. Patients from the LEUKO and RTP cohorts were more likely to be male than patients in the TNF-α cohort, while patients from the TNF-α cohort were more likely to be white. On average, patients enrolled in the three cohorts had moderate-to-severe COPD by spirometry. The majority of patients were being treated with bronchodilators.

Biomarker Panel Performance.

Figure 2:
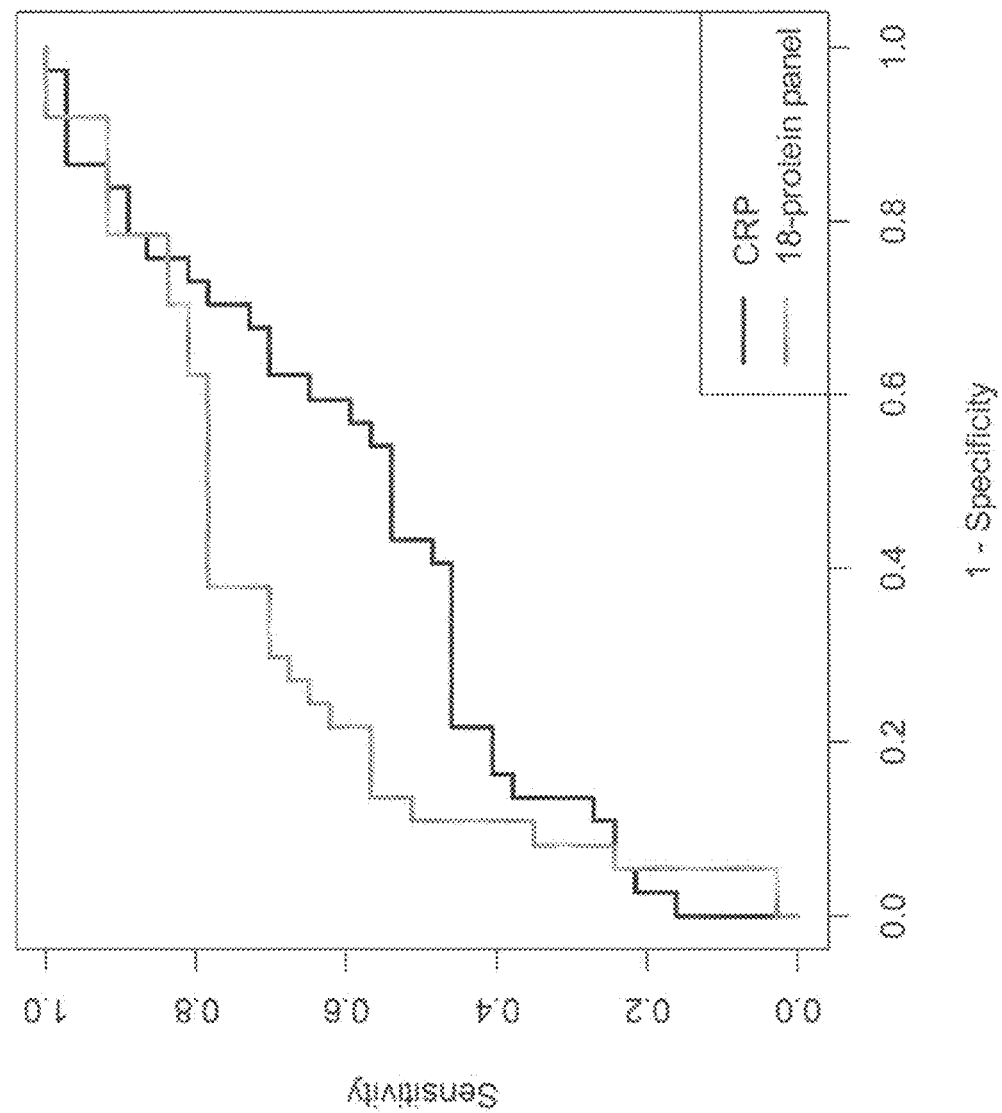
FIG. 2. Receiver Operating Characteristic (ROC) Curves for the LEUKO Discovery Cohort. The ROC curves are shown for CRP only (black line) and the 18-protein panel (orange line) when applied to the LEUKO discovery cohort. The 18-protein panel had improved performance metrics over CRP only.

After quality check and pre-processing, the protein expression data consisted of 55 proteins. Of these, 21 had differential levels between exacerbation and convalescent time points at a FDR <0.2 (Table 2). The final elastic net model consisted of 18 of these proteins (plasma serine protease inhibitor, plasma kallikrein, and insulin-like growth factor-binding protein 3 were removed to create the final model). Compared to CRP alone, the 18-protein panel demonstrated a superior receiver operating characteristic (ROC) curve for diagnosing AECOPD in the LEUKO discovery cohort (FIG. 2). The area under the curve (AUC) estimate in the LEUKO cohort was 0.70 compared to 0.60 for CRP. The AUC estimates for the replication cohorts were 0.72 and 0.72 for the TNF-α and RTP cohorts, respectively.

Figure 3:
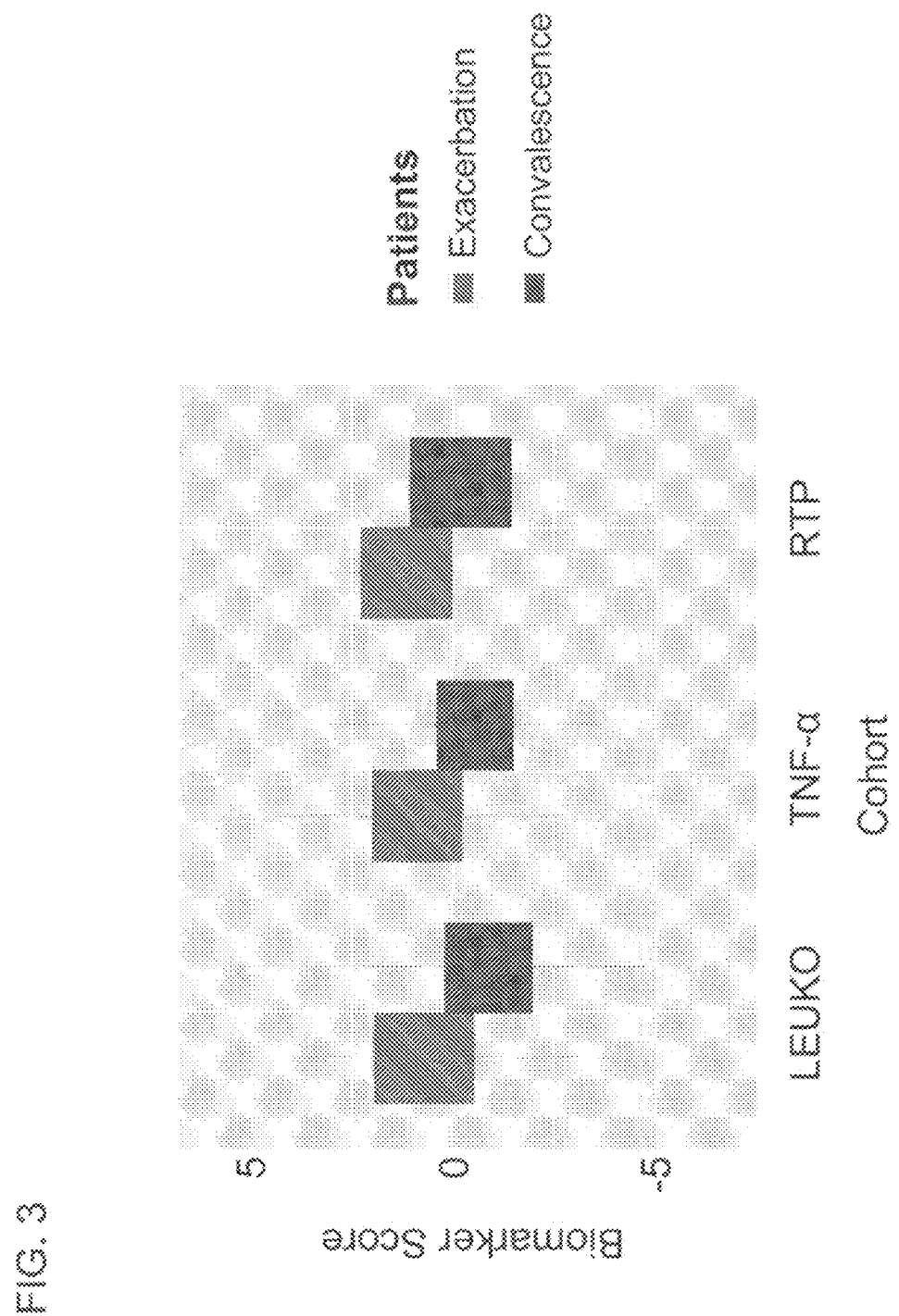
FIG. 3. Biomarker Scores Comparing AECOPD to Non-AECOPD States. Biomarker scores for the LEUKO, TNF-α, and RIP cohorts are shown with red denoting patients during AECOPD and blue denoting patients in the convalescent phase. Biomarker scores were significantly elevated during the time of AECOPD but fell during the convalescent phase (Wilcoxon rank sum p-value=0.001 for LEUKO, <0.0001 for TNF-α, and <0.0001 for RTP). The convalescent phase scores for the LEUKO, TNF-α, and RTP cohorts were not statistically significantly different.

A biomarker score based on the weighted contributions of the 18 proteins to the presence of an AECOPD state was calculated for each of the cohorts. The intercept and specific protein weights contributing to the biomarker score for the 18-protein panel are listed in Table 3. Biomarker scores at each time point for the three cohorts are shown in FIG. 3. In all three cohorts, the biomarker scores at exacerbation time points were significantly greater than the biomarker scores at convalescent time points (Wilcoxon rank sum p-value=0.001 for LEUKO, <0.0001 for TNF-α, and <0.0001 for RTP). As well, the biomarker scores during convalescence in the two replication cohorts were not statistically different from the convalescence biomarker scores in the LEUKO discovery cohort.

A biomarker score decision threshold optimized to detect AECOPD with 90% sensitivity in the LEUKO cohort yielded sensitivities of 92%, 81%, and 98% in the LEUKO, TNF-α, and RTP cohorts, respectively. Conversely, a biomarker score decision threshold optimized to detect AECOPD with 90% specificity in the LEUKO cohort yielded specificities of 92%, 100%, and 86% in the LEUKO, TNF-α, and RTP cohorts, respectively Stepwise AUC Selection.

Figure 4:
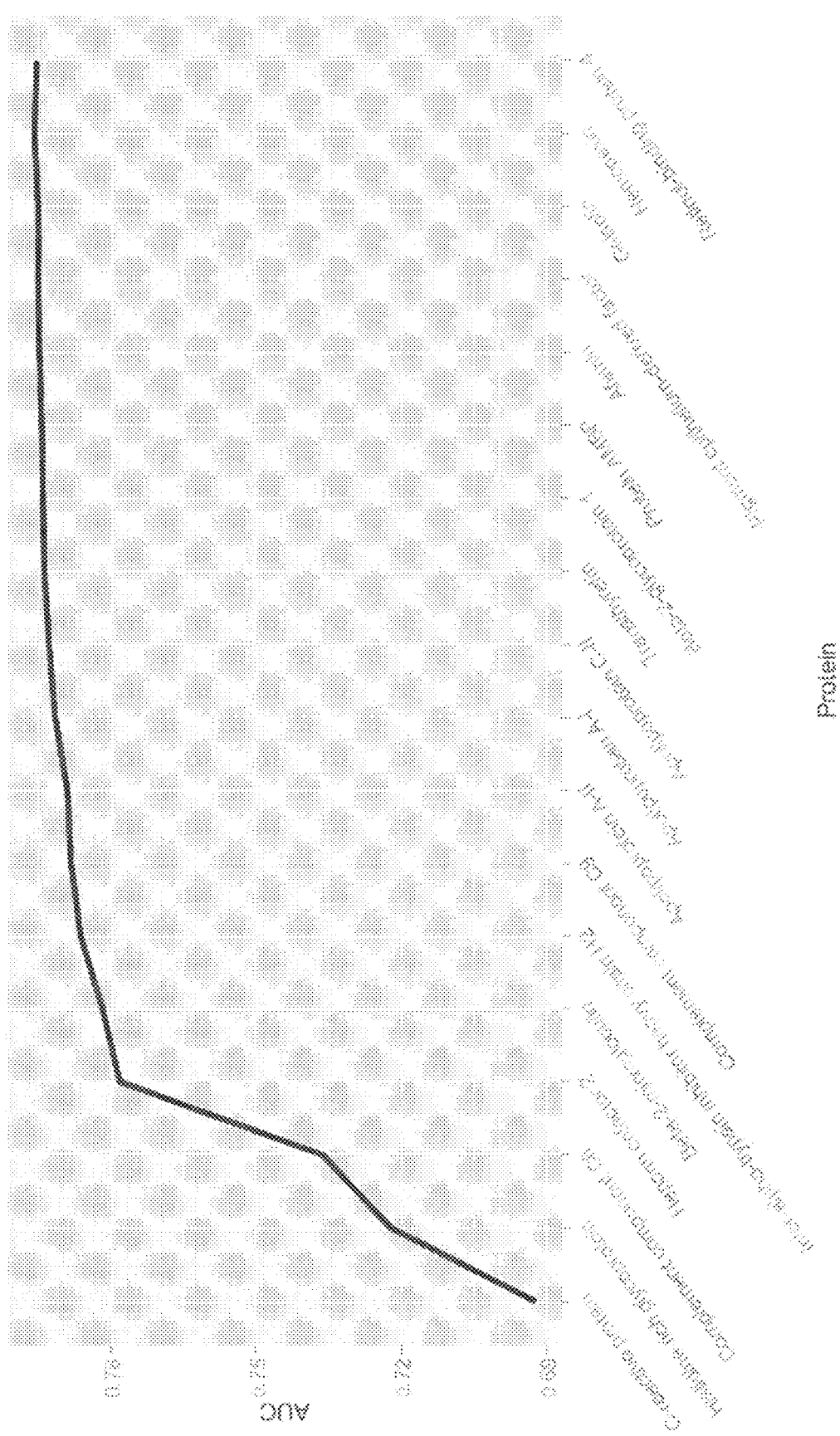
FIG. 4. Stepwise AUC Analysis for Pooled Data. Incremental increases in AUC are graphed with each stepwise addition of a protein from the 18-protein panel for all three cohorts combined. A plateau AUC of 0.795 is achieved with the first 11 proteins.

Using the pooled data from all three cohorts, the 18 proteins in the biomarker panel were assembled using a stepwise AIX selection to determine incremental predictive ability with each additional protein (FIG. 4). An AUC plateau of 0.795 was achieved with 11 of the 18 proteins, suggesting that a smaller subset of the panel could potentially be used with minimal loss to the overall AUC.

Process Network Analysis.

Figure 5:
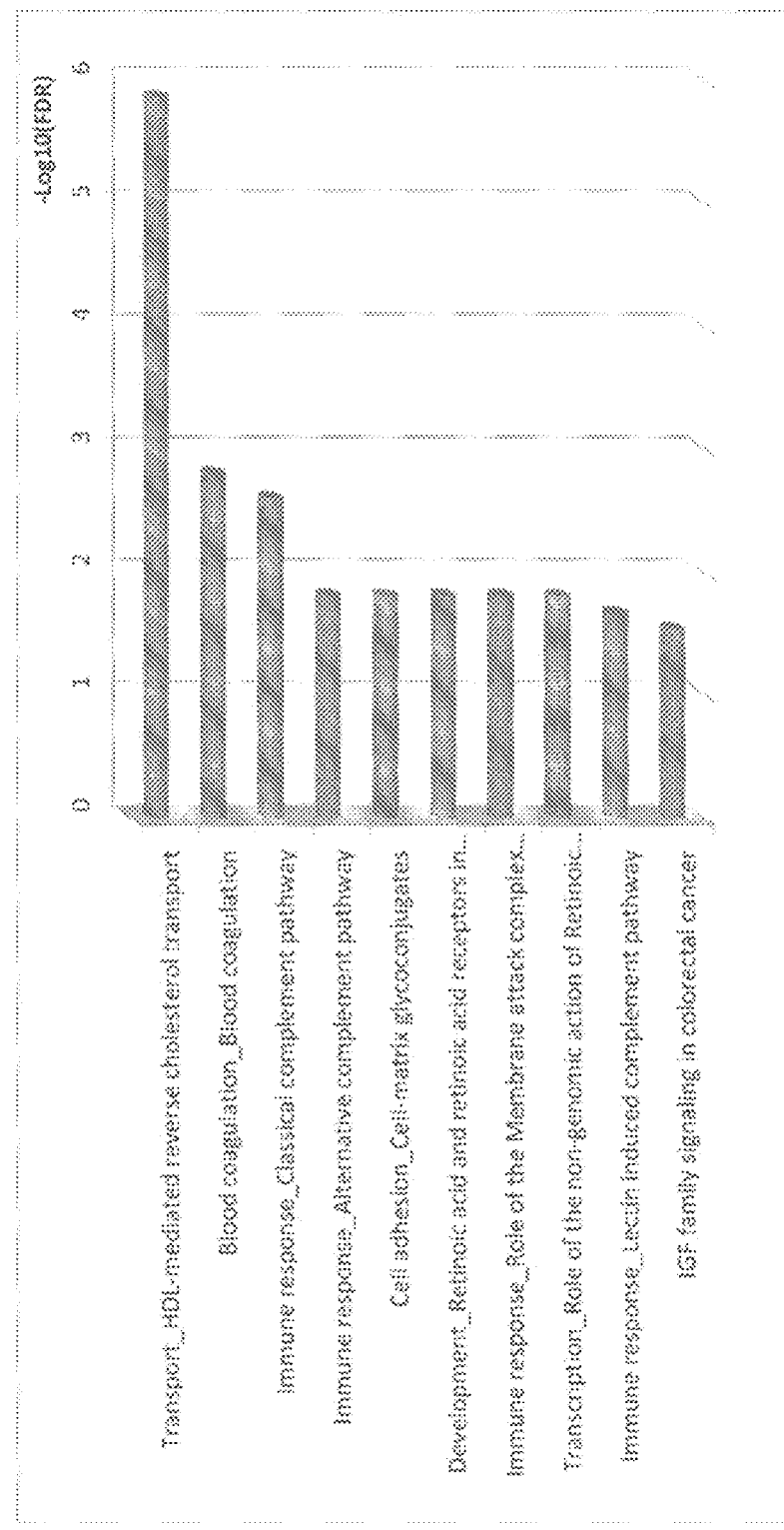
FIG. 5. Pathways Enriched By Statistically Significant Proteins. Significant process networks associated with the 21-protein biomarker panel are shown. The most significant pathway enriched by the biomarker proteins was HDL cholesterol transport ($p=3.82 \times 10^{-8}$), followed by blood coagulation ($p=8.90 \times 10^{-5}$), classical and alternative complement pathways ($p=2.11 \times 10^{-4}$ and $p=2.67 \times 10^{-3}$, respectively) and cell adhesion pathways ($p=3.32 \times 10^{-3}$).

Results from the process network analysis are shown in FIG. 5. The 21 differentially expressed proteins were most significantly enriched for the high density lipoprotein (HDL) cholesterol transport pathway (p-value=$3.82 \times 10^{-8}$). Other significant pathways included blood coagulation (p-value=$8.90 \times 10^{-5}$), classical and alternative complement pathways (p-value=$2.11 \times 10^{-4}$ and p-value=$2.67 \times 10^{-3}$, respectively) and cell adhesion pathways (p-value=$3.32 \times 10^{-3}$).

Discussion

In this first-ever study employing MRM-MS for biomarker verification in AECOPD, we have generated a panel of 18 proteins significantly associated with an AECOPD state with the results replicated in two separate AECOPD cohorts. The performance of this panel was a marked improvement over more commonly used measures like CRP. Biomarker scores derived from this panel were significantly elevated in AECOPD, subsequently falling during convalescent periods. For a condition with a current dearth of available biomarkers at its disposal, this panel may represent a significant step forward not only in AECOPD diagnosis but also in the recognition of AECOPD resolution at which point therapy could potentially be tapered. While the AUC estimates for this protein panel remain modest, this may simply be due to the fact that COPD exacerbations are fundamentally heterogeneous in etiology and that we currently lack a gold standard for diagnosis outside of our own clinical acumen.

Whether this particular biomarker panel can also predict AECOPD severity or AECOPD-related mortality, fluctuate in accordance with disease progression during an AECOPD, or identify patients at risk for an imminent AECOPD remains to be determined, but is grounds for further prospective study. As well, transitioning this biomarker panel to a multiplexed, clinical assay for prospective study in a real-world setting is a necessary next step. While an 18-protein panel may indeed prove difficult to transition to a clinically practical platform, our pooled analysis of incremental AUC gain suggests that simplification of the 18-protein panel to a smaller number of proteins is feasible without significant loss of predictive power.

The MRM-MS approach, although previously applied to numerous other disease states such as lung cancer, psoriatic arthritis, and Parkinson's disease (14, 19, 20), marks a departure from traditional methods of biomarker discovery and verification in AECOPD. Previous attempts to identify biomarkers have interrogated known proteins with already available commercial immunoassay platforms, for instance CRP, angiopoietin-2, adrenomedullin, and troponin (6, 21-24), Unfortunately, proteins without such assays available may be entirely overlooked by this strategy. The cost and time required for immunoassay development, however, can be prohibitive (25). MRM-MS can fill this gap between biomarker discovery and verification by providing a cost-effective platform that can quantify proteins with greater sensitivity and specificity than that provided by immunoassays. Moreover, the multiplexing capacity of MRM-MS confers another distinct advantage over antibody-based tests.

As a result, we identified through our protein panel key biological pathways not previously associated with AECOPD pathophysiology. While inflammatory proteins like CRP were indeed differentially expressed in AECOPD, inflammatory pathways were not in fact the most significant biological networks involved, a surprising finding given the extensive attention recently focused on inflammation in the etiology of AECOPD. Instead, AECOPD were most significantly associated with the HDL cholesterol pathway, with decreases in both apolipoprotein A-I (APOA1) and apolipoprotein A-II (APOA2) observed. While the associations between AECOPD and cardiovascular comorbidities have long been recognized (8, 26, 27), the specific role that HDL plays in the development of AECOPD has not yet been established. APOA1 is the major protein structure found in HDL, making up 70% of its weight, while APOA2 accounts for approximately 20% of the HDL protein (28). Deficiencies in APOA1 can lead to low HDL levels, accelerated coronary artery disease, early onset myocardial infarctions and elevated inflammatory markers such as CRP (29). Similarly, while the function of APOA2 remains largely unknown and deficient states have yet to be fully clinically characterized, lower APOA2 levels are nonetheless observed in patients with myocardial infarctions compared to normal controls (30). That AECOPD could be associated with low HDL states or triggered by small myocardial infarctions might suggest a particular cardiac phenotype of AECOPD distinct from infectious or inflammatory etiologies that can be identified by our protein panel.

Another plausible mechanism by which low APOA1 and APOA2 could lead to AECOPD might relate to their antioxidant properties. Both APOA1 and APOA2 carry paraoxonase 1 (PON1), an antioxidant and antiatherogenic enzyme that furthermore can localize to key lung compartments such as club cells and type 1 pneumocytes (31). PON1 activity is decreased in the presence of cigarette smoke (32) and patients with COPD have lower serum levels of PON1 compared to healthy subjects (33). Low APOA1 and APOA2 levels could potentially aggravate an already PON1-deficient state, rendering the lung acutely vulnerable to further oxidative stresses. Although purely speculative at this time, this could hypothetically be the trigger for an AECOPD. Nonetheless, evidence in the literature is still conflicting regarding HDL and COPD. For instance, one study has found that higher, not lower, HDL levels are associated with worse airflow obstruction and greater emphysema (34). On the other hand, a recent investigation of serum from atopic asthmatic subjects revealed that both HDL and APOA1 levels are positively correlated with FEV1 (35). Future studies clarifying the role of HDL and HDL-related proteins in the pathogenesis of AECOPD and other diseases of the airways are clearly warranted.

Figure 6:
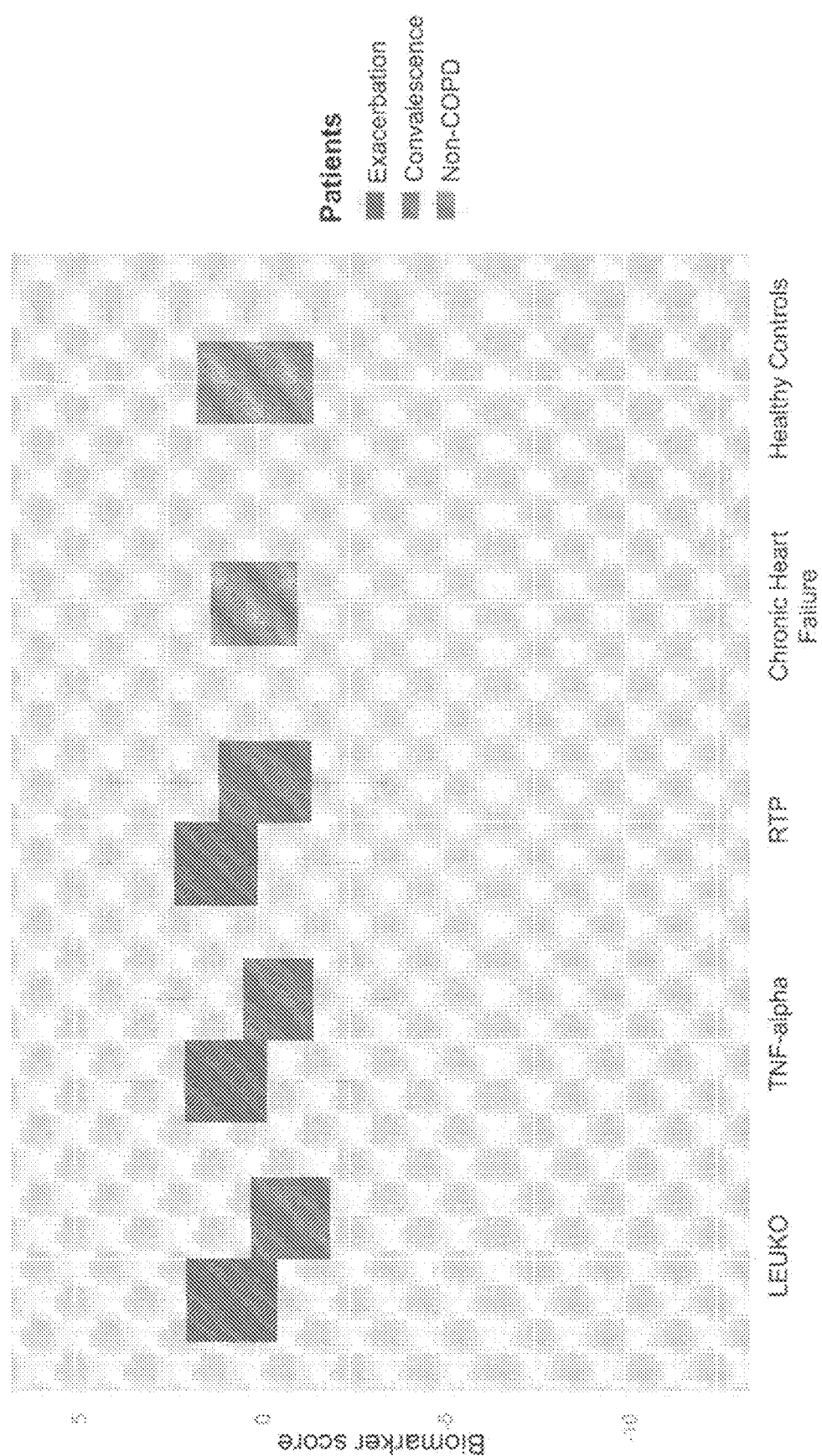
FIG. 6. Biomarker Scores in Stable Congestive Heart Failure Patients and Normal Controls. Biomarker scores for the 18-protein panel are shown for a cohort of stable chronic heart failure patients and for normal controls to compare with the three AECOPD cohorts. Scores for the chronic heart failure patients and for the normal controls were not statistically different from the convalescent scores of the three AECOPD cohorts.
Figure 7:
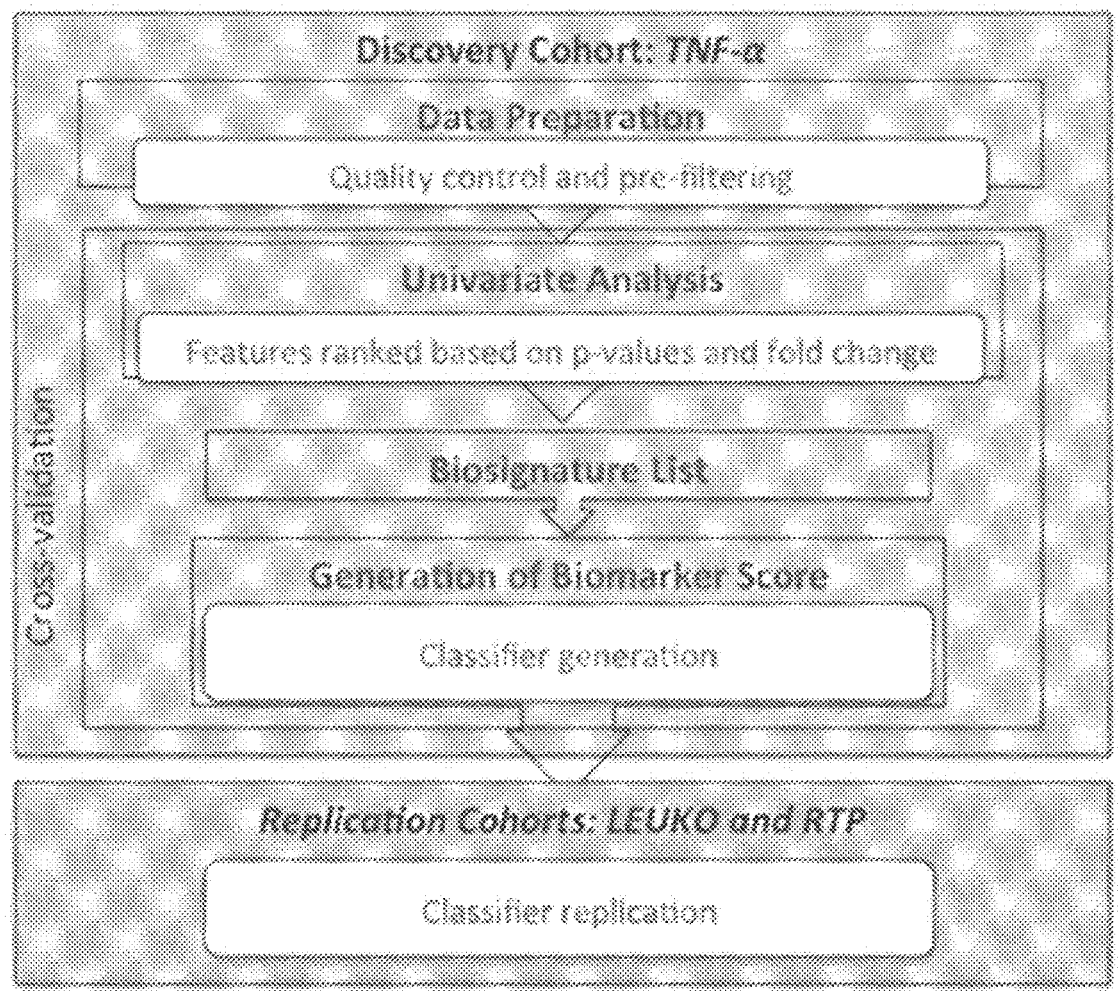
FIG. 7. Biomarker Discovery and Replication Strategy. Biomarker discovery steps, applied to the TNF-α cohort, are outlined in the pink box. After pre-processing, univariate analysis identifies candidate proteins based on statistically significant differences between AECOPD and convalescent at a false discovery rate <0.01 with a fold change >1.2. An elastic net model is applied to these candidate proteins to generate a final classifier model. This is subsequently followed by replication in the LEUKO and RTP cohorts (blue box).

There were several limitations to our study. First, the three cohorts utilized for biomarker discovery and verification were fundamentally different in terms of baseline demographic markers like age, sex, and lung function. Therefore, the protein panel discovered in the LEUKO cohort may have actually performed better had the subjects in the verification cohorts aligned more similarly with the discovery cohort. However, this study demonstrates that the biomarker panel can likely be applied across a wide variety of COPD phenotypes with consistent results. Secondly, the MRM-MS approach is limited by the list of peptides initially chosen for analysis. In this sense, it relies completely on an a priori assessment and cannot as such be considered a truly comprehensive evaluation of all possible biomarkers. In the present study, we conducted a hypothesis-free, unbiased proteomics experiment using iTRAQ which informed the choice of peptides that were interrogated with MRM-MS. Nevertheless, given the limitations of iTRAQ and other unbiased proteomics platforms currently available, almost certainly there are as yet undiscovered proteins that are likely to play a significant role in AECOPD. Finally, the performance of the protein panel in clinical states that can often be confused with AECOPD, such as congestive heart failure exacerbations, pneumonia, and pulmonary embolus, is unknown but would be critical in determining its ultimate use in undifferentiated patients presenting with non-specific symptoms such as dyspnea. It should be noted that we applied the 18-protein biomarker panel to a cohort of stable congestive heart failure patients and to a cohort of healthy controls, the resulting biomarker scores were equivalent to those of non-exacerbating COPD patients (see FIG. 6).

In summary, we demonstrate for the first time the application of the MRM-MS platform to biomarker discovery in the diagnosis of AECOPD. Not only could this panel distinguish AECOPD from the convalescent COPD state in multiple, independent cohorts, but it also revealed potential novel mechanisms for AECOPD by implicating HDL cholesterol pathways previously unreported in the AECOPD literature.

REFERENCES

1. Donaldson G C, Seemungal T A, Bhowmik A, Wedzicha J A. Relationship between exacerbation frequency and lung function decline in chronic obstructive pulmonary disease. *Thorax* 2002; 57: 847-852.
2. Seemungal T A, Donaldson G C, Paul E A, Bestall J C, Jeffries D J, Wedzicha J A. Effect of exacerbation on quality of life in patients with chronic obstructive pulmonary disease. *Am J Respir Crit Care Med* 1998; 157: 1418-1422.
3. Soler-Cataluna J J, Martinez-Garcia M A, Roman Sanchez P, Salcedo E, Navarro M, Ochando R. Severe acute exacerbations and mortality in patients with chronic obstructive pulmonary disease. *Thorax* 2005; 60: 925-931.
4. Chronic obstructive pulmonary disease (COPD) fact sheet. Chicago, Ill.: American Lung Association, 2014. (Accessed Oct. 4, 2014)
5. Celli B R, MacNee W. Standards for the diagnosis and treatment of patients with COPD: a summary of the ATS/ERS position paper. *Eur Respir J* 2004; 23: 932-946.
6. Hurst J R, Donaldson G C, Perera W R, Wilkinson T M, Bilello J A, Hagan G W, Vessey R S, Wedzicha J A. Use of plasma biomarkers at exacerbation of chronic obstructive pulmonary disease. *Am J Respir Crit Care Med* 2006; 174: 867-874.
7. Bozinovski 5, Hutchinson A, Thompson M, Macgregor L, Black J, Giannakis E, Karlsson A S, Silvestrini R, Sinallwood D, Vlahos R, Irving L B, Anderson G P. Serum amyloid a is a biomarker of acute exacerbations of chronic obstructive pulmonary disease. *Am J Respir Crit Care Med* 2008; 177: 269-278.
8. Patel A R, Kowlessar B S, Donaldson G C, Mackay A J, Singh R, George S N, Garcha D S, Wedzicha J A, Hurst J R. Cardiovascular risk, myocardial injury, and exacerbations of chronic obstructive pulmonary disease. *Am J Respir Crit Care Med* 2013; 188: 1091-1099.
9. Seemungal T, Harper-Owen R, Bhowmik A, Moric I, Sanderson G, Message S, Maccallum P, Meade T W, Jeffries D J, Johnston S L, Wedzicha J A. Respiratory viruses, symptoms, and inflammatory markers in acute exacerbations and stable chronic obstructive pulmonary disease. *Am J Respir Crit Care Med* 2001; 164: 1618-1623,
10. Peacock J L, Anderson H R, Bremner S A, Marston L, Seemungal T A, Strachan D P, Wedzicha J A. Outdoor air pollution and respiratory health in patients with COPD. *Thorax* 2011; 66: 591-596.
11. De Serres G, Lampron N, La Forge J, Rouleau I, Bourbeau J, Weiss K, Barret B, Boivin G. Importance of viral and bacterial infections in chronic obstructive pulmonary disease exacerbations. *J Clin Virol* 2009; 46: 129-133.
12. Meng Z, Veenstra T D. Targeted mass spectrometry approaches for protein biomarker verification. *J Proteomics* 2011; 74: 2650-2659.
13. Method of the Year 2012. *Nat Methods* 2012; 10: 1.
14. Chen C D, Wang C L, Yu C J, Chien K Y, Chen Y T, Chen M C, Chang Y S, Wu C C, Yu J S. Targeted proteomics pipeline reveals potential biomarkers for the diagnosis of metastatic lung cancer in pleural effusion. *J Proteome Res* 2014; 13: 2818-2829.
15. Woodruff P G, Albert R K, Bailey W C, Casaburi R, Connett J E, Cooper J A, Jr., Criner G J, Curtis J L, Dransfield M T, Han M K, Hamden S M, Kim V, Marchetti N, Martinez F J, McEvoy C E, Niewoehner D E, Reilly J J, Rice K, Scanlon P D, Scharf S M, Sciurba F C, Washko G R, Lazarus S C. Randomized trial of zileuton for treatment of COPD exacerbations requiring hospitalization. *COPD* 2011; 8: 21-29.
16. Aaron S D, Vandemheen K L, Maltais F, Field S K, Sin D D, Bourbeau J, Marciniuk D D, FitzGerald J M, Nair P, Mallick R. TNFalpha antagonists for acute exacerbations of COPD: a randomised double-blind controlled trial. *Thorax* 2013; 68: 142-148.
17. Percy A J, Chambers A G, Yang J, Jackson A M, Domanski D, Burkhart J, Sickmann A, Borchers C H. Method and platform standardization in MRM-based quantitative plasma proteomics. *J Proteomics* 2013; 95: 66-76.
18. Zou H, Hastie T. Regularization and variable selection via the elastic net. *J R Stat Soc Series B* 2005; 67: 301-320.
19. Ademowo O S, Hernandez B, Collins E, Rooney C, Fearon U, van Kuijk A W, Tak P P, Gerlag D M, FitzGerald O, Pennington S R. Discovery and confirmation of a protein biomarker panel with potential to predict response to biological therapy in psoriatic arthritis. *Ann Rheum Dis* 2014 Sep. 3 [Epub ahead of print].
20. Alberio T, McMahon K, Cuccurullo M, Gethings L A, Lawless C, Zibetti M, Lopiano L, Vissers J P, Fasano M. Verification of a Parkinson's disease protein signature in T-lymphocytes by multiple reaction monitoring. *J Proteome Res* 2014; 13: 3554-3561.
21. Meng D Q, Li X J, Song X Y, Xin J B, Yang W B. Diagnostic and Prognostic Value of Plasma Adrenomedullin in COPD Exacerbation. *Respir Care* 2014; 59:1542-9.
22. Wedzicha J A, Seemungal T A, MacCallum P K, Paul E A, Donaldson G C, Bhowmik A, Jeffries D J, Meade T W. Acute exacerbations of chronic obstructive pulmonary disease are accompanied by elevations of plasma fibrinogen and serum IL-6 levels. *Thromb Haemost* 2000; 84: 210-215.
23. Nikolakopoulou S, Hillas G, Perrea D, Tentolouris N, Loukides S, Kostikas K, Simoes D, Georgakopoulou E, Vogiatzakis E, Veldekis D, Bakakos P. Serum angiopoietin-2 and CRP levels during COPD exacerbations. *COPD* 2014; 11: 46-51.
24. Soyseth V, Bhatnagar R, Holmedahl N H, Neukamm A, Hoiseth A D, Hagve T A, Einvik G, Omland T. Acute exacerbation of COPD is associated with fourfold elevation of cardiac troponin T. *Heart* 2013; 99: 122-126.
25. Issaq H J, Veenstra T D. Would you prefer multiple reaction monitoring or antibodies with your biomarker validation? *Expert Rev Proteomics* 2008; 5: 761-763.
26. Donaldson G C, Hurst J R, Smith C J, Hubbard R B, Wedzicha J A. Increased risk of myocardial infarction and stroke following exacerbation of COPD. *Chest* 2010; 137: 1091-1097.
27. McAllister D A, Maclay J D, Mills N L, Leitch A, Reid P, Carruthers R, O'Connor J, McAlpine L, Chalmers G, Newby D E, Clark E, Macfarlane P W, Macnee W. Diagnosis of myocardial infarction following hospitalisation for exacerbation of COPD. *Eur Respir J* 2012; 39: 1097-1103.
28. Maiga S F, Kalopissis A D, Chabert M. Apolipoprotein A-II is a key regulatory factor of HDL metabolism as appears from studies with transgenic animals and clinical outcomes. *Biochimie* 2014; 96: 56-66.
29. Al-Sarraf A, Al-Ghofaili K, Sullivan D R, Wasan K M, Hegele R, Frohlich J. Complete Apo AI deficiency in an Iraqi Mandaean family: case studies and review of the literature. *J Clin Lipidol* 2010; 4: 420-426.
30. Buring J E, O'Connor G T, Goldhaber S Z, Rosner B, Herbert P N, Blum C B, Breslow J L, Hennekens C H. Decreased HDL2 and HDL3 cholesterol, Apo A-I and Apo A-II, and increased risk of myocardial infarction. *Circulation* 1992; 85: 22-29.
31. Rodrigo L, Hernandez A F, Lopez-Caballero J J, Gil F, Pla A. Immunohistochemical evidence for the expression and induction of paraoxonase in rat liver, kidney, lung and brain tissue. Implications for its physiological role. *Chem Biol Interact* 2001; 137: 123-137.
32. Isik B, Ceylan A, Isik R. Oxidative stress in smokers and non-smokers. *Inhal Toxicol* 2007; 19: 767-769.
33. Rumora L, Rajkovic M G, Kopcinovic L M, Pancirov D, Cepelak I, Grubisic T Z. Paraoxonase 1 activity in patients with chronic obstructive pulmonary disease. *COPD* 2014; 11: 539-545.
34. Burkart K M, Manichaikul A, Wilk J B, Ahmed F S, Burke G L, Enright P, Hansel N N, Haynes D, Heckbert S R, Hoffman E A, Kaufman J D, Kurai J, Loehr L, London S J, Meng Y, O'Connor G T, Oelsner E, Petrini M, Pottinger T D, Powell C A, Redline S, Rotter J I, Smith L J, Soler Artigas M, Tobin M D, Tsai M Y, Watson K, White W, Young T R, Rich S S, Barr R G. APOM and high-density lipoprotein cholesterol are associated with lung function and percent emphysema. *Eur Respir J* 2014; 43: 1003-1017.
35. Barochia A V, Kaler M, Cuento R A, Gordon E M, Weir N A, Sampson M, Fontana J R, MacDonald S, Moss J, Manganiello V, Remaley A T, Levine S J. Serum Apolipoprotein A-I and Large HDL Particles are Positively Correlated with FEV in Atopic Asthma. *Am J Respir Crit Care Med* 2015 Feb. 18 [Epub ahead of print].

TABLE 1

Demographic Data for LEUKO, TNF-α, and RTP Cohorts

| Characteristic | LEUKO (n = 37) | TNF-α (n = 81) | RTP (n = 109) | p-value* |
|---|---|---|---|---|
| Age (years) | 62.11 ± 8.19 | 67.06 ± 9.28 | 67.79 ± 10.54 | 0.009 |
| Male (%) | 56.76 | 37.04 | 63.30 | 0.001 |
| BMI (kg/m$^2$) | 27.04 ± 5.65 | 26.56 ± 7.14 | 27.37 ± 6.88 | 0.852 |
| White Race (%) | 59.46 | 98.77 | 82.41 | <0.001 |
| Smoking Status | | | | <0.001 |
| Current (%) | 29.73 | 23.46 | 52.29 | |
| Former (%) | 70.27 | 70.37 | 33.94 | |
| Smoking pack-years | 47.86 ± 28.02 | 47.85 ± 28.23 | 53.39 ± 36.05 | 0.476 |
| FEV1 (L) (Exacerbation) | 1.00 ± 0.62 | 0.94 ± 0.47 | 1.66 ± 0.85 | <0.001 |
| FEV1 (% Predicted) (Exacerbation) | 31.92 ± 15.27 | 34.41 ± 13.87 | 57.19 ± 20.11 | <0.001 |
| FVC (L) (Exacerbation) | 2.35 ± 0.93 | 2.33 ± 1.00 | 2.98 ± 1.16 | 0.007 |
| FVC (% Predicted) (Exacerbation) | N/A | 66.65 ± 20.88 | 81.28 ± 19.28 | 0.001 |
| FEV1/FVC (%) (Exacerbation) | 41.92 ± 11.61 | 40.78 ± 13.14 | 55.52 ± 13.82 | <0.001 |
| FEV1 (L) (Convalescence) | 1.00 ± 0.58 | N/A | 1.34 ± 0.60 | 0.074 |
| FEV1 (% Predicted) (Convalescence) | 34.79 ± 17.39 | N/A | 49.64 ± 16.19 | 0.009 |
| FVC (L) (Convalescence) | 2.36 ± 0.86 | N/A | 2.67 ± 0.79 | 0.252 |
| FVC (% Predicted) (Convalescence) | 63.28 ± 20.07 | N/A | 76.21 ± 18.49 | 0.044 |
| FEV1/FVC (%) (Convalescence) | 41.83 ± 15.83 | N/A | 51.47 ± 16.47 | 0.064 |
| Bronchodilator Use (%) | 94.59 | 100 | 95.42 | 0.134 |
| Inhaled Corticosteroid Use (%) | 67.57 | 95.00 | 44.95 | <0.001 |

Abbreviations: BMI — body mass index;
FEV1 — forced expiratory volume in 1 second;
FVC — forced capacity;
N/A: not available
*P-values were generated using an ANOVA test for continuous variables and chi-square tests for categorical variables.

TABLE 2

Significant Proteins Differently Expressed in AECOPD Compared to the Convalescent State

| Peptide | Protein Name | UniProt ID | Gene Symbol | P-value | FDR | Fold Change | Direction AECOPD Relative to Convalescence |
|---|---|---|---|---|---|---|---|
| TAAQNLYEK (SEQ ID NO: 1) | Apolipoprotein C-II | P02655 (SEQ ID NO: 22) | APOC2 | 0.0001 | 0.0068 | 1.20 | down |
| IAPQLSTEELVSLGEK (SEQ ID NO: 2) | Afamin | P43652 (SEQ ID NO: 23) | AFM | 0.0004 | 0.0100 | 1.24 | down |
| ATEHLSTLSEK (SEQ ID NO: 3) | Apolipoprotein A-I | P02647 (SEQ ID NO: 24) | APOA1 | 0.0012 | 0.0181 | 1.12 | down |
| YWGVASFLQK (SEQ ID NO: 4) | Retinol-binding protein 4 | P02753 (SEQ ID NO: 25) | RBP4 | 0.0015 | 0.0181 | 1.33 | down |
| SPELQAEAK (SEQ ID NO: 5) | Apolipoprotein A-II | P02652 (SEQ ID NO: 26) | APOA2 | 0.0016 | 0.0181 | 1.21 | down |
| ATVVYQGER (SEQ ID NO: 6) | Beta-2-glycoprotein 1 | P02749 (SEQ ID NO: 27) | APOH | 0.0032 | 0.0292 | 1.21 | down |
| AFIQLWAFDAVK (SEQ ID NO: 7) | Protein AMBP | P02760 (SEQ ID NO: 28) | AMBP | 0.0040 | 0.0313 | 1.18 | down |
| TVQAVLTVPK (SEQ ID NO: 8) | Pigment epithelium-derived factor | P36955 (SEQ ID NO: 29) | SERPINF1 | 0.0046 | 0.0313 | 1.16 | down |
| GSPAINVAVHVFR (SEQ ID NO: 9) | Transthyretin | P02766 (SEQ ID NO: 30) | TTR | 0.0070 | 0.0345 | 1.31 | down |
| AVVEVDESGTR (SEQ ID NO: 10) | Plasma serine protease inhibitor | P05154 (SEQ ID NO: 31) | SERPINA5 | 0.0070 | 0.0345 | 1.26 | down |

TABLE 2-continued

Significant Proteins Differently Expressed in AECOPD Compared to the Convalescent State

| Peptide | Protein Name | UniProt ID | Gene Symbol | P-value | FDR | Fold Change | Direction AECOPD Relative to Convalescence |
|---|---|---|---|---|---|---|---|
| GFVVAGPSR (SEQ ID NO: 11) | Complement component C6 | P13671 (SEQ ID NO: 32) | C6 | 0.0074 | 0.0345 | 1.01 | up |
| SVNDLYIQK (SEQ ID NO: 12) | Heparin cofactor 2 | P05546 (SEQ ID NO: 33) | SERPIND1 | 0.0075 | 0.0345 | 1.21 | down |
| VVEESELAR (SEQ ID NO: 13) | Complement component C9 | P02748 (SEQ ID NO: 34) | C9 | 0.0087 | 0.0367 | 1.12 | up |
| FLHVPDTFEGHFDGVPVISK (SEQ ID NO: 14) | Inter-alpha trypsin inhibitor heavy chain H2 | P19823 (SEQ ID NO: 35) | ITIH2 | 0.0113 | 0.0444 | 1.11 | down |
| AFVFPK (SEQ ID NO: 15) | C-reactive protein | P02741 (SEQ ID NO: 36) | CRP | 0.0124 | 0.0454 | 1.29 | up |
| DGYLFQLLR (SEQ ID NO: 16) | Histindine-rich glycoprotein | P04196 (SEQ ID NO: 37) | HRG | 0.0140 | 0.0475 | 1.08 | down |
| IQVYSR (SEQ ID NO: 17) | Beta-2-microglobulin | P61769 (SEQ ID NO: 38) | B2M | 0.0147 | 0.0475 | 1.19 | down |
| TGAQELLR (SEQ ID NO: 18) | Gelsolin | P06396 (SEQ ID NO: 39) | GSN | 0.0169 | 0.0517 | 1.04 | down |
| VSEGNHDIALIK (SEQ ID NO: 19) | Plasma kallirein | P03952 (SEQ ID NO: 40) | KLKB1 | 0.0264 | 0.0732 | 1.18 | down |
| FLNVLSPR (SEQ ID NO: 20) | Insulin-like growth factor-binding protein 3 | P19736 (SEQ ID NO: 41) | IGFBP3 | 0.0266 | 0.0732 | 1.21 | down |
| NFPSPVDAAFR (SEQ ID NO: 21) | Hemopexin | P02790 (SEQ ID NO: 42) | HPX | 0.0583 | 0.1526 | 1.19 | down |

TABLE 3

Biomarker Score Intercept and Specific Protein Weights
Biomarker score = $w_0 + w_1 \cdot protein_1 + w_2 \cdot protein_2 + \ldots + w_N \cdot protein_N$

| Intercept/Protein | w |
|---|---|
| Intercept ($w_0$) | −0.805 |
| Inter-alpha-trypsin inhibitor heavy chain H2 | −1.349 |
| Heparin cofactor 2 | −1.313 |
| Apolipoprotein A-I | −1.311 |
| Pigment epithelium-derived factor | −1.274 |
| Apolipoprotein C-II | −0.693 |
| Hemopexin | −0.407 |
| Beta-2-microglobulin | −0.297 |
| C-reactive protein | −0.143 |
| Gelsolin | −0.046 |
| Beta-2-glycoprotein 1 | −0.033 |
| Afamin | −0.021 |
| Histidine-rich glycoprotein | 0.001 |
| Retinol-binding protein 4 | 0.057 |
| Transthyretin | 0.261 |
| Apolipoprotein A-II | 0.494 |
| Complement component C9 | 0.872 |
| Protein AMBP | 0.947 |
| Complement component C6 | 2.591 |

Example 2

This example provides additional details regarding the methods used in Example 1.

Multiple Reaction Monitoring (MRM)-Mass Spectrometry (MS) Methods

In analytical chemistry, MS is able to identify the chemical composition of a sample by determining the mass-to-charge ratio of analyte ions. Further fragmentation of analyte ions by collision-induced dissociation (tandem MS) allows for protein identification and quantification. Stable isotopes standards (SIS) such as $^{13}C$, $^{15}N$, and $^{18}O$ are used as internal standards for the quantification step, in which the relative peak height or peak area of the analyte is compared to the stable isotope-labeled standard. MRM-MS achieves additional specificity, however, by monitoring a precursor ion and one of its collision-induced dissociation-generated product ions while still retaining the precursor and product ions of the stable isotope standard for quantification.

MRM Assay Development

Methods for MRM assay development have been previously described (1). First, to identify peptide sequences corresponding to the target protein, a BLAST (Basic Local Assignment Search Tool) search is performed with the goal peptide length between 5 and 25 amino acids. Up to 8 candidate peptides per protein are generated with the list further narrowed based on solubility and liquid chromatography (LC) retention time. SIS versions of the peptides selected are then made. SIS peptides are purified using high-performance LC. The concentration of the synthetic peptide is determined by acid hydrolysis and amino acid analysis. A final SIS mixture is generated by ensuring that the concentration of the SIS peptide is equivalent to the concentration in normal plasma.

Target Protein Candidates 230 peptides corresponding to 129 proteins were chosen for this study (see Table 4 for the full list). These were chosen based on a literature search and from a previous mass spectrometry analysis on COPD patients enrolled in the Evaluation of COPD Longitudinally to Identify Predict Surrogate Endpoints (ECLIPSE) cohort (GSK Study No. SCO104960, ClinicalTrials.gov NCT00292552) (2).

In the latter analysis, untargeted proteomics with 8-plex isobaric tags for relative and absolute quantification (iTRAQ) was performed on plasma from 300 subjects. iTRAQ analysis was performed in five phases: plasma depletion, trypsin digestion and iTRAQ labeling, high pH reversed phase fractionation, liquid chromatography (LC)-mass spectrometry (MS), and MS data analysis. The 14 most abundant plasma proteins were depleted using a custom-made 5 mL avian immunoaffinity column (Genway Biotech, San Diego, Calif., USA). Samples were digested with sequencing grade modified trypsin (Promega, Madison, Wis., USA) and labeled with iTRAQ reagents 113, 114, 115, 116, 117, 118, 119, and 121 according to the manufacturer's protocol (Applied Biosystems, Foster City, Calif., USA). Each iTRAQ set consisted of seven patient samples and one pool of the patient samples. The reference was randomly assigned to one of the iTRAQ labels. The study samples were randomized to the remaining seven iTRAQ labels by balancing phenotypes between the 43 iTRAQ sets.

High pH reversed phase fractionation was performed with an Agilent 1260 (Agilent, Calif., USA) equipped with an XBridge C18 BEH300 (Waters, Mass., USA) 250 mm×4.6 mm, 5 um, 300A HPLC column. The peptide solution was separated by on-line reversed phase liquid chromatography using a Thermo Scientific EASY-nanoLC II system with a reversed-phase pre-column Magic C-18AQ (Michrom BioResources Inc, Auburn, Calif.) and a reversed-phase nano-analytical column packed with Magic C-18AQ (Michrom BioResources Inc, Auburn, Calif.), at a flow rate of 300 nl/min. The chromatography system was coupled on-line to an LTQ Orbitrap Velos mass spectrometer equipped with a Nanospray Flex source (Thermo Fisher Scientific, Bremen, Germany). All data was analyzed using ProteinPilot™ Software 3.0 (AB SCIEX, Framingham, Mass.) and were searched against the Uniprot, version 072010, human database.

A total of 981 proteins were detected in at least one sample. Of these, 84 passed our pre-filtering rule, i.e. to be present in at least 75% of samples. We then compared subjects who had frequent exacerbation (at least 2 exacerbations per year for two years) with those who did not (no exacerbation for two years after blood collection), by means of limma, which identified 43 statistically significant proteins (see Table 4).

MRM-MS Assay

Solution and Sample Preparation

The plasma proteolytic digests were prepared manually as previously described (3). In brief, this involved denaturing, reducing, alkylating, and quenching 10-fold diluted plasma (30 µl) with 1% sodium deoxycholate (30 µL at 10%), 5 mM tris(2-carboxyethyl) phosphine (26.1 µL at 50 mM), 10 mM iodoacetamide (29 µL at 100 mM), and 10 mM dithiothreitol (29 µL at 100 mM; all prepared in 25 mM ammonium bicarbonate), respectively. The protein denaturation and Cys-Cys reduction steps occurred simultaneously for 30 min at 60° C., while Cys alkylation and iodoacetamide quenching followed sequentially for 30 min at 37° C. Thereafter, proteolysis was initiated with the addition of TPCK-treated trypsin (10.5 µL at 0.8 mg/mL; Worthington) at a 25:1 substrate:enzyme ratio. After overnight incubation at 37° C., proteolysis was arrested by the sequential addition of a chilled SIS peptide mixture (30 µL, fmol/µL for the samples) and a chilled FA solution (52.5 µL of 1.9%) to a digest aliquot (117.50 µL). The acid insoluble surfactant was then pelleted by centrifugation and 133.3 µL of each peptide supernatant was removed for solid phase extraction (Oasis HLB pElution Plate 30 µm). Following concentration, the eluates were lyophilized to dryness and rehydrated in 50 µL of 0.1% FA (final concentration: 1 µg/µL) for LC-MRM/MS analysis.

LC-MRM/MS Equipment and Conditions

Ten µL injections of the plasma digests were separated with a Zorbax Eclipse Plus RP-UHPLC column (2.1×150 mm, 1.8 µm particle diameter; Agilent) that was contained within a 1290 Infinity system (Agilent). Peptide separations were achieved at 0.4 mL/min over a 43 min run, via a multi-step LC gradient (1.5-81% mobile phase B; mobile phase compositions: A was 0.1% FA in $H_2O$ while B was 0.1% FA in ACN). The exact gradient was as follows (time in min, B): 0, 1.5%; 1.5, 6.3%; 16, 13.5%; 18, 13.77%; 33, 22.5%; 38, 40.5%; 39, 81%; 42.9, 81%; 43, 1.5%. The column and autosampler were maintained at 50° C. and 4° C., respectively. A post-column equilibration of 4 min was used after each sample analysis. Each individual sample was run in singleton.

The LC system was interfaced to a triple quadrupole mass spectrometer (Agilent 6490) via a standard-flow ESI source, operated in the positive ion mode. The general MRM acquisition parameters employed were as follows: 3.5 kV capillary voltage, 300 V nozzle voltage, 11 L/min sheath gas flow at a temperature of 250° C., 15 L/min drying gas flow at a temperature of 150° C., 30 psi nebulizer gas pressure, 380 V fragmentor voltage, 5 V cell accelerator potential, and unit mass resolution in the quadrupole mass analyzers. Specific LC-MS acquisition parameters were employed for optimal peptide ionization/fragmentation and scheduled MRM. Note that the peptide optimizations were empirically optimized previously by direct infusion of the purified SIS peptides.

Protein Quantitation

The MRM data was processed with MassHunter Quantitative Analysis software (Agilent), for verification of peak selection and integration.

REFERENCES

1. Cohen Freue G V, Borchers C H. Multiple reaction monitoring (MRM): principles and application to coronary artery disease. *Circ-Cardiovasc Gene* 2012; 5: 378.
2. Vestbo J, Anderson W, Coxson H O, Crim C, Dawber F, Edwards L, Hagan G, Knobil K, Lomas D A, MacNee W, Silverman E K, Tal-Singer R. Evaluation of COPD Longitudinally to Identify Predictive Surrogate End-points (ECLIPSE). *Eur Respir J* 2008; 31: 869-873.
3. Percy A J, Chambers A G, Yang J, Hardie D B, Borchers C H. Advances in multiplexed MRM-based protein biomarker quantitation toward clinical utility. *Biochim Biophys Acta* 2014; 1844: 917-926.

TABLE 4

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
| --- | --- | --- | --- |
| IDAVYEAPQEEK (SEQ ID NO: 43) | 72 kDa type IV collagenase | P08253 | MMP2 |
| IIGYTPDLDPETVDDAFAR (SEQ ID NO: 44) | 72 kDa type IV collagenase | P08253 | MMP2 |
| DSYVGDEAQSK (SEQ ID NO: 45) | Actin, alpha cardiac muscle 1 | P68032 | ACTC |
| SYELPDGQVITIGNER (SEQ ID NO: 46) | Actin, alpha cardiac muscle 1 | P68032 | ACTC |
| TSLGSDSSTQAK (SEQ ID NO: 47) | Adenylate cyclase type 9 | O60503 | ADCY9 |
| GDIGETGVPGAEGPR (SEQ ID NO: 48) | Adiponectin | Q15848 | ADIPO |
| IFYNQQNHYDGSTGK (SEQ ID NO: 49) | Adiponectin | Q15848 | ADIPO |
| IAPQLSTEELVSLGEK (SEQ ID NO: 50) | Afamin | P43652 | AFAM |
| LPNNVLQEK (SEQ ID NO: 51) | Afamin | P43652 | AFAM |
| AVLDVFEEGTEASAATAVK (SEQ ID NO: 52) | Alpha-1-antichymotrypsin | P01011 | AACT |
| NLAVSQVVHK (SEQ ID NO: 53) | Alpha-1-antichymotrypsin | P01011 | AACT |
| ITPNLAEFAFSLYR (SEQ ID NO: 54) | Alpha-1-antitrypsin | P01009 | A1AT |
| LSITGTYDLK (SEQ ID NO: 55) | Alpha-1-antitrypsin | P01009 | A1AT |
| ATWSGAVLAGR (SEQ ID NO: 56) | Alpha-1B-glycoprotein | P04217 | A1BG |
| LETPDFQLFK (SEQ ID NO: 7) | Alpha-1B-glycoprotein | P04217 | A1BG |
| DFLQSLK* (SEQ ID NO: 58) | Alpha-2-antiplasmin | P08697 | A2AP |
| LGNQEPGGQTALK* (SEQ ID NO: 59) | Alpha-2-antiplasmin | P08697 | A2AP |
| APHGPGLIYR* (SEQ ID NO: 60) | Alpha-2-HS-glycoprotein | P02765 | FETUA |
| HTLNQIDEVK* (SEQ ID NO: 61) | Alpha-2-HS-glycoprotein | P02765 | FETUA |
| LLIYAVLPTGDVIGDSAK (SEQ ID NO: 62) | Alpha-2-macroglobulin | P01023 | A2MG |
| TEHPFTVEEFVLPK (SEQ ID NO: 63) | Alpha-2-macroglobulin | P01023 | A2MG |
| ALQDQLVLVAAK* (SEQ ID NO: 64) | Angiotensinogen | P01019 | ANGT |
| DDLYVSDAFHK* (SEQ ID NO: 65) | Antithrombin-III | P01008 | ANT3 |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
|---|---|---|---|
| FATTFYQHLADSK* (SEQ ID NO: 66) | Antithrombin-III | P01008 | ANT3 |
| ATEHLSTLSEK (SEQ ID NO: 67) | Apolipoprotein A-I | P02647 | APOA1 |
| SPELQAEAK (SEQ ID NO: 68) | Apolipoprotein A-II | P02652 | APOA2 |
| SLAPYAQDTQEK (SEQ ID NO: 69) | Apolipoprotein A-IV | P06727 | APOA4 |
| FPEVDVLTK (SEQ ID NO: 70) | Apolipoprotein B-100 | P04114 | APOB |
| ILGEELGFASLHDLQLLGK (SEQ ID NO: 71) | Apolipoprotein B-100 | P04114 | APOB |
| TAAQNLYEK* (SEQ ID NO: 72) | Apolipoprotein C-II | P02655 | APOC2 |
| TYLPAVDEK* (SEQ ID NO: 73) | Apolipoprotein C-II | P02655 | APOC2 |
| FSEFWDLDPEVR (SEQ ID NO: 74) | Apolipoprotein C-III | P02656 | APOC3 |
| GWVTDGFSSLK (SEQ ID NO: 75) | Apolipoprotein C-III | P02656 | APOC3 |
| VTEPISAESGEQVER (SEQ ID NO: 76) | Apolipoprotein L1 | O14791 | APOL1 |
| WWTQAQAHDLVIK (SEQ ID NO: 77) | Apolipoprotein L1 | O14791 | APOL1 |
| FVTVQTISGTGALR (SEQ ID NO: 78) | Aspartate aminotransferase, mitochondrial | P00505 | AATM |
| ATVVYQGER (SEQ ID NO: 79) | Beta-2-glycoprotein 1 | P02749 | APOH |
| PDNGFVNYPAKPTLYYK (SEQ ID NO: 80) | Beta-2-glycoprotein 1 | P02749 | APOH |
| IQVYSR (SEQ ID NO: 81) | Beta-2-microglobulin | P61769 | B2MG |
| VNHVTLSQPK (SEQ ID NO: 82) | Beta-2-microglobulin | P61769 | B2MG |
| ALEQDLPVNIK* (SEQ ID NO: 83) | Beta-Ala-His dipeptidase | Q96KN2 | CNDP1 |
| SVVLIPLGAVDDGEHSQNEK* (SEQ ID NO: 84) | Beta-Ala-His dipeptidase | Q96KN2 | CNDP1 |
| AFVFPK (SEQ ID NO: 85) | C-reactive protein | P02741 | CRP |
| ESDTSYVSLK (SEQ ID NO: 86) | C-reactive protein | P02741 | CRP |
| EDVYVVGTVLR* (SEQ ID NO: 87) | C4b-binding protein alpha chain | P04003 | C4BPA |
| LSLEIEQLELQR* (SEQ ID NO: 88) | C4b-binding protein alpha chain | P04003 | C4BPA |
| YEIVVEAR (SEQ ID NO: 89) | Cadherin-5 | P33151 | CADH5 |
| YTFVVPEDTR (SEQ ID NO: 90) | Cadherin-5 | P33151 | CADH5 |
| ESISVSSEQLAQFR (SEQ ID NO: 91) | Carbonic anhydrase 1 | P00915 | CAH1 |
| VLDALQAIK (SEQ ID NO: 92) | Carbonic anhydrase 1 | P00915 | CAH1 |
| EALIQFLEQVHQGIK* (SEQ ID NO: 93) | Carboxypeptidase N catalytic chain | P15169 | CBPN |
| IVQLIQDTR* (SEQ ID NO: 94) | Carboxypeptidase N catalytic chain | P15169 | CBPN |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
|---|---|---|---|
| LVGGLHR (SEQ ID NO: 95) | CD5 antigen-like | O43866 | CD5L |
| GAYPLSIEPIGVR (SEQ ID NO: 96) | Ceruloplasmin | P00450 | CERU |
| IYHSHIDAPK (SEQ ID NO: 97) | Ceruloplasmin | P00450 | CERU |
| ELDESLQVAER* (SEQ ID NO: 98) | Clusterin | P10909 | CLUS |
| EPQDTYHYLPFSLPHR* (SEQ ID NO: 99) | Clusterin | P10909 | CLUS |
| LANLTQGEDQYYLR* (SEQ ID NO: 100) | Clusterin | P10909 | CLUS |
| SALVLQYLR* (SEQ ID NO: 101) | Coagulation factor IX | P00740 | FA9 |
| VSVSQTSK* (SEQ ID NO: 102) | Coagulation factor IX | P00740 | FA9 |
| AEVDDVIQVR (SEQ ID NO: 103) | Coagulation factor V | P12259 | FAS |
| VAQVIIPSTYVPGTTNHDIALLR (SEQ ID NO: 104) | Coagulation factor VII | P08709 | FA7 |
| VSQYIEWLQK (SEQ ID NO: 105) | Coagulation factor VII | P08709 | FA7 |
| NLFLTNLDNLHENNTHNQEK (SEQ ID NO: 106) | Coagulation factor VIII | P00451 | FA8 |
| ETYDFDIAVLR* (SEQ ID NO: 107) | Coagulation factor X | P00742 | FA10 |
| TGIVSGFGR* (SEQ ID NO: 108) | Coagulation factor X | P00742 | FA10 |
| LHEAFSPVSYQHDLALLR (SEQ ID NO: 109) | Coagulation factor XII | P00748 | FA12 |
| VVGGLVALR (SEQ ID NO: 110) | Coagulation factor XII | P00748 | FA12 |
| AVPPNNSNAAEDDPTVEQGVVPR (SEQ ID NO: 111) | Coagulation factor XIII A chain | P00488 | F13A |
| SIVLTIPEIIIK (SEQ ID NO: 112) | Coagulation factor XIII A chain | P00488 | F13A |
| IQTHSTTYR (SEQ ID NO: 113) | Coagulation factor XIII B chain | P05160 | F13B |
| LIENGYFHPVK (SEQ ID NO: 114) | Coagulation factor XIII B chain | P05160 | F13B |
| PAFSAIR* (SEQ ID NO: 115) | Complement C1q subcomponent subunit A | P02745 | C1QA |
| SLGFCDTTNK* (SEQ ID NO: 116) | Complement C1q subcomponent subunit A | P02745 | C1QA |
| FQSVFTVTR* (SEQ ID NO: 117) | Complement C1q subcomponent subunit C | P02747 | C1QC |
| TNQVNSGGVLLR* (SEQ ID NO: 118) | Complement C1q subcomponent subunit C | P02747 | C1QC |
| GLTLHLK* (SEQ ID NO: 119) | Complement C1r subcomponent | P00736 | C1R |
| GYGFYTK* (SEQ ID NO: 120) | Complement C1r subcomponent | P00736 | C1R |
| SYPPDLR* (SEQ ID NO: 121) | Complement C1r subcomponent | P00736 | C1R |
| TLDEFTIIQNLQPQYQFR* (SEQ ID NO: 122) | Complement C1r subcomponent | P00736 | C1R |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
| --- | --- | --- | --- |
| VSVHPDYR* (SEQ ID NO: 123) | Complement C1r subcomponent | P00736 | C1R |
| SDFSNEER* (SEQ ID NO: 124) | Complement C1s subcomponent | P09871 | C1S |
| TNFDNDIALVR* (SEQ ID NO: 125) | Complement C1s subcomponent | P09871 | C1S |
| DHENELLNK (SEQ ID NO: 126) | Complement C2 | P06681 | CO2 |
| HAFILQDTK (SEQ ID NO: 127) | Complement C2 | P06681 | CO2 |
| TGLQEVEVK (SEQ ID NO: 128) | Complement C3 | P01024 | CO3 |
| DHAVDLIQK (SEQ ID NO: 129) | Complement C4-A | P0C0L4 | CO4A |
| VGDTLNLNLR (SEQ ID NO: 130) | Complement C4-A | P0C0L4 | CO4A |
| VLSLAQEQVGGSPEK (SEQ ID NO: 131) | Complement C4-A | P0C0L4 | CO4A |
| GFVVAGPSR (SEQ ID NO: 132) | Complement component C6 | P13671 | CO6 |
| ELSHLPSLYDYSAYR (SEQ ID NO: 133) | Complement component C7 | P10643 | CO7 |
| LIDQYGTHYLQSGSLGGEYR (SEQ ID NO: 134) | Complement component C7 | P10643 | CO7 |
| SYTSHTNEIHK (SEQ ID NO: 135) | Complement component C7 | P10643 | CO7 |
| SLPVSDSVLSGFEQR (SEQ ID NO: 136) | Complement component C8 gamma chain | P07360 | CO8G |
| VQEAHLTEDQIFYFPK (SEQ ID NO: 137) | Complement component C8 gamma chain | P07360 | CO8G |
| LSPIYNLVPVK (SEQ ID NO: 138) | Complement component C9 | P02748 | CO9 |
| VVEESELAR (SEQ ID NO: 139) | Complement component C9 | P02748 | CO9 |
| EELLPAQDIK (SEQ ID NO: 140) | Complement factor B | P00751 | CFAB |
| THHDGAITER (SEQ ID NO: 141) | Complement factor D | P00746 | CFAD |
| SSNLIILEEHLK* (SEQ ID NO: 142) | Complement factor H | P08603 | CFAH |
| SSQESYAHGTK* (SEQ ID NO: 143) | Complement factor H | P08603 | CFAH |
| HGNTDSEGIVEVK* (SEQ ID NO: 144) | Complement factor I | P05156 | CFAI |
| IVIEYVDR* (SEQ ID NO: 145) | Complement factor I | P05156 | CFAI |
| AQLLQGLGFNLTER (SEQ ID NO: 146) | Corticosteroid-binding globulin | P08185 | CBG |
| HLVALSPK (SEQ ID NO: 147) | Corticosteroid-binding globulin | P08185 | CBG |
| TLDEILQEK (SEQ ID NO: 148) | Cyclin-dependent kinase 11A | Q9UQ88 | CD11A |
| TSNLLLSHAGILK (SEQ ID NO: 149) | Cyclin-dependent kinase 11A | Q9UQ88 | CD11A |
| ALDFAVGEYNK (SEQ ID NO: 150) | Cystatin-C | P01034 | CYTC |
| ALQVVR (SEQ ID NO: 151) | Cystatin-C | P01034 | CYTC |
| ELPSLQHPNEQK (SEQ ID NO: 152) | Extracellular matrix protein 1 | Q16610 | ECM1 |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
| --- | --- | --- | --- |
| NVALVSGDTENAK (SEQ ID NO: 153) | Extracellular matrix protein 1 | Q16610 | ECM1 |
| LVVLPFPK* (SEQ ID NO: 154) | Fetuin-B | Q9UGM5 | FETUB |
| VNDAQEYR* (SEQ ID NO: 155) | Fetuin-B | Q9UGM5 | FETUB |
| AHYGGFTVQNEANK (SEQ ID NO: 156) | Fibrinogen beta chain | P02675 | FIBB |
| QGFGNVATNTDGK (SEQ ID NO: 157) | Fibrinogen beta chain | P02675 | FIBB |
| YEASILTHDSSIR (SEQ ID NO: 158) | Fibrinogen gamma chain | P02679 | FIBG |
| HTSVQTTSSGSGPFTDVR* (SEQ ID NO: 159) | Fibronectin | P02751 | FINC |
| SSPVVIDASTAIDAPSNLR* (SEQ ID NO: 160) | Fibronectin | P02751 | FINC |
| GYHLNEEGTR (SEQ ID NO: 161) | Fibulin-1 | P23142 | FBLN1 |
| SQETGDLDVGGLQETDK (SEQ ID NO: 162) | Fibulin-1 | P23142 | FBLN1 |
| TGYYFDGISR (SEQ ID NO: 163) | Fibulin-1 | P23142 | FBLN1 |
| TGAQELLR* (SEQ ID NO: 164) | Gelsolin | P06396 | GELS |
| PGGGFVPNFQLFEK* (SEQ ID NO: 165) | Glutathione peroxidase 3 | P22352 | GPX3 |
| VGYVSGWGR (SEQ ID NO: 166) | Haptoglobin | P00738 | HPT |
| TYFPHFDLSHGSAQVK (SEQ ID NO: 167) | Hemoglobin subunit alpha | P69905 | HBA |
| VGAHAGEYGAEALER (SEQ ID NO: 168) | Hemoglobin subunit alpha | P69905 | HBA |
| LYLVQGTQVYVFLTK* (SEQ ID NO: 169) | Hemopexin | P02790 | HEMO |
| NFPSPVDAAFR* (SEQ ID NO: 170) | Hemopexin | P02790 | HEMO |
| GETHEQVHSILHFK* (SEQ ID NO: 171) | Heparin cofactor 2 | P05546 | HEP2 |
| NYNLVESLK* (SEQ ID NO: 172) | Heparin cofactor 2 | P05546 | HEP2 |
| SVNDLYIQK* (SEQ ID NO: 173) | Heparin cofactor 2 | P05546 | HEP2 |
| SPLNDFQVLR (SEQ ID NO: 174) | Hepatocyte growth factor-like protein | P26927 | HGFL |
| DGYLFQLLR* (SEQ ID NO: 175) | Histidine-rich glycoprotein | P04196 | HRG |
| FLNVLSPR (SEQ ID NO: 176) | Insulin-like growth factor-binding protein 3 | P17936 | IBP3 |
| YGQPLPGYTTK (SEQ ID NO: 177) | Insulin-like growth actor-binding protein 3 | P17936 | IBP3 |
| NLIAAVAPGAFLGLK* (SEQ ID NO: 178) | Insulin-like growth factor-binding protein complex acid labile subunit | P35858 | ALS |
| VAGLLEDTFPGLLGLR* (SEQ ID NO: 179) | Insulin-like growth factor-binding protein complex acid labile subunit | P35858 | ALS |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
|---|---|---|---|
| ETAVDGELVVLYDVK* (SEQ ID NO: 180) | Inter-alpha-trypsin inhibitor heavy chain H2 | P19823 | ITIH2 |
| FLHVPDTFEGHFDGVPVISK* (SEQ ID NO: 181) | Inter-alpha-trypsin inhibitor heavy chain H2 | P19823 | ITIH2 |
| SPEQQETVLDGNLIIR (SEQ ID NO: 182) | Inter-alpha-trypsin inhibitor heavy chain H4 | Q14624 | ITIH4 |
| ISTLSCENK (SEQ ID NO: 183) | Interleukin-18 | Q14116 | IL18 |
| IITGLLEFEVYLEYLQNR (SEQ ID NO: 184) | Interleukin-6 | P05231 | IL6 |
| VGSALFLSHNLK* (SEQ ID NO: 185) | Kallistatin | P29622 | KAIN |
| DIPTNSPELEETLTHTITK (SEQ ID NO: 186) | Kininogen-1 | P01042 | KNG1 |
| TVGSDTFYSFK (SEQ ID NO: 187) | Kininogen-1 | P01042 | KNG1 |
| DLLHVLAFSK (SEQ ID NO: 188) | Leptin | P41159 | LEP |
| YSENSTTVIR (SEQ ID NO: 189) | Leptin receptor | P48357 | LEPR |
| GLQYAAQEGLLALQSELLR (SEQ ID NO: 190) | Lipopolysaccharide-binding protein | P18428 | LBP |
| ITLPDFTGDLR (SEQ ID NO: 191) | Lipopolysaccharide-binding protein | P18428 | LBP |
| LGSFEGLVNLTFIHLQHNR* (SEQ ID NO: 192) (SEQ ID NO: !) | Lumican | P51884 | LUM |
| LPSGLPVSLLTLYLDNNK* (SEQ ID NO: 193) | Lumican | P51884 | LUM |
| SLEDLQLTHNK* (SEQ ID NO: 194) | Lumican | P51884 | LUM |
| SLEYLDLSFNQIAR* (SEQ ID NO: 195) | Lumican | P51884 | LUM |
| FNSVPLTDTGHER (SEQ ID NO: 196) | Macrophage colony-stimulating factor 1 | P09603 | CSF1 |
| APGELEHGLITFSTR (SEQ ID NO: 197) | Mannan-binding lectin serine protease 1 | P48740 | MASP1 |
| TEGQFVDLTGNR SEQ ID NO: 198) | Mannose-binding protein C | P11226 | MBL2 |
| LGLGADVAQVTGALR (SEQ ID NO: 199) | Matrix metalloproteinase-9 | P14780 | MMP9 |
| SLGPALLLLQK (SEQ ID NO: 200) | Matrix metalloproteinase-9 | P14780 | MMP9 |
| FVGTPEVNQTTLYQR (SEQ ID NO: 201) | Metalloproteinase inhibitor 1 | P01033 | TIMP1 |
| GFQALGDAADIR (SEQ ID NO: 202) | Metalloproteinase inhibitor 1 | P01033 | TIMP1 |
| ELTLEDLK (SEQ ID NO: 203) | Monocyte differentiation antigen CD14 | P08571 | CD14 |
| FPAIQNLALR (SEQ ID NO: 204) | Monocyte differentiation antigen CD14 | P08571 | CD14 |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
|---|---|---|---|
| STLSVGVSGTLVLLQGAR (SEQ ID NO: 205) | Monocyte differentiation antigen CD14 | P08571 | CD14 |
| IANVFTNAFR (SEQ ID NO: 206) | Myeloperoxidase | P05164 | PERM |
| VVLEGGIDPILR (SEQ ID NO: 207) | Myeloperoxidase | P05164 | PERM |
| AAPAPAPPPEPERPK (SEQ ID NO: 208) | Myosin light chain 3 | P08590 | MYL3 |
| PSLSHLLSQYYGAGVAR* (SEQ ID NO: 209) | N-acetylmuramoyl-Lalanine amidase | Q96PD5 | PGRP2 |
| TDCPGDALFDLLR* (SEQ ID NO: 210) | N-acetylmuramoyl-L-alanine amidase | Q96PD5 | PGRP2 |
| ALPAVETQAPTSLATK (SEQ ID NO: 211) | Peptidase inhibitor 16 | Q6UXB8 | PI16 |
| ATAVVDGAFK (SEQ ID NO: 212) | Peroxiredoxin-2 | P32119 | PRDX2 |
| GLFIIDGK (SEQ ID NO: 213) | Peroxiredoxin-2 | P32119 | PRDX2 |
| SSGLVSNAPGVQIR (SEQ ID NO: 214) | Phosphatidylcholine-sterol acyltransferase | P04180 | LCAT |
| AVEPQLQEEER (SEQ ID NO: 215) | Phospholipid transfer protein | P55058 | PLTP |
| FLEQELETITIPDLR (SEQ ID NO: 216) | Phospholipid transfer protein | P55058 | PLTP |
| TSLEDFYLDEER* (SEQ ID NO: 217) | Pigment epithelium-derived factor | P36955 | PEDF |
| IVQAVLTVPK* (SEQ ID NO: 218) | Pigment epithelium-derived factor | P36955 | PEDF |
| VSEGNHDIALIK (SEQ ID NO: 219) | Plasma kallikrein | P03952 | KLKB1 |
| LLDSLPSDTR (SEQ ID NO: 220) | Plasma protease C1 inhibitor | P05155 | IC1 |
| AVVEVDESGTR (SEQ ID NO: 221) | Plasma serine protease inhibitor | P05154 | IPSP |
| FSIEGSYQLEK (SEQ ID NO: 222) | Plasma serine protease inhibitor | P05154 | IPSP |
| VILGAHQEVNLEPHVQEIEVSR* (SEQ ID NO: 223) | Plasminogen | P00747 | PLMN |
| DEISTTDAIFVQR* (SEQ ID NO: 224) | Plasminogen activator inhibitor 1 | P05121 | PAM |
| FSLETEVDLR* (SEQ ID NO: 225) | Plasminogen activator inhibitor 1 | P05121 | PAI1 |
| AFIQLWAFDAVK* (SEQ ID NO: 226) | Protein AMBP | P02760 | AMBP |
| ETLLQDFR* (SEQ ID NO: 227) | Protein AMBP | P02760 | AMBP |
| HHGPTITAK* (SEQ ID NO: 228) | Protein AMBP | P02760 | AMBP |
| ETSNFGFSLLR (SEQ ID NO: 229) | Protein Z-dependent protease inhibitor | Q9UK55 | ZPI |
| LFDEINPETK (SEQ ID NO: 230) | Protein Z-dependent protease inhibitor | Q9UK55 | ZPI |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
|---|---|---|---|
| DQYYNIDVPSR (SEQ ID NO: 231) | Proteoglycan 4 | Q92954 | PRG4 |
| GFGGLTGQIVAALSTAK (SEQ ID NO: 232) | Proteoglycan 4 | Q92954 | PRG4 |
| ELLESYIDGR* (SEQ ID NO: 233) | Prothrombin | P00734 | THRB |
| ETAASLLQAGYK* (SEQ ID NO: 234) | Prothrombin | P00734 | THRB |
| YWGVASFLQK* (SEQ ID NO: 235) | Retinol-binding protein 4 | P02753 | RET4 |
| AEFAEVSK (SEQ ID NO: 236) | Serum albumin | P02768 | ALBU |
| LVNEVTEFAK (SEQ ID NO: 237) | Serum albumin | P02768 | ALBU |
| FRPDGLPK (SEQ ID NO: 238) | Serum amyloid A-4 protein | P35542 | SAA4 |
| GPGGVWAAK (SEQ ID NO: 239) | Serum amyloid A-4 protein | P35542 | SAA4 |
| AYSLFSYNTQGR (SEQ ID NO: 240) | Serum amyloid P-component | P02743 | SAMP |
| IQNILTEEPK* (SEQ ID NO: 241) | Serum paraoxonase/arylesterase 1 | P27169 | PON1 |
| SFNPNSPGK* (SEQ ID NO: 242) | Serum paraoxonase/arylesterase 1 | P27169 | PON1 |
| IALGGLLFPASNLR (SEQ ID NO: 243) | Sex hormone-binding globulin | P04278 | SHBG |
| VVLSQGSK (SEQ ID NO: 244) | Sex hormone-binding globulin | P04278 | SHBG |
| GGTLGTPQTGSENDALYEYLR* (SEQ ID NO: 245) | Tetranectin | P05452 | TETN |
| AVLHIGEK* (SEQ ID NO: 246) | Thyroxine-binding globulin | P05543 | THBG |
| FSISATYDLGATLLK* (SEQ ID NO: 247) | Thyroxine-binding globulin | P05543 | THBG |
| TLYETEVFSTDFSNISAAK* (SEQ ID NO: 248) | Thyroxine-binding globulin | P05543 | THBG |
| IPVVLPEDEGIYTAFASNIK (SEQ ID NO: 249) | Titin | Q8WZ42 | TITIN |
| VAGESAEPEPEPEADYYAK (SEQ ID NO: 250) | Transforming growth factor beta-1 | P01137 | TGFB1 |
| VEQHVELYQK (SEQ ID NO: 251) | Transforming growth factor beta-1 | P01137 | TGFB1 |
| AADDTVVEPFASGK* (SEQ ID NO: 252) | Transthyretin | P02766 | TTHY |
| GSPAINVAVHVFR* (SEQ ID NO: 253) | Transthyretin | P02766 | TTHY |
| LHIDEMDSVPTVR (SEQ ID NO: 254) | Vascular cell adhesion protein 1 | P19320 | VCAM1 |
| LAGLGLQQLDEGLFSR (SEQ ID NO: 255) | Vasorin | Q6EMK4 | VASN |
| SLTLGIEPVSPTSLR (SEQ ID NO: 256) | Vasorin | Q6EMK4 | VASN |
| YLQGSSVQLR (SEQ ID NO: 257) | Vasorin | Q6EMK4 | VASN |
| ELPEHTVK* (SEQ ID NO: 258) | Vitamin D-binding protein | P02774 | VTDB |

TABLE 4-continued

Peptides and Corresponding Proteins
*Denotes peptides discovered from a previous untargeted iTRAQ mass spectrometry analysis performed on the ECLIPSE cohort.

| Peptide | Protein Name | Accession Number | Gene Symbol |
|---|---|---|---|
| THLPEVFLSK* (SEQ ID NO: 259) | Vitamin D-binding protein | P02774 | VTDB |
| LGEYDLR (SEQ ID NO: 260) | Vitamin K-dependent protein C | P04070 | PROC |
| TFVLNFIK (SEQ ID NO: 261) | Vitamin K-dependent protein C | P04070 | PROC |
| YLDWIHGHIR (SEQ ID NO: 262) | Vitamin K-dependent protein C | P04070 | PROC |
| SFQTGLFTAAR* (SEQ ID NO: 263) | Vitamin K-dependent protein S | P07225 | PROS |
| VYFAGFPR* (SEQ ID NO: 264) | Vitamin K-dependent protein S | P07225 | PROS |
| DFAEHLLIPR (SEQ ID NO: 265) | Vitamin K-dependent protein Z | P22891 | PROZ |
| ENFVLTTAK (SEQ ID NO: 266) | Vitamin K-dependent protein Z | P22891 | PROZ |
| DVVVGIEGPIDAAFTR* (SEQ ID NO: 267) | Vitronectin | P04004 | VTNC |
| FEDGVLDPDYPR* (SEQ ID NO: 268) | Vitronectin | P04004 | VTNC |
| IGWPNAPILIQDFETLPR (SEQ ID NO: 269) | von Willebrand factor | P04275 | VWF |
| ILAGPAGDSNVVK (SEQ ID NO: 270) | von Willebrand factor | P04275 | VWF |
| AGEVQEPELR* (SEQ ID NO: 271) | Zinc-alpha-2-glycoprotein | P25311 | ZA2G |
| YSLTYIYTGLSK* (SEQ ID NO: 272) | Zinc-alpha-2-glycoprotein | P25311 | ZA2G |

Example 3

This example describes the further development of a panel of protein biomarkers that can distinguish AECOPD from a convalescent state.

Introduction

In patients with chronic obstructive pulmonary disease (COPD), fixed airflow limitation often results in symptoms such as dyspnea, cough, and sputum production. The periodic worsening of these symptoms is known as an acute exacerbation (AECOPD), an event that can have lasting detrimental effects on lung function (when experienced repeatedly),[1] respiratory-related quality of life,[2] and mortality.[3] Economically, the impact of AECOPD is profound, as annual AECOPD-related costs in the United States alone amount to $30 billion.[4] The diagnosis of an AECOPD, largely made on the basis of clinical gestalt, is fraught with uncertainty.[5] In recent years, the search for a blood-based biomarker to distinguish AECOPD from states of relative clinical stability has focused on common inflammatory markers such as plasma C-reactive protein (CRP) [6] and serum amyloid protein.[7] Such a restrictive strategy, however, overlooks the fundamental heterogeneity of AECOPD in which respiratory viruses, bacterial infection, air pollution, and cardiac dysfunction can all interact through distinct pathways to initiate an event. [8-11]

A comprehensive approach to biomarkers could potentially revolutionize the diagnosis and management of AECOPD, ideally revealing a panel of biomarkers that could accurately identify AECOPD early in the clinical course to enable intervention. Shotgun proteomics, requiring no a priori hypothesis, offers an unbiased platform to detect biomarker candidates, yet is limited by low-throughput, poor accuracy, and suboptimal quantitation. On the other hand, multiple reaction monitoring-mass spectrometry (MRM-MS) offers an inexpensive, high-throughput platform with the ability to quantify hundreds of targeted proteins based on precursor-product ion pairs,[12] and in 2012 was selected by Nature as "Method of the Year".[13] It has since been employed to verify and validate biomarker panels in cystic fibrosis and lung cancer among many other diseases.[14 15] To date, MRM-MS has not been applied to the problem of COPD and AECOPD, but may provide an exceptional opportunity to discover new clinically applicable biomarkers. This study is the first of its kind to employ MRM-MS to identify biomarkers distinguishing AECOPD from periods of clinical stability.

Methods

Study Populations. Biomarker discovery involved 72 patients from the previously described and studied cohort evaluating the use of etanercept or prednisone in the treatment of AECOPD (TNF-α, Clinicaltrials.gov identifier: NCT00789997).[16] Inclusion criteria for the TNF-α cohort were age >35 years, an AECOPD presenting to a physician or emergency department, FEV1≤70% predicted, FEV1/forced vital capacity (FVC)≤70%, and ≥10 pack-years smoking history. AECOPD was diagnosed when two of the following three criteria were met: increased dyspnea, sputum volume, and sputum purulence. Plasma samples used in this analysis were obtained at baseline and at day 14. The baseline sample was considered to indicate an AECOPD whereas the day 14 sample was used to indicate a convalescent state.

Biomarkers were confirmed in patients from two other AECOPD cohorts. The first replication cohort was a randomized controlled trial evaluating the use of zileuton in the treatment of AECOPD (LEUKO, n=37, Clinicaltrials.gov identifier: NCT00493974).[17] Briefly, inclusion criteria were age >45 years, admission to the hospital for AECOPD, >10 pack-years smoking history, and forced expiratory volume in 1 second (FEV1)<60% predicted. An AECOPD was defined as an acute increase in dyspnea, sputum volume, and/or sputum purulence without an alternative explanation. Plasma samples used in this analysis were collected at the beginning of the hospitalisation period and at day 30. We considered the initial sample collection at hospitalisation to indicate an AECOPD whereas the day 30 samples were used to indicate a convalescent state.

The second replication cohort (Rapid Transition Program or RTP, n=109) included prospectively enrolled patients admitted to two large teaching hospitals for AECOPD for the primary purpose of biomarker discovery to diagnose and track AECOPD. For the RTP cohort, subjects had to be admitted to the hospital with an AECOPD as determined by general internists or pulmonologists. Blood samples were collected at the time of admission to the hospital and at either day 30 or 90 following admission (both time points indicating the convalescent state).

Sample Collection. LEUKO and RTP blood samples were collected in lavender-top EDTA tubes with the plasma layer isolated following centrifugation and stored at −80° C. Blood samples from the TNF-α cohort were collected in P100 tubes (BD, Franklin Lake, N.J.) and stored on ice until processing. Blood was spun down within two hours of collection and plasma was stored at −80° C. until selected for proteomic analysis. Patient plasma samples were analysed using MRM-MS at the UVic Genome BC Proteomics Centre (Victoria, BC, Canada) according to methods described previously.[18] There were 230 peptides measured corresponding to 129 proteins, selected on the basis of both a literature search and from a previous untargeted iTRAQ mass spectrometry analysis on COPD patients. These proteins broadly represented inflammatory cytokines, cell homeostasis, coagulation, lipid metabolism, and immune response.

Statistical Analyses. Statistical analysis was performed using R (www.r-project.org) and Bioconductor (www.bioconductor.org). Pre-processing of the MRM-MS data involved several steps. All peptides that had more than 25% missing values (signifying the peptide was below the limit of detection) across all samples or that did not pass quality control metrics were removed. Remaining missing values were imputed with a value equal to half of the minimum peptide level, for each peptide separately. Relative response of peptide abundance to stable isotopically-labeled peptide abundance was log-base 2 transformed and summarised at the protein level to create protein level data.

Proteins were analysed for differential expression between the patients' exacerbation and convalescent samples, using limma (limma Bioconductor package). A false discovery rate (FDR)<0.01 and fold change >1.2 were used as the criteria for selecting candidate proteins. An elastic net logistic regression model [19] (glmnet R package) was applied to the list of candidate proteins to build a classifier or biomarker score, which is the aggregation of the weighted contributions (linear predictors, denoted here as $w_N$, $w_i$) of each protein in the model to the presence of AECOPD:

$$\text{Biomarker score} = w_0 + w_1 * \text{protein}_1 + w_2 * \text{protein}_2 + \ldots + w_N * \text{protein}_N$$

The performance characteristics of this biomarker panel were estimated using leave-pair-out cross-validation (LPOCV) in the discovery cohort. The LPOCV-based biomarker scores were also used to select decision thresholds, chosen to detect convalescence or exacerbation with at least 90%, and to optimize Youden's index given this requirement. The classification model and decision thresholds obtained from TNF-α were applied to the LEUKO and RTP cohorts for external replication. A summary of the overall workflow is shown in FIG. 1.

Results

Cohort Demographics.

The demographic characteristics comparing the TNF-α, LEUKO, and RTP cohorts are those shown in Table 5.

TABLE 5

Demographic Data for TNF-α, LEUKO, and RTP Cohorts

| Characteristic | TNF-α (n = 72) | LEUKO (n = 37) | RTP (n = 109) | p-value* |
|---|---|---|---|---|
| Age (years) | 67.06 ± 9.28 | 62.11 ± 8.19 | 67.79 ± 10.54 | 0.009 |
| Male (%) | 37.04 | 56.76 | 63.30 | 0.001 |
| BMI (kg/m²) | 26.56 ± 7.14 | 27.04 ± 5.65 | 27.37 ± 6.88 | 0.852 |
| Caucasian (%) | 98.77 | 59.46 | 82.41 | <0.001 |
| Smoking Status | | | | <0.001 |
| Current (%) | 23.46 | 29.73 | 52.29 | |
| Former (%) | 70.37 | 70.27 | 33.94 | |
| Smoking pack-years | 47.85 ± 28.23 | 47.86 ± 28.02 | 53.39 ± 36.05 | 0.476 |
| FEV1 (L) | 0.94 ± 0.47 | 1.00 ± 0.62 | 1.66 ± 0.85 | <0.001 |
| FEV1 (% Predicted) | 34.41 ± 13.87 | 31.92 ± 15.27 | 57.19 ± 20.11 | <0.001 |
| FVC (L) | 2.33 ± 1.00 | 2.35 ± 0.93 | 2.98 ± 1.16 | 0.007 |
| FVC (% Predicted) | 66.65 ± 20.88 | 56.9 ± 15.7 | 81.28 ± 19.28 | 0.001 |
| FEV1/FVC (%) | 40.78 ± 13.14 | 41.92 ± 11.61 | 55.52 ± 13.82 | <0.001 |
| Bronchodilator Use (%) | 100 | 94.59 | 95.42 | 0.134 |
| Inhaled Corticosteroid Use (%) | 95.00 | 67.57 | 44.95 | <0.001 |

Values are reported as mean ± standard deviation or percentages.
Abbreviations: BMI — body mass index;
FEV1 — forced expiratory volume in 1 second;
FVC — forced vital capacity
*P-values were generated using an ANOVA test for continuous variables and chi-quare tests for categorical variables.

Patients in the RTP cohort had better lung function than patients in the LEUKO and TNF-α cohorts, but were also more likely to be current rather than former smokers. Fewer patients in the RTP cohort were also being treated with inhaled corticosteroids. The majority of patients in all three cohorts were being treated with bronchodilators.

Biomarker Panel Performance.

After the removal of peptides with more than 250% missing values across all samples and those that failed quality control metrics, the MRM-MS data consisted of 55 proteins. Of these, seven showed differential levels between exacerbation and convalescent time points at a FDR ≤0.01, with a fold change >1.2 (Table 6).

TABLE 6

Significant Proteins Differentially Expressed in AECOPD Compared to the Convalescent State

| Peptide | Protein Name | UniProt ID | Gene Symbol | p-value | FDR | Fold Change | Direction AECOPD Relative to Convalescence |
|---|---|---|---|---|---|---|---|
| SLAPYAQDTQEK (SEQ ID NO: 69) | Apolipoprotein A-IV | P06727 | APOA4 | 0.000 | 0.000 | 1.33 | Down |
| VVEESELAR (SEQ ID NO: 13) | Complement component C9 | P02748 | C9 | 0.000 | 0.000 | 1.23 | Up |
| SSPVVIDASTAIDAPSNLR (SEQ ID NO: 160) | Fibronectin | P02751 | FN1 | 0.000 | 0.000 | 1.23 | Down |
| TAAQNLYEK (SEQ ID NO: 1) | Apolipoprotein C-II | P02655 | APOC2 | 0.000 | 0.000 | 1.27 | Down |
| AFVFPK (SEQ ID NO: 15) | C-reactive protein | P02741 | CRP | 0.000 | 0.001 | 1.64 | Up |
| GSPAINVAVHVFR (SEQ ID NO: 9) | Transthyretin | P02766 | TTR | 0.000 | 0.001 | 1.20 | Down |
| ITLPDFTGDLR (SEQ ID NO: 191) | Lipopolysaccharide-binding protein | P18428 | LBP | 0.002 | 0.005 | 1.20 | Up |

Abbreviations: FDR-false discovery rate; AECOPD-acute exacerbations of COPD

Figure 8A:
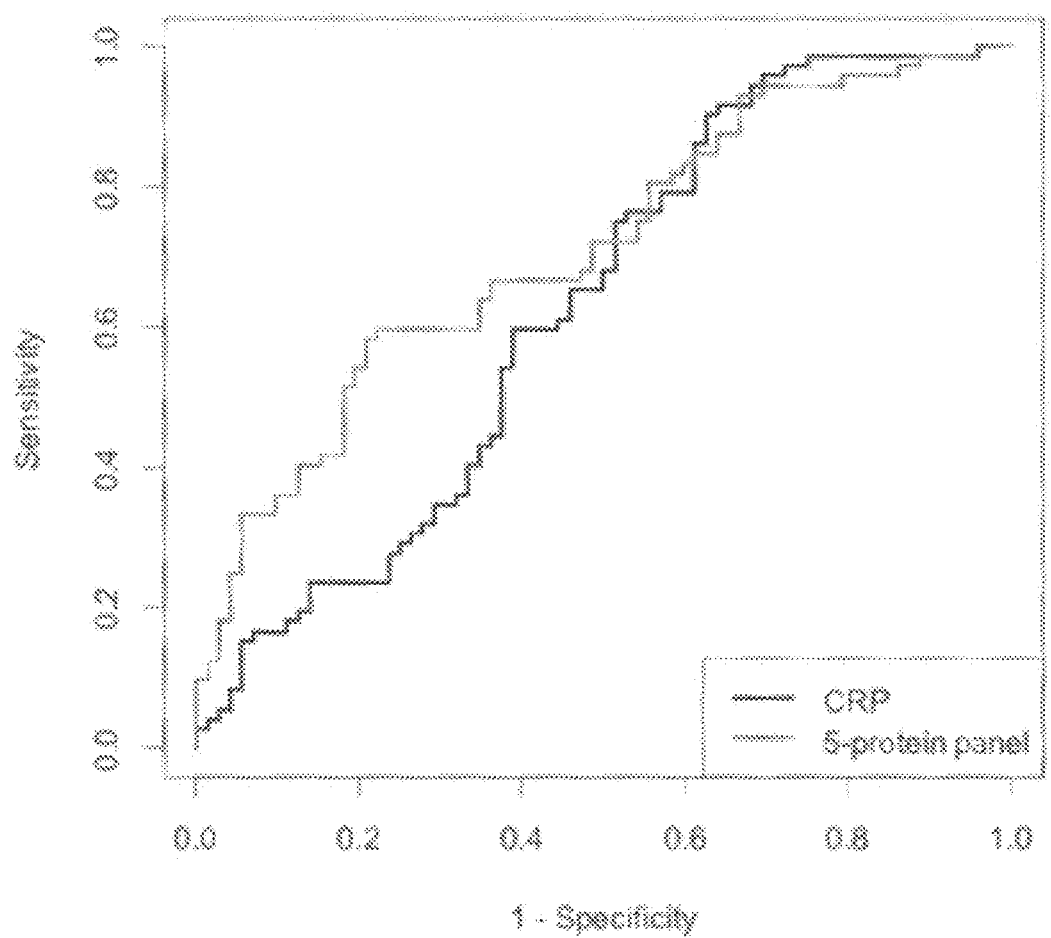
FIGS. 8A-8C. Receiver Operating Characteristics (ROC) Curves for the AECOPD Cohorts. The ROC curves are shown for CRP only and the 5-protein panel in FIG. 8A; the TNF-α discovery cohort in FIG. 8B; and the LEUKO cohort and the RTP cohort in FIG. 8C. The 5-protein panel showed improved performance metrics compared to CRP only.
Figure 8B:
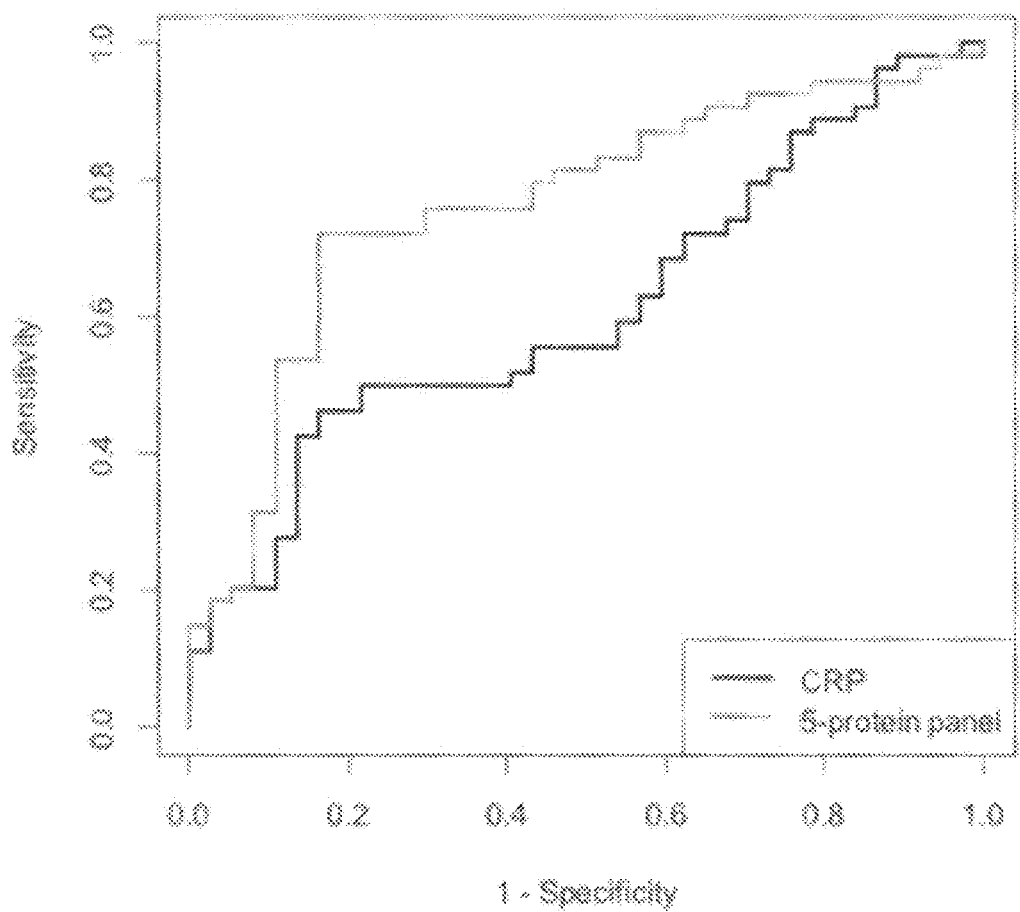
Figure 8C:
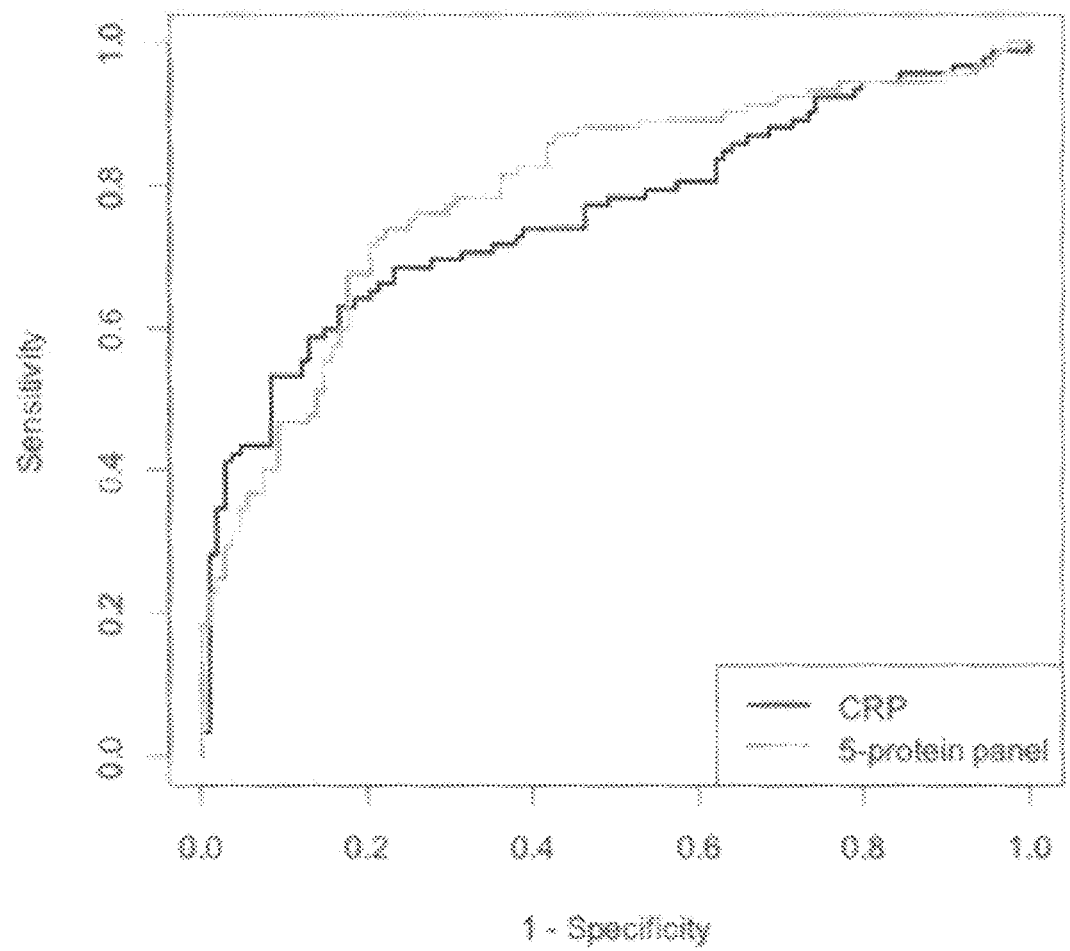

The final elastic net model consisted of five of these proteins (CRP and transthyretin were removed to create the final model). Compared to CRP alone, the 5-protein panel demonstrated a superior receiver operating characteristics (ROC) curve for diagnosing AECOPD in all three cohorts (FIG. 8). The area under the curve (AUC) for the 5-protein was panel was 0.73, 0.77, and 0.79 in the TNF-α, LEUKO, and RTP cohorts, respectively. In comparison, the AUC for CRP was 0.63, 0.61, and 0.76 in the TNF-α, LEUKO, and RTP cohorts, respectively.

A biomarker score based on the weighted contributions of the 5 proteins to the presence of an AECOPD state was calculated for each of the cohorts. The intercept and specific protein weights contributing to the biomarker score for the 5-protein panel are listed in Table 7.

TABLE 7

Biomarker Score Intercept and Specific Protein Weights
Biomarker score = $w_0 + w_1 \cdot protein_1 + w_2 \cdot protein_2 + \ldots + w_N \cdot protein_N$

| Intercept/Protein | w |
|---|---|
| Intercept ($w_0$) | −0.272 |
| Apolipoprotein A-IV | −1.016 |
| Complement component C9 | 0.643 |
| Fibronectin | −0.321 |
| Apolipoprotein C-II | −0.225 |
| Lipopolysaccharide-binding protein | 0.289 |

Figure 9:
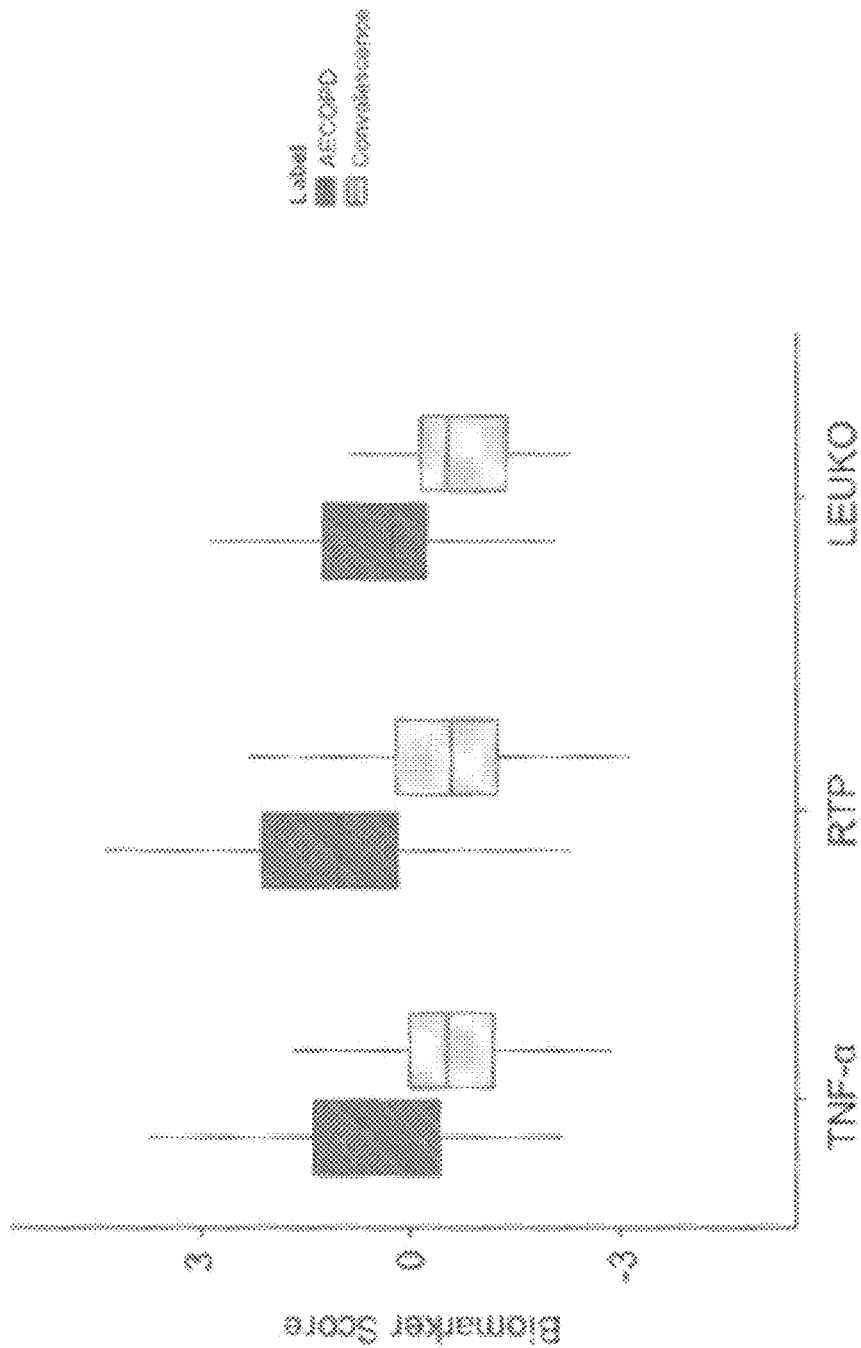
FIG. 9. Biomarker Scores Comparing AECOPD to Non-AECOPD States. Biomarker scores for the TNF-α, RIP, and LEUKO cohorts are shown. Biomarker scores were significantly elevated during the time of AECOPD but fell during the convalescent phase (Wilcoxon rank sum p-value <0.001 for LEUKO, <0.001 for TNF-α, and <0.001 for RTP). The convalescent phase scores for the LEUKO, TNF-α, and RTP cohorts showed no statistically significant differences.

Biomarker scores at each time point for the three cohorts are shown in FIG. 9. In all three cohorts, the biomarker scores at exacerbation time points were significantly greater than the biomarker scores at convalescent time points (Wilcoxon rank sum p-value <0.001 for LEUKO, <0.001 for TNF-α, and <0.001 for RTP). In addition, the biomarker scores during convalescence in the two replication cohorts were not statistically different from the convalescence biomarker scores in the TNF-α discovery cohort. For the RTP cohort, for which additional time points were available, Day 30 and Day 90 biomarker scores (signifying convalescence) were significantly different from Baseline and Day 3 scores (p<0.001). Control subjects (COPD subjects who were not exacerbating) had biomarker scores equivalent to convalescent scores (p=0.35).

A biomarker score decision threshold optimised to detect AECOPD with at least 90% sensitivity in the TNF-α cohort yielded sensitivities of 90%, 91%, and 93% in the TNF-α, LEUKO, and RTP cohorts, respectively. Conversely, a biomarker score decision threshold optimized to detect AECOPD with 90% specificity in the TNF-α cohort yielded specificities of 90%, 92%, and 94% in the TNF-α, LEUKO, and RTP cohorts, respectively.

Discussion

In this first-ever study employing MRM-MS for biomarker verification in AECOPD, we have generated a promising panel of five proteins significantly associated with an AECOPD state with the results replicated in two separate AECOPD cohorts. Biomarker scores derived from this panel were significantly elevated in AECOPD compared to convalescent periods and the performance of this panel provided a significant increase in the AUC estimate over CRP. In a "real life" setting (i.e. the RTP cohort), the biomarker classifier based on these five proteins generated an AUC of 0.79. Now that we have identified the most promising five proteins in the classifier, in the future, we can build more precise MS assays to interrogate these proteins, which will further improve AUC values to values >0.8. This will make clinical translation possible. [20] For a medical condition with a current shortage of available biomarkers, this panel may represent a significant step forward not only in AECOPD diagnosis but also in the recognition of AECOPD resolution at which point therapy could potentially be tapered. Additionally, this panel could be used to identify patients who may need greater intensity or duration of therapy.

Figure 10:
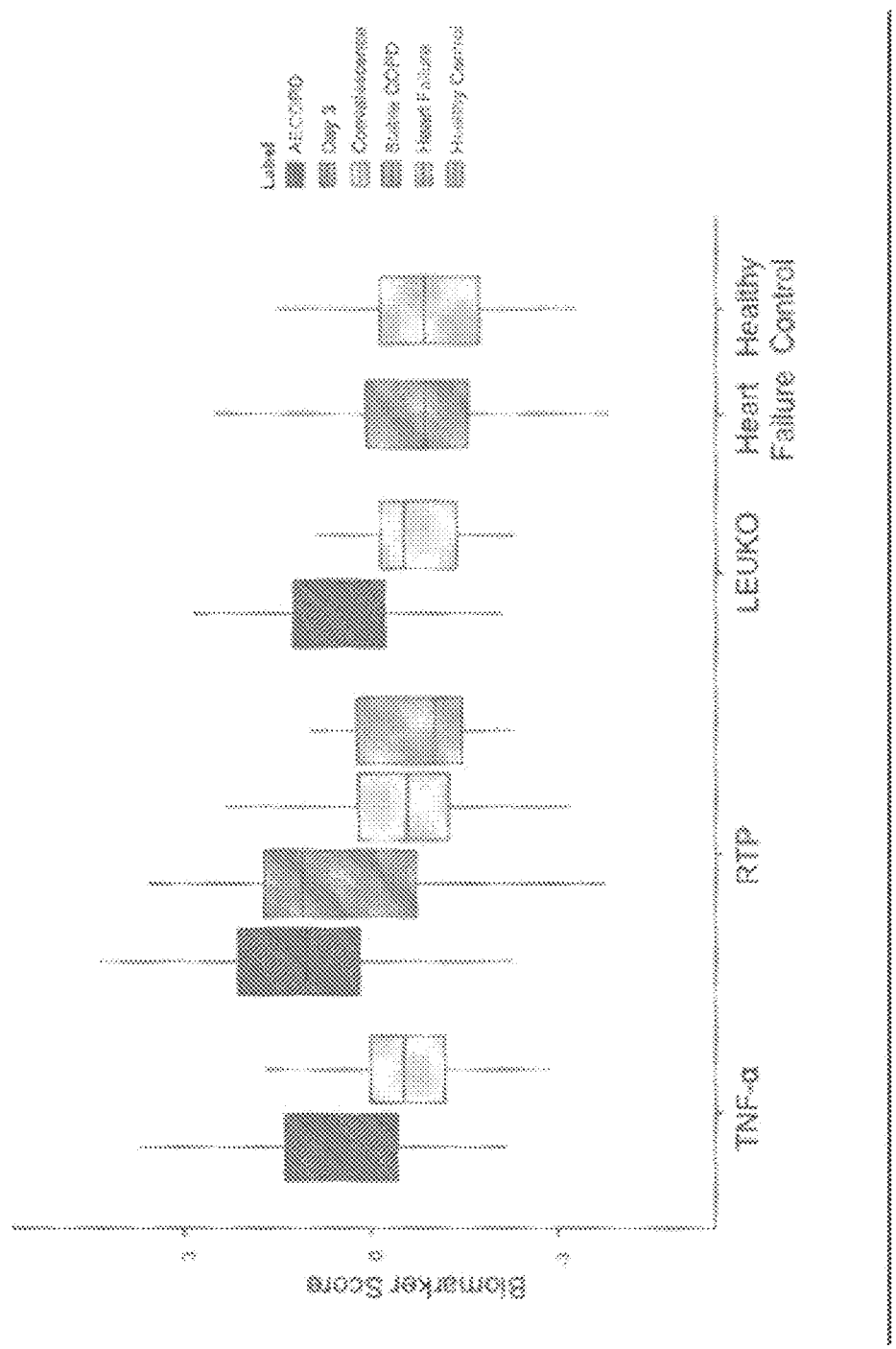
FIG. 10. Biomarker Scores in Chronic Heart Failure Patients and Normal Controls. Biomarker scores for the 5-protein panel are shown for a cohort of chronic heart failure patients (n=218) and for healthy controls (n=49) to compare with the three AECOPD cohorts. Scores for the chronic heart failure patients and for the healthy controls were not statistically different from the convalescent scores of the TNF-α cohort (p=0.07 and p=0.13, respectively). Included in this figure are also Day 3 and non-exacerbating COPD control patients in the RTP cohort, demonstrating that biomarker scores remain high in the immediate AECOPD period and that non-exacerbating COPD controls have similar biomarker scores to convalescent patients.

Further, when tested in non-exacerbating COPD patients who were also enrolled in the RTP cohort and presenting to outpatient follow-up clinics, biomarker scores were no different from AECOPD patients in the convalescent state (see FIG. 10), reinforcing the panel's ability to distinguish between AECOPD and non-AECOPD states.

The MRM-MS approach, although previously applied to numerous other disease states such as lung cancer, psoriatic arthritis, and Parkinson's disease,[14 23 24] marks a departure from traditional methods of biomarker discovery and verification in AECOPD. Previous attempts at identifying biomarkers have relied on known proteins with already available commercial immunoassay platforms, for instance CRP, IL-6, angiopoietin-2, adrenomedullin, and troponin. [6 25-28] Unfortunately, proteins lacking available commercial immunoassays may be entirely overlooked by this strategy. The cost and time required for immunoassay development, however, can be prohibitive.[29] MRM-MS can fill the gap between biomarker discovery and verification by providing a cost-effective platform for quantifying proteins with greater specificity than that provided by immunoassays. Moreover, the multiplexing capacity of MRM-MS confers another distinct advantage over antibody-based tests.

Using MRM-MS, we identified through our protein panel key biological pathways not previously associated with AECOPD pathophysiology. While inflammatory proteins like CRP were indeed differentially expressed in AECOPD, our final biomarker model was not comprised of these proteins, a surprising finding given the extensive attention recently focused on inflammation in the etiology of AECOPD. Instead, our panel was particularly notable for the inclusion of two proteins relating to the cholesterol pathway, apolipoprotein A-IV (APOA4) and apolipoprotein C-II (APOC2) (both decreased in the setting of AECOPD compared to convalescence). While the associations between AECOPD and cardiovascular comorbidities have long been recognized,[8 30 31] the specific role that these proteins play in the development of AECOPD has not yet been established. APOA4, a 46-kDa glycoprotein secreted in the small intestine, is an important constituent of chylomicrons and circulates in plasma either bound to high-density lipoproteins (HDL) or in a free state.[32 33] While it is primarily associated with lipid metabolism and transport,[34 35] it importantly plays a role in anti-oxidant,[36] anti-inflammatory,[37 38] and anti-atherogenic [39 40] responses. The protein's relative decrease during AECOPD might suggest that it plays a protective role in the lung as well, although further studies are needed to establish a precise mechanism. APOC2, an 8.8-kDa protein, circulates in plasma bound to chylomicrons, very low-density lipoproteins (VLDL) and HDL where it serves as an activator of lipoprotein lipase. Deficiencies in APOC2, often inherited as rare autosomal recessive mutations, result in excessive triglyceride levels. Connections between APOC2 to COPD pathogenesis, however, have not been established in the literature.

The three cohorts utilized for biomarker discovery and verification were fundamentally different in terms of baseline demographic markers like age, sex, and lung function. Therefore, the protein panel discovered in the TNF-α cohort may have actually performed better had the subjects in the verification cohorts aligned more similarly with the discovery cohort. This study demonstrates that the biomarker panel can likely be applied across a wide variety of COPD phenotypes with consistent results. We applied the 5-protein biomarker panel to a cohort of chronic heart failure patients and a cohort of healthy controls and the resulting biomarker scores were equivalent to those of convalescent AECOPD patients (see FIG. 10 and Table 8 for cohort demographics and results).

TABLE 8

Demographic Characteristics of Heart Failure and Healthy Control Patients

| Characteristic | Heart Failure Cohort (n = 218) | Healthy Control (n = 49) |
|---|---|---|
| Age (mean ± standard deviation) | 64.9 ± 11.0 | 45.9 ± 14.4 |
| Male (%) | 75.7 | 24.5 |
| White Race (%) | 76.9 | 79.5 |
| Smoking Status | | |
| Never (%) | 37.2 | N/A |
| Current (%) | 11.0 | |
| Former (%) | 51.8 | |

In summary, we demonstrate here for the first time the application of an MRM-MS platform to biomarker discovery in the diagnosis of AECOPD. Not only was this panel able to distinguish AECOPD from the convalescent COPD state in multiple, independent cohorts, but it also revealed potential novel mechanisms for AECOPD by implicating cholesterol pathways previously unreported in the AECOPD literature. For a clinical problem with no current diagnostic test available, our panel may be a significant addition to the management algorithm of COPD patients.

Funding Sources:
Funding was provided by Genome Canada, Genome British Columbia, Genome Quebec, the Canadian Institutes of Health Research, PROOF Centre, St. Paul's Hospital Foundation, the Canadian Respiratory Research Network, and the National Heart, Lung, and Blood Institute's COPD Clinical Research Network (Grants U10 HL074441, U10 HL074418, U10 HL074428, U10 HL074409, U10 HL074407, U10 HL074422, U10 HL074416, U10 HL074408, U10 HL074439, U10 HL0744231, and U10 HL074424).

REFERENCES

1 Donaldson G C, Seemungal T A, Bhowmik A, et al. Relationship between exacerbation frequency and lung function decline in chronic obstructive pulmonary disease. Thorax 2002; 57(10):847-52.
2 Seemungal T A, Donaldson G C, Paul E A, et al. Effect of exacerbation on quality of life in patients with chronic obstructive pulmonary disease. Am J Respir Crit Care Med 1998; 157(5 Pt 1): 1418-22.
3 Soler-Cataluna J J, Martinez-Garcia M A, Roman Sanchez P, et al. Severe acute exacerbations and mortality in patients with chronic obstructive pulmonary disease. Thorax 2005; 60(11):925-31.
4 Chronic obstructive pulmonary disease (COPD) fact sheet. Chicago, Ill.: American Lung Association, 2014. (Accessed Oct. 4, 2014)
5 Celli B R, MacNee W. Standards for the diagnosis and treatment of patients with COPD: a summary of the ATS/ERS position paper. Eur Respir J 2004; 23(6):932-46.
6 Hurst J R, Donaldson G C, Perera W R, et al. Use of plasma biomarkers at exacerbation of chronic obstructive pulmonary disease. Am J Respir Crit Care Med 2006; 174(8):867-74.
7 Bozinovski S, Hutchinson A, Thompson M, et al. Serum amyloid a is a biomarker of acute exacerbations of chronic obstructive pulmonary disease. Am J Respir Crit Care Med 2008; 177(3):269-78.

8 Patel A R, Kowlessar B S, Donaldson G C, et al. Cardiovascular risk, myocardial injury, and exacerbations of chronic obstructive pulmonary disease. Am J Respir Crit Care Med 2013; 188(9):1091-9.
9 Seemungal T, Harper-Owen R, Bhowmik A, et al. Respiratory viruses, symptoms, and inflammatory markers in acute exacerbations and stable chronic obstructive pulmonary disease. Am J Respir Crit Care Med 2001; 164(9): 1618-23.
10 Peacock J L, Anderson H R, Bremner S A, et al. Outdoor air pollution and respiratory health in patients with COPD. Thorax 2011; 66(7):591-6.
11 De Serres G, Lampron N, La Forge J, et al. Importance of viral and bacterial infections in chronic obstructive pulmonary disease exacerbations. J Clin Virol 2009; 46(2):129-33.
12 Meng Z, Veenstra T D. Targeted mass spectrometry approaches for protein biomarker verification. J Proteomics 2011; 74(12):2650-9.
13 Method of the Year 2012. Nat Methods 2012; 10(1):1.
14 Chen C D, Wang C L, Yu C J, et al. Targeted proteomics pipeline reveals potential biomarkers for the diagnosis of metastatic lung cancer in pleural effusion. J Proteome Res 2014; 13(6):2818-29.
15 Quon B S, Dai D L, Hollander Z, et al. Discovery of novel plasma protein biomarkers to predict imminent cystic fibrosis pulmonary exacerbations using multiple reaction monitoring mass spectrometry. Thorax 2015 Mar. 16 [Epub ahead of print].
16 Aaron S D, Vandemheen K L, Maltais F, et al. TNFalpha antagonists for acute exacerbations of COPD: a randomised double-blind controlled trial. Thorax 2013; 68(2):142-8.
17 Woodruff P G, Albert R K, Bailey W C, et al. Randomized trial of zileuton for treatment of COPD exacerbations requiring hospitalization. COPD 2011; 8(1):21-9.
18 Percy A J, Chambers A G, Yang J, et al. Method and platform standardization in MRM-based quantitative plasma proteomics. J Proteomics 2013; 95:66-76.
19 Zou H, Hastie T. Regularization and variable selection via the elastic net. J R Stat Soc Series B 2005; 67(2):301-20.
20 Sin D D, Hollander Z, DeMarco M L, et al. Biomarker Development for COPD: From Discovery to Clinical Implementation. Am J Respir Crit Care Med 2015 Jul. 15 [Epub ahead of print].
21 Leidy N K, Wilcox T K, Jones P W, et al. Standardizing measurement of chronic obstructive pulmonary disease exacerbations. Reliability and validity of a patient-reported diary. Am J Respir Crit Care Med 2011; 183(3): 323-9.
22 Leidy N K, Murray L T, Jones P, et al. Performance of the EXAcerbations of chronic pulmonary disease tool patient-reported outcome measure in three clinical trials of chronic obstructive pulmonary disease. Ann Am Thorac Soc 2014; 11(3):316-25.
23 Ademowo O S, Hernandez B, Collins E, et al. Discovery and confirmation of a protein biomarker panel with potential to predict response to biological therapy in psoriatic arthritis. Ann Rheum Dis 2014 Sep. 3 [Epub ahead of print].
24 Alberio T, McMahon K, Cuccurullo M, et al. Verification of a Parkinson's disease protein signature in T-lymphocytes by multiple reaction monitoring. J Proteome Res 2014; 13(8):3554-61.
25 Meng D Q, Li X J, Song X Y, et al. Diagnostic and Prognostic Value of Plasma Adrenomedullin in COPD Exacerbation. Respir Care 2014; 59(10):1542-9.
26 Wedzicha J A, Seemungal T A, MacCallum P K, et al. Acute exacerbations of chronic obstructive pulmonary disease are accompanied by elevations of plasma fibrinogen and serum IL-6 levels. Thromb Haemost 2000; 84(2): 210-5.
27 Nikolakopoulou S, Hillas G, Perrea D, et al. Serum angiopoietin-2 and CRP levels during COPD exacerbations. COPD 2014; 11(1):46-51.
28 Soyseth V, Bhatnagar R, Holmedahl N H, et al. Acute exacerbation of COPD is associated with fourfold elevation of cardiac troponin T. Heart 2013; 99(2): 122-6.
29 Issaq H J, Veenstra T D. Would you prefer multiple reaction monitoring or antibodies with your biomarker validation? Expert Rev Proteomics 2008; 5(6):761-3.
30 Donaldson G C, Hurst J R, Smith C J, et al. Increased risk of myocardial infarction and stroke following exacerbation of COPD. Chest 2010; 137(5):1091-7.
31 McAllister D A, Maclay J D, Mills N L, et al. Diagnosis of myocardial infarction following hospitalisation for exacerbation of COPD. Eur Respir J 2012; 39(5):1097-103.
32 Utermann G, Beisiegel U. Apolipoprotein A-IV: a protein occurring in human mesenteric lymph chylomicrons and free in plasma. Isolation and quantification. Eur J Biochem 1979; 99(2):333-43.
33 Green P H, Glickman R M, Riley J W, et al. Human apolipoprotein A-IV. Intestinal origin and distribution in plasma. J Clin Invest 1980; 65(4):911-9.
34 Dvorin E, Gorder N L, Benson D M, et al. Apolipoprotein A-IV. A determinant for binding and uptake of high density lipoproteins by rat hepatocytes. J Biol Chem 1986; 261(33):15714-8.
35 Goldberg I J, Scheraldi C A, Yacoub L K, et al. Lipoprotein ApoC-II activation of lipoprotein lipase. Modulation by apolipoprotein A-IV. J Biol Chem 1990; 265(8): 4266-72.
36 Qin X, Swertfeger D K, Zheng S, et al. Apolipoprotein AIV: a potent endogenous inhibitor of lipid oxidation. Am J Physiol 1998; 274(5 Pt 2):H1836-40.
37 Vowinkel T, Mori M, Krieglstein C F, et al. Apolipoprotein A-IV inhibits experimental colitis. J Clin Invest 2004; 114(2):260-9.
38. Recalde D, Ostos M A, Badell E, et al. Human apolipoprotein A-IV reduces secretion of proinflammatory cytokines and atherosclerotic effects of a chronic infection mimicked by lipopolysaccharide. Arterioscler Thromb Vasc Biol 2004; 24(4):756-61.
39 Cohen R D, Castellani L W, Qiao J H, et al. Reduced aortic lesions and elevated high density lipoprotein levels in transgenic mice overexpressing mouse apolipoprotein A-IV. J Clin Invest 1997; 99(8):1906-16.
40 Duverger N, Tremp G, Caillaud J M, et al. Protection against atherogenesis in mice mediated by human apolipoprotein A-IV. Science 1996; 273(5277):966-8.

Example 4

CRP and NT-proBNP Biomarker Panel

This example describes another panel of protein biomarkers that can distinguish AECOPD from convalescent state.

For a larger cohort of RTP patients, the level of CRP and N-terminal pro B-type Natriuretic Peptide (NT-proBNP) was measured on clinical assays. The demographics of this larger RTP cohort are shown in Table 9 below. A biomarker (see Table 10) was created based on a weighted combination of these two proteins:

Biomarker score=−1.244+0.0289*CRP+ 0.000597*NTproBNP

The AUC estimate for the above biomarker was 0.79. When the decision threshold was optimized for 900/sensitivity in this RTP cohort, the resulting sensitivity and specificity estimates were 91% and 31%, respectively.

TABLE 9

| Demographics of larger RTP cohort. | |
|---|---|
| Age years | 68.16 ± 11.39 |
| Male (%) | 62.82 |
| BMI (kg/m²) | 27.27 ± 7.61 |
| Caucasian (%) | 83.64 |

TABLE 9-continued

| Demographics of larger RTP cohort. | |
|---|---|
| Smoking Status | |
| Current (%) | |
| Former (%) | |
| Smoking pack-years | 42.84 ± 20.29 |
| FEV1 (L) | 1.53 ± 0.74 |
| FEV1 (% Predicted) | 53.96 ± 22.14 |
| FVC (L) | 2.78 ± 1.03 |
| FVC (% Predicted) | 76.7 ± 22.36 |
| FEV1/FVC (%) | 55.11 ± 15.11 |
| Bronchodilator Use (%) | 97.92 |
| Inhaled Corticosteroid Use (%) | 36.46 |

Table 10 provides the biomarkers used in this example.

TABLE 10

Proteins with differential levels between AECOPD and convalescent/stable COPD

| Biomarker Protein Name | Direction AECOPD Relative to Convalescent/ Stable COPD | sequence | SEQ ID NO: |
|---|---|---|---|
| CRP | Up | MEKLLCFLVL TSLSHAFGQT DMSRKAFVFP KESDTSYVSL KAPLTKPLKA FTVCLHFYTE LSSTRGYSIF SYATKRQDNE ILIFWSKDIG YSFTVGGSEI LFEVPEVTVA PVHICTSWES ASGIVEFWVD GKPRVRKSLK KGYTVGAEAS IILGQEQDSF GGNFEGSQSL VGDIGNVNMW DFVLSPDEIN TIYLGGPFSP NVLNWRALKY EVQGEVFTKP QLWP | 273 |
| NT-proBNP | Up | HPLGSPGSAS DLETSGLQEQ RNHLQGKLSE LQVEQTSLEP LQESPRTPGV WKSREVATEG IRGHRKMVLY TLRAPR | 274 |

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method for diagnosing acute exacerbations of chronic obstructive pulmonary disease (AECOPD) in a subject, comprising:
    obtaining a protein expression dataset associated with a blood sample obtained from the subject, wherein the protein expression dataset comprises the expression levels of biomarkers apolipoprotein C-II (SEQ ID NO: 22), complement component C9 (SEQ ID NO: 34), apolipoprotein A-IV (SEQ ID NO: 275), fibronectin (SEQ ID NO: 276), lipopolysaccharide binding protein (SEQ ID NO: 277), inter-alpha-trypsin inhibitor heavy chain H2 (SEQ ID NO: 35), heparin cofactor 2 (SEQ ID NO: 33), apolipoprotein A-I (SEQ ID NO: 24), pigment epithelium-derived factor (SEQ ID NO: 29), hemopexin (SEQ ID NO: 42), beta-2-microglobulin (SEQ ID NO: 38), gelsolin (SEQ ID NO: 39), beta-2-glycoprotein 1 (SEQ ID NO: 27), afamin (SEQ ID NO: 23), histidine-rich glycoprotein (SEQ ID NO: 37), transthyretin (SEQ ID NO: 30), apolipoprotein A-II (SEQ ID NO: 26), protein AMBP (SEQ ID NO: 28), and complement component C6 (SEQ ID NO: 32);
    analyzing the protein expression dataset to determine a biomarker score for the subject, wherein the biomarker score is calculated based on weighted contributions of the biomarkers;
    comparing the biomarker score to a biomarker score of a control subject without AECOPD,
    wherein the biomarker score is greater in a subject with AECOPD than in a control subject without AECOPD; and
    administering a treatment comprising short-acting beta2-agonists, anticholinergic bronchodilators, methylxanthines, long-acting bronchodilators, expectorants, oxygen therapy, and/or antibiotics to the subject.

2. The method of claim 1, wherein the method provides a sensitivity of at least 90% in diagnosing AECOPD.

3. The method of claim 1, wherein the protein expression dataset is obtained using mass spectrometry, multiple reaction monitoring-mass spectrometry (MRM-MS), or an antibody.

4. The method of claim 1, wherein the biomarker score is determined based on the formula: Biomarker score=$w_0 + w_1*\text{protein}_1 + w_2*\text{protein}_2 + \ldots + w_N*\text{protein}_N$, where N is the number of proteins in the biomarker panel.

5. The method of claim 1, wherein the subject presents to a physician with dyspnea, cough, and sputum production.

6. The method of claim 1, wherein the method provides a specificity of at least 86% in diagnosing AECOPD.

* * * * *

SEQUENCE LISTING

<160> NUMBER OF SEQ ID NOS: 277

<210> SEQ ID NO 1
<211> LENGTH: 9
<212> TYPE: PRT
<213> ORGANISM: Homo sapiens

<400> SEQUENCE: 1

Thr Ala Ala Gln Asn Leu Tyr Glu Lys
1               5

-continued

```
<210> SEQ ID NO 2
<211> LENGTH: 16
<212> TYPE: PRT
<213> ORGANISM: Homo sapiens

<400> SEQUENCE: 2

Ile Ala Pro Gln Leu Ser Thr Glu Glu Leu Val Ser Leu Gly Glu Lys
1               5                   10                  15

<210> SEQ ID NO 3
<211> LENGTH: 11
<212> TYPE: PRT
<213> ORGANISM: Homo sapiens

<400> SEQUENCE: 3

Ala Thr Glu His Leu Ser Thr Leu Ser Glu Lys
1               5                   10

<210> SEQ ID NO 4
<211> LENGTH: 10
<212> TYPE: PRT
<213> ORGANISM: Homo sapiens

<400> SEQUENCE: 4

Tyr Trp Gly Val Ala Ser Phe Leu Gln Lys
1               5                   10

<210> SEQ ID NO 5
<211> LENGTH: 9
<212> TYPE: PRT
<213> ORGANISM: Homo sapiens

<400> SEQUENCE: 5

Ser Pro Glu Leu Gln Ala Glu Ala Lys
1               5

<210> SEQ ID NO 6
<211> LENGTH: 9
<212> TYPE: PRT
<213> ORGANISM: Homo sapiens

<400> SEQUENCE: 6

Ala Thr Val Val Tyr Gln Gly Glu Arg
1               5

<210> SEQ ID NO 7
<211> LENGTH: 12
<212> TYPE: PRT
<213> ORGANISM: Homo sapiens

<400> SEQUENCE: 7

Ala Phe Ile Gln Leu Trp Ala Phe Asp Ala Val Lys
1               5                   10

<210> SEQ ID NO 8
<211> LENGTH: 10
<212> TYPE: PRT
<213> ORGANISM: Homo sapiens

<400> SEQUENCE: 8

Thr Val Gln Ala Val Leu Thr Val Pro Lys
1               5                   10

<210> SEQ ID NO 9
<211> LENGTH: 13
```

```
<212> TYPE: PRT
<213> ORGANISM: Homo sapiens

<400> SEQUENCE: 9

Gly Ser Pro Ala Ile Asn Val Ala Val His Val Phe Arg
1               5                   10

<210> SEQ ID NO 10
<211> LENGTH: 11
<212> TYPE: PRT
<213> ORGANISM: Homo sapiens

<400> SEQUENCE: 10

Ala Val Val Glu Val Asp Glu Ser Gly Thr Arg
1               5                   10

<210> SEQ ID NO 11
<211> LENGTH: 9
<212> TYPE: PRT
<213> ORGANISM: Homo sapiens

<400> SEQUENCE: 11

Gly Phe Val Val Ala Gly Pro Ser Arg
1               5

<210> SEQ ID NO 12
<211> LENGTH: 9
<212> TYPE: PRT
<213> ORGANISM: Homo sapiens

<400> SEQUENCE: 12

Ser Val Asn Asp Leu Tyr Ile Gln Lys
1               5

<210> SEQ ID NO 13
<211> LENGTH: 9
<212> TYPE: PRT
<213> ORGANISM: Homo sapiens

<400> SEQUENCE: 13

Val Val Glu Glu Ser Glu Leu Ala Arg
1               5

<210> SEQ ID NO 14
<211> LENGTH: 20
<212> TYPE: PRT
<213> ORGANISM: Homo sapiens

<400> SEQUENCE: 14

Phe Leu His Val Pro Asp Thr Phe Glu Gly His Phe Asp Gly Val Pro
1               5                   10                  15

Val Ile Ser Lys
            20

<210> SEQ ID NO 15
<211> LENGTH: 6
<212> TYPE: PRT
<213> ORGANISM: Homo sapiens

<400> SEQUENCE: 15

Ala Phe Val Phe Pro Lys
1               5

<210> SEQ ID NO 16
```

```
<211> LENGTH: 9
<212> TYPE: PRT
<213> ORGANISM: Homo sapiens

<400> SEQUENCE: 16

Asp Gly Tyr Leu Phe Gln Leu Leu Arg
1               5

<210> SEQ ID NO 17
<211> LENGTH: 6
<212> TYPE: PRT
<213> ORGANISM: Homo sapiens

<400> SEQUENCE: 17

Ile Gln Val Tyr Ser Arg
1               5

<210> SEQ ID NO 18
<211> LENGTH: 8
<212> TYPE: PRT
<213> ORGANISM: Homo sapiens

<400> SEQUENCE: 18

Thr Gly Ala Gln Glu Leu Leu Arg
1               5

<210> SEQ ID NO 19
<211> LENGTH: 12
<212> TYPE: PRT
<213> ORGANISM: Homo sapiens

<400> SEQUENCE: 19

Val Ser Glu Gly Asn His Asp Ile Ala Leu Ile Lys
1               5                   10

<210> SEQ ID NO 20
<211> LENGTH: 8
<212> TYPE: PRT
<213> ORGANISM: Homo sapiens

<400> SEQUENCE: 20

Phe Leu Asn Val Leu Ser Pro Arg
1               5

<210> SEQ ID NO 21
<211> LENGTH: 11
<212> TYPE: PRT
<213> ORGANISM: Homo sapiens

<400> SEQUENCE: 21

Asn Phe Pro Ser Pro Val Asp Ala Ala Phe Arg
1               5                   10

<210> SEQ ID NO 22
<211> LENGTH: 101
<212> TYPE: PRT
<213> ORGANISM: Homo sapiens

<400> SEQUENCE: 22

Met Gly Thr Arg Leu Leu Pro Ala Leu Phe Leu Val Leu Leu Val Leu
1               5                   10                  15

Gly Phe Glu Val Gln Gly Thr Gln Gln Pro Gln Gln Asp Glu Met Pro
                20                  25                  30

Ser Pro Thr Phe Leu Thr Gln Val Lys Glu Ser Leu Ser Ser Tyr Trp
```

```
                35                  40                  45
Glu Ser Ala Lys Thr Ala Ala Gln Asn Leu Tyr Glu Lys Thr Tyr Leu
             50                  55                  60
Pro Ala Val Asp Glu Lys Leu Arg Asp Leu Tyr Ser Lys Ser Thr Ala
 65                  70                  75                  80
Ala Met Ser Thr Tyr Thr Gly Ile Phe Thr Asp Gln Val Leu Ser Val
                 85                  90                  95
Leu Lys Gly Glu Glu
            100

<210> SEQ ID NO 23
<211> LENGTH: 599
<212> TYPE: PRT
<213> ORGANISM: Homo sapiens

<400> SEQUENCE: 23

Met Lys Leu Leu Lys Leu Thr Gly Phe Ile Phe Phe Leu Phe Phe Leu
 1               5                  10                  15
Thr Glu Ser Leu Thr Leu Pro Thr Gln Pro Arg Asp Ile Glu Asn Phe
                20                  25                  30
Asn Ser Thr Gln Lys Phe Ile Glu Asp Asn Ile Glu Tyr Ile Thr Ile
                35                  40                  45
Ile Ala Phe Ala Gln Tyr Val Gln Glu Ala Thr Phe Glu Glu Met Glu
             50                  55                  60
Lys Leu Val Lys Asp Met Val Glu Tyr Lys Asp Arg Cys Met Ala Asp
 65                  70                  75                  80
Lys Thr Leu Pro Glu Cys Ser Lys Leu Pro Asn Asn Val Leu Gln Glu
                 85                  90                  95
Lys Ile Cys Ala Met Glu Gly Leu Pro Gln Lys His Asn Phe Ser His
                100                 105                 110
Cys Cys Ser Lys Val Asp Ala Gln Arg Arg Leu Cys Phe Phe Tyr Asn
                115                 120                 125
Lys Lys Ser Asp Val Gly Phe Leu Pro Pro Phe Pro Thr Leu Asp Pro
            130                 135                 140
Glu Glu Lys Cys Gln Ala Tyr Glu Ser Asn Arg Glu Ser Leu Leu Asn
145                 150                 155                 160
His Phe Leu Tyr Glu Val Ala Arg Arg Asn Pro Phe Val Phe Ala Pro
                165                 170                 175
Thr Leu Leu Thr Val Ala Val His Phe Glu Glu Val Ala Lys Ser Cys
                180                 185                 190
Cys Glu Glu Gln Asn Lys Val Asn Cys Leu Gln Thr Arg Ala Ile Pro
                195                 200                 205
Val Thr Gln Tyr Leu Lys Ala Phe Ser Ser Tyr Gln Lys His Val Cys
            210                 215                 220
Gly Ala Leu Leu Lys Phe Gly Thr Lys Val Val His Phe Ile Tyr Ile
225                 230                 235                 240
Ala Ile Leu Ser Gln Lys Phe Pro Lys Ile Glu Phe Lys Glu Leu Ile
                245                 250                 255
Ser Leu Val Glu Asp Val Ser Ser Asn Tyr Asp Gly Cys Cys Glu Gly
                260                 265                 270
Asp Val Val Gln Cys Ile Arg Asp Thr Ser Lys Val Met Asn His Ile
            275                 280                 285
Cys Ser Lys Gln Asp Ser Ile Ser Ser Lys Ile Lys Glu Cys Cys Glu
        290                 295                 300
```

```
Lys Lys Ile Pro Glu Arg Gly Gln Cys Ile Ile Asn Ser Asn Lys Asp
305                 310                 315                 320

Asp Arg Pro Lys Asp Leu Ser Leu Arg Glu Gly Lys Phe Thr Asp Ser
            325                 330                 335

Glu Asn Val Cys Gln Glu Arg Asp Ala Asp Pro Asp Thr Phe Phe Ala
                340                 345                 350

Lys Phe Thr Phe Glu Tyr Ser Arg Arg His Pro Asp Leu Ser Ile Pro
            355                 360                 365

Glu Leu Leu Arg Ile Val Gln Ile Tyr Lys Asp Leu Leu Arg Asn Cys
        370                 375                 380

Cys Asn Thr Glu Asn Pro Pro Gly Cys Tyr Arg Tyr Ala Glu Asp Lys
385                 390                 395                 400

Phe Asn Glu Thr Thr Glu Lys Ser Leu Lys Met Val Gln Gln Glu Cys
                405                 410                 415

Lys His Phe Gln Asn Leu Gly Lys Asp Gly Leu Lys Tyr His Tyr Leu
            420                 425                 430

Ile Arg Leu Thr Lys Ile Ala Pro Gln Leu Ser Thr Glu Glu Leu Val
        435                 440                 445

Ser Leu Gly Glu Lys Met Val Thr Ala Phe Thr Thr Cys Cys Thr Leu
450                 455                 460

Ser Glu Glu Phe Ala Cys Val Asp Asn Leu Ala Asp Leu Val Phe Gly
465                 470                 475                 480

Glu Leu Cys Gly Val Asn Glu Asn Arg Thr Ile Asn Pro Ala Val Asp
                485                 490                 495

His Cys Cys Lys Thr Asn Phe Ala Phe Arg Arg Pro Cys Phe Glu Ser
            500                 505                 510

Leu Lys Ala Asp Lys Thr Tyr Val Pro Pro Phe Ser Gln Asp Leu
        515                 520                 525

Phe Thr Phe His Ala Asp Met Cys Gln Ser Gln Asn Glu Glu Leu Gln
530                 535                 540

Arg Lys Thr Asp Arg Phe Leu Val Asn Leu Val Lys Leu Lys His Glu
545                 550                 555                 560

Leu Thr Asp Glu Glu Leu Gln Ser Leu Phe Thr Asn Phe Ala Asn Val
                565                 570                 575

Val Asp Lys Cys Cys Lys Ala Glu Ser Pro Glu Val Cys Phe Asn Glu
            580                 585                 590

Glu Ser Pro Lys Ile Gly Asn
        595
```

<210> SEQ ID NO 24
<211> LENGTH: 267
<212> TYPE: PRT
<213> ORGANISM: Homo sapiens

<400> SEQUENCE: 24

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80
```

```
Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
        130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
            195                 200                 205

Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 25
<211> LENGTH: 201
<212> TYPE: PRT
<213> ORGANISM: Homo sapiens

<400> SEQUENCE: 25

Met Lys Trp Val Trp Ala Leu Leu Leu Leu Ala Ala Leu Gly Ser Gly
1               5                   10                  15

Arg Ala Glu Arg Asp Cys Arg Val Ser Ser Phe Arg Val Lys Glu Asn
            20                  25                  30

Phe Asp Lys Ala Arg Phe Ser Gly Thr Trp Tyr Ala Met Ala Lys Lys
        35                  40                  45

Asp Pro Glu Gly Leu Phe Leu Gln Asp Asn Ile Val Ala Glu Phe Ser
    50                  55                  60

Val Asp Glu Thr Gly Gln Met Ser Ala Thr Ala Lys Gly Arg Val Arg
65                  70                  75                  80

Leu Leu Asn Asn Trp Asp Val Cys Ala Asp Met Val Gly Thr Phe Thr
                85                  90                  95

Asp Thr Glu Asp Pro Ala Lys Phe Lys Met Lys Tyr Trp Gly Val Ala
            100                 105                 110

Ser Phe Leu Gln Lys Gly Asn Asp Asp His Trp Ile Val Asp Thr Asp
        115                 120                 125

Tyr Asp Thr Tyr Ala Val Gln Tyr Ser Cys Arg Leu Leu Asn Leu Asp
    130                 135                 140

Gly Thr Cys Ala Asp Ser Tyr Ser Phe Val Phe Ser Arg Asp Pro Asn
145                 150                 155                 160

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
```

```
                    180                 185                 190
Asp Gly Arg Ser Glu Arg Asn Leu Leu
            195                 200

<210> SEQ ID NO 26
<211> LENGTH: 100
<212> TYPE: PRT
<213> ORGANISM: Homo sapiens

<400> SEQUENCE: 26

Met Lys Leu Leu Ala Ala Thr Val Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100

<210> SEQ ID NO 27
<211> LENGTH: 345
<212> TYPE: PRT
<213> ORGANISM: Homo sapiens

<400> SEQUENCE: 27

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
    50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
                100                 105                 110

Gly Phe Tyr Leu Asn Gly Ala Asp Ser Ala Lys Cys Thr Glu Glu Gly
            115                 120                 125

Lys Trp Ser Pro Glu Leu Pro Val Cys Ala Pro Ile Ile Cys Pro Pro
        130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
                180                 185                 190

Asn Trp Thr Lys Leu Pro Glu Cys Arg Glu Val Lys Cys Pro Phe Pro
```

```
            195                 200                 205
Ser Arg Pro Asp Asn Gly Phe Val Asn Tyr Pro Ala Lys Pro Thr Leu
210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
                260                 265                 270

Val Val Tyr Gln Gly Glu Arg Val Lys Ile Gln Glu Lys Phe Lys Asn
                275                 280                 285

Gly Met Leu His Gly Asp Lys Val Ser Phe Phe Cys Lys Asn Lys Glu
                290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys
                340                 345

<210> SEQ ID NO 28
<211> LENGTH: 352
<212> TYPE: PRT
<213> ORGANISM: Homo sapiens

<400> SEQUENCE: 28

Met Arg Ser Leu Gly Ala Leu Leu Leu Leu Ser Ala Cys Leu Ala
1               5                   10                  15

Val Ser Ala Gly Pro Val Pro Thr Pro Pro Asp Asn Ile Gln Val Gln
                20                  25                  30

Glu Asn Phe Asn Ile Ser Arg Ile Tyr Gly Lys Trp Tyr Asn Leu Ala
                35                  40                  45

Ile Gly Ser Thr Cys Pro Trp Leu Lys Lys Ile Met Asp Arg Met Thr
50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
                100                 105                 110

Lys Trp Asn Ile Thr Met Glu Ser Tyr Val Val His Thr Asn Tyr Asp
                115                 120                 125

Glu Tyr Ala Ile Phe Leu Thr Lys Lys Phe Ser Arg His His Gly Pro
                130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
                180                 185                 190

Gln Glu Pro Glu Pro Ile Leu Ile Pro Arg Val Arg Arg Ala Val Leu
                195                 200                 205

Pro Gln Glu Glu Glu Gly Ser Gly Gly Gly Gln Leu Val Thr Glu Val
210                 215                 220
```

```
Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
        275                 280                 285

Leu Pro Ile Val Arg Gly Pro Cys Arg Ala Phe Ile Gln Leu Trp Ala
    290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Leu Leu Arg Phe Ser Asn
            340                 345                 350

<210> SEQ ID NO 29
<211> LENGTH: 418
<212> TYPE: PRT
<213> ORGANISM: Homo sapiens

<400> SEQUENCE: 29

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Asp Pro Phe Phe Lys
        35                  40                  45

Val Pro Val Asn Lys Leu Ala Ala Val Ser Asn Phe Gly Tyr Asp
    50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255
```

```
Ser Asp Leu Ser Cys Lys Ile Ala Gln Leu Pro Leu Thr Gly Ser Met
        260                 265                 270

Ser Ile Ile Phe Phe Leu Pro Leu Lys Val Thr Gln Asn Leu Thr Leu
    275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
        370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 30
<211> LENGTH: 147
<212> TYPE: PRT
<213> ORGANISM: Homo sapiens

<400> SEQUENCE: 30

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 31
<211> LENGTH: 406
<212> TYPE: PRT
<213> ORGANISM: Homo sapiens

<400> SEQUENCE: 31
```

```
Met Gln Leu Phe Leu Leu Leu Cys Leu Val Leu Leu Ser Pro Gln Gly
1               5                   10                  15

Ala Ser Leu His Arg His His Pro Arg Glu Met Lys Lys Arg Val Glu
            20                  25                  30

Asp Leu His Val Gly Ala Thr Val Ala Pro Ser Ser Arg Arg Asp Phe
            35                  40                  45

Thr Phe Asp Leu Tyr Arg Ala Leu Ala Ser Ala Ala Pro Ser Gln Ser
50                  55                  60

Ile Phe Phe Ser Pro Val Ser Ile Ser Met Ser Leu Ala Met Leu Ser
65                  70                  75                  80

Leu Gly Ala Gly Ser Ser Thr Lys Met Gln Ile Leu Glu Gly Leu Gly
            85                  90                  95

Leu Asn Leu Gln Lys Ser Ser Glu Lys Glu Leu His Arg Gly Phe Gln
            100                 105                 110

Gln Leu Leu Gln Glu Leu Asn Gln Pro Arg Asp Gly Phe Gln Leu Ser
            115                 120                 125

Leu Gly Asn Ala Leu Phe Thr Asp Leu Val Val Asp Leu Gln Asp Thr
            130                 135                 140

Phe Val Ser Ala Met Lys Thr Leu Tyr Leu Ala Asp Thr Phe Pro Thr
145                 150                 155                 160

Asn Phe Arg Asp Ser Ala Gly Ala Met Lys Gln Ile Asn Asp Tyr Val
            165                 170                 175

Ala Lys Gln Thr Lys Gly Lys Ile Val Asp Leu Leu Lys Asn Leu Asp
            180                 185                 190

Ser Asn Ala Val Val Ile Met Val Asn Tyr Ile Phe Phe Lys Ala Lys
            195                 200                 205

Trp Glu Thr Ser Phe Asn His Lys Gly Thr Gln Glu Gln Asp Phe Tyr
            210                 215                 220

Val Thr Ser Glu Thr Val Val Arg Val Pro Met Met Ser Arg Glu Asp
225                 230                 235                 240

Gln Tyr His Tyr Leu Leu Asp Arg Asn Leu Ser Cys Arg Val Val Gly
            245                 250                 255

Val Pro Tyr Gln Gly Asn Ala Thr Ala Leu Phe Ile Leu Pro Ser Glu
            260                 265                 270

Gly Lys Met Gln Gln Val Glu Asn Gly Leu Ser Glu Lys Thr Leu Arg
            275                 280                 285

Lys Trp Leu Lys Met Phe Lys Arg Gln Leu Glu Leu Tyr Leu Pro
            290                 295                 300

Lys Phe Ser Ile Glu Gly Ser Tyr Gln Leu Glu Lys Val Leu Pro Ser
305                 310                 315                 320

Leu Gly Ile Ser Asn Val Phe Thr Ser His Ala Asp Leu Ser Gly Ile
            325                 330                 335

Ser Asn His Ser Asn Ile Gln Val Ser Glu Met Val His Lys Ala Val
            340                 345                 350

Val Glu Val Asp Glu Ser Gly Thr Arg Ala Ala Ala Thr Gly Thr
            355                 360                 365

Ile Phe Thr Phe Arg Ser Ala Arg Leu Asn Ser Gln Arg Leu Val Phe
            370                 375                 380

Asn Arg Pro Phe Leu Met Phe Ile Val Asp Asn Asn Ile Leu Phe Leu
385                 390                 395                 400

Gly Lys Val Asn Arg Pro
            405
```

<210> SEQ ID NO 32
<211> LENGTH: 934
<212> TYPE: PRT
<213> ORGANISM: Homo sapiens

<400> SEQUENCE: 32

```
Met Ala Arg Arg Ser Val Leu Tyr Phe Ile Leu Leu Asn Ala Leu Ile
 1               5                  10                  15

Asn Lys Gly Gln Ala Cys Phe Cys Asp His Tyr Ala Trp Thr Gln Trp
            20                  25                  30

Thr Ser Cys Ser Lys Thr Cys Asn Ser Gly Thr Gln Ser Arg His Arg
        35                  40                  45

Gln Ile Val Val Asp Lys Tyr Tyr Gln Glu Asn Phe Cys Glu Gln Ile
    50                  55                  60

Cys Ser Lys Gln Glu Thr Arg Glu Cys Asn Trp Gln Arg Cys Pro Ile
65                  70                  75                  80

Asn Cys Leu Leu Gly Asp Phe Gly Pro Trp Ser Asp Cys Asp Pro Cys
                85                  90                  95

Ile Glu Lys Gln Ser Lys Val Arg Ser Val Leu Arg Pro Ser Gln Phe
            100                 105                 110

Gly Gly Gln Pro Cys Thr Ala Pro Leu Val Ala Phe Gln Pro Cys Ile
        115                 120                 125

Pro Ser Lys Leu Cys Lys Ile Glu Glu Ala Asp Cys Lys Asn Lys Phe
    130                 135                 140

Arg Cys Asp Ser Gly Arg Cys Ile Ala Arg Lys Leu Glu Cys Asn Gly
145                 150                 155                 160

Glu Asn Asp Cys Gly Asp Asn Ser Asp Glu Arg Asp Cys Gly Arg Thr
                165                 170                 175

Lys Ala Val Cys Thr Arg Lys Tyr Asn Pro Ile Pro Ser Val Gln Leu
            180                 185                 190

Met Gly Asn Gly Phe His Phe Leu Ala Gly Glu Pro Arg Gly Glu Val
        195                 200                 205

Leu Asp Asn Ser Phe Thr Gly Gly Ile Cys Lys Thr Val Lys Ser Ser
    210                 215                 220

Arg Thr Ser Asn Pro Tyr Arg Val Pro Ala Asn Leu Glu Asn Val Gly
225                 230                 235                 240

Phe Glu Val Gln Thr Ala Glu Asp Asp Leu Lys Thr Asp Phe Tyr Lys
                245                 250                 255

Asp Leu Thr Ser Leu Gly His Asn Glu Asn Gln Gln Gly Ser Phe Ser
            260                 265                 270

Ser Gln Gly Gly Ser Ser Phe Ser Val Pro Ile Phe Tyr Ser Ser Lys
        275                 280                 285

Arg Ser Glu Asn Ile Asn His Asn Ser Ala Phe Lys Gln Ala Ile Gln
    290                 295                 300

Ala Ser His Lys Lys Asp Ser Ser Phe Ile Arg Ile His Lys Val Met
305                 310                 315                 320

Lys Val Leu Asn Phe Thr Thr Lys Ala Lys Asp Leu His Leu Ser Asp
                325                 330                 335

Val Phe Leu Lys Ala Leu Asn His Leu Pro Leu Glu Tyr Asn Ser Ala
            340                 345                 350

Leu Tyr Ser Arg Ile Phe Asp Asp Phe Gly Thr His Tyr Phe Thr Ser
        355                 360                 365

Gly Ser Leu Gly Gly Val Tyr Asp Leu Leu Tyr Gln Phe Ser Ser Glu
    370                 375                 380
```

```
Glu Leu Lys Asn Ser Gly Leu Thr Glu Glu Ala Lys His Cys Val
385                 390                 395                 400

Arg Ile Glu Thr Lys Lys Arg Val Leu Phe Ala Lys Lys Thr Lys Val
        405                 410                 415

Glu His Arg Cys Thr Thr Asn Lys Leu Ser Glu Lys His Glu Gly Ser
            420                 425                 430

Phe Ile Gln Gly Ala Glu Lys Ser Ile Ser Leu Ile Arg Gly Gly Arg
        435                 440                 445

Ser Glu Tyr Gly Ala Ala Leu Ala Trp Glu Lys Gly Ser Ser Gly Leu
    450                 455                 460

Glu Glu Lys Thr Phe Ser Glu Trp Leu Glu Ser Val Lys Glu Asn Pro
465                 470                 475                 480

Ala Val Ile Asp Phe Glu Leu Ala Pro Ile Val Asp Leu Val Arg Asn
            485                 490                 495

Ile Pro Cys Ala Val Thr Lys Arg Asn Asn Leu Arg Lys Ala Leu Gln
        500                 505                 510

Glu Tyr Ala Ala Lys Phe Asp Pro Cys Gln Cys Ala Pro Cys Pro Asn
    515                 520                 525

Asn Gly Arg Pro Thr Leu Ser Gly Thr Glu Cys Leu Cys Val Cys Gln
530                 535                 540

Ser Gly Thr Tyr Gly Glu Asn Cys Glu Lys Gln Ser Pro Asp Tyr Lys
545                 550                 555                 560

Ser Asn Ala Val Asp Gly Gln Trp Gly Cys Trp Ser Ser Trp Ser Thr
            565                 570                 575

Cys Asp Ala Thr Tyr Lys Arg Ser Arg Thr Arg Glu Cys Asn Asn Pro
        580                 585                 590

Ala Pro Gln Arg Gly Gly Lys Arg Cys Glu Gly Glu Lys Arg Gln Glu
    595                 600                 605

Glu Asp Cys Thr Phe Ser Ile Met Glu Asn Asn Gly Gln Pro Cys Ile
610                 615                 620

Asn Asp Asp Glu Glu Met Lys Glu Val Asp Leu Pro Glu Ile Glu Ala
625                 630                 635                 640

Asp Ser Gly Cys Pro Gln Pro Val Pro Pro Glu Asn Gly Phe Ile Arg
            645                 650                 655

Asn Glu Lys Gln Leu Tyr Leu Val Gly Glu Asp Val Glu Ile Ser Cys
        660                 665                 670

Leu Thr Gly Phe Glu Thr Val Gly Tyr Gln Tyr Phe Arg Cys Leu Pro
    675                 680                 685

Asp Gly Thr Trp Arg Gln Gly Asp Val Glu Cys Gln Arg Thr Glu Cys
690                 695                 700

Ile Lys Pro Val Val Gln Glu Val Leu Thr Ile Thr Pro Phe Gln Arg
705                 710                 715                 720

Leu Tyr Arg Ile Gly Glu Ser Ile Glu Leu Thr Cys Pro Lys Gly Phe
            725                 730                 735

Val Val Ala Gly Pro Ser Arg Tyr Thr Cys Gln Gly Asn Ser Trp Thr
        740                 745                 750

Pro Pro Ile Ser Asn Ser Leu Thr Cys Glu Lys Asp Thr Leu Thr Lys
    755                 760                 765

Leu Lys Gly His Cys Gln Leu Gly Gln Lys Gln Ser Gly Ser Glu Cys
770                 775                 780

Ile Cys Met Ser Pro Glu Glu Asp Cys Ser His His Ser Glu Asp Leu
785                 790                 795                 800

Cys Val Phe Asp Thr Asp Ser Asn Asp Tyr Phe Thr Ser Pro Ala Cys
```

-continued

```
                805                 810                 815
Lys Phe Leu Ala Glu Lys Cys Leu Asn Asn Gln Gln Leu His Phe Leu
                820                 825                 830

His Ile Gly Ser Cys Gln Asp Gly Arg Gln Leu Glu Trp Gly Leu Glu
                835                 840                 845

Arg Thr Arg Leu Ser Ser Asn Ser Thr Lys Lys Glu Ser Cys Gly Tyr
850                 855                 860

Asp Thr Cys Tyr Asp Trp Glu Lys Cys Ser Ala Ser Thr Ser Lys Cys
865                 870                 875                 880

Val Cys Leu Leu Pro Pro Gln Cys Phe Lys Gly Gly Asn Gln Leu Tyr
                885                 890                 895

Cys Val Lys Met Gly Ser Ser Ser Glu Lys Thr Leu Asn Ile Cys
                900                 905                 910

Glu Val Gly Thr Ile Arg Cys Ala Asn Arg Lys Met Glu Ile Leu His
                915                 920                 925

Pro Gly Lys Cys Leu Ala
                930

<210> SEQ ID NO 33
<211> LENGTH: 499
<212> TYPE: PRT
<213> ORGANISM: Homo sapiens

<400> SEQUENCE: 33

Met Lys His Ser Leu Asn Ala Leu Leu Ile Phe Leu Ile Ile Thr Ser
1               5                   10                  15

Ala Trp Gly Gly Ser Lys Gly Pro Leu Asp Gln Leu Glu Lys Gly Gly
                20                  25                  30

Glu Thr Ala Gln Ser Ala Asp Pro Gln Trp Glu Gln Leu Asn Asn Lys
            35                  40                  45

Asn Leu Ser Met Pro Leu Leu Pro Ala Asp Phe His Lys Glu Asn Thr
    50                  55                  60

Val Thr Asn Asp Trp Ile Pro Glu Gly Glu Glu Asp Asp Asp Tyr Leu
65                  70                  75                  80

Asp Leu Glu Lys Ile Phe Ser Glu Asp Asp Tyr Ile Asp Ile Val
                85                  90                  95

Asp Ser Leu Ser Val Ser Pro Thr Asp Ser Asp Val Ser Ala Gly Asn
            100                 105                 110

Ile Leu Gln Leu Phe His Gly Lys Ser Arg Ile Gln Arg Leu Asn Ile
    115                 120                 125

Leu Asn Ala Lys Phe Ala Phe Asn Leu Tyr Arg Val Leu Lys Asp Gln
130                 135                 140

Val Asn Thr Phe Asp Asn Ile Phe Ile Ala Pro Val Gly Ile Ser Thr
145                 150                 155                 160

Ala Met Gly Met Ile Ser Leu Gly Leu Lys Gly Glu Thr His Glu Gln
                165                 170                 175

Val His Ser Ile Leu His Phe Lys Asp Phe Val Asn Ala Ser Ser Lys
            180                 185                 190

Tyr Glu Ile Thr Thr Ile His Asn Leu Phe Arg Lys Leu Thr His Arg
    195                 200                 205

Leu Phe Arg Arg Asn Phe Gly Tyr Thr Leu Arg Ser Val Asn Asp Leu
210                 215                 220

Tyr Ile Gln Lys Gln Phe Pro Ile Leu Leu Asp Phe Lys Thr Lys Val
225                 230                 235                 240
```

Arg Glu Tyr Tyr Phe Ala Glu Ala Gln Ile Ala Asp Phe Ser Asp Pro
                245                 250                 255

Ala Phe Ile Ser Lys Thr Asn Asn His Ile Met Lys Leu Thr Lys Gly
            260                 265                 270

Leu Ile Lys Asp Ala Leu Glu Asn Ile Asp Pro Ala Thr Gln Met Met
        275                 280                 285

Ile Leu Asn Cys Ile Tyr Phe Lys Gly Ser Trp Val Asn Lys Phe Pro
    290                 295                 300

Val Glu Met Thr His Asn His Asn Phe Arg Leu Asn Glu Arg Glu Val
305                 310                 315                 320

Val Lys Val Ser Met Met Gln Thr Lys Gly Asn Phe Leu Ala Ala Asn
                325                 330                 335

Asp Gln Glu Leu Asp Cys Asp Ile Leu Gln Leu Glu Tyr Val Gly Gly
            340                 345                 350

Ile Ser Met Leu Ile Val Val Pro His Lys Met Ser Gly Met Lys Thr
        355                 360                 365

Leu Glu Ala Gln Leu Thr Pro Arg Val Val Glu Arg Trp Gln Lys Ser
    370                 375                 380

Met Thr Asn Arg Thr Arg Glu Val Leu Leu Pro Lys Phe Lys Leu Glu
385                 390                 395                 400

Lys Asn Tyr Asn Leu Val Glu Ser Leu Lys Leu Met Gly Ile Arg Met
                405                 410                 415

Leu Phe Asp Lys Asn Gly Asn Met Ala Gly Ile Ser Asp Gln Arg Ile
            420                 425                 430

Ala Ile Asp Leu Phe Lys His Gln Gly Thr Ile Thr Val Asn Glu Glu
        435                 440                 445

Gly Thr Gln Ala Thr Thr Val Thr Thr Val Gly Phe Met Pro Leu Ser
    450                 455                 460

Thr Gln Val Arg Phe Thr Val Asp Arg Pro Phe Leu Phe Leu Ile Tyr
465                 470                 475                 480

Glu His Arg Thr Ser Cys Leu Leu Phe Met Gly Arg Val Ala Asn Pro
                485                 490                 495

Ser Arg Ser

<210> SEQ ID NO 34
<211> LENGTH: 559
<212> TYPE: PRT
<213> ORGANISM: Homo sapiens

<400> SEQUENCE: 34

Met Ser Ala Cys Arg Ser Phe Ala Val Ala Ile Cys Ile Leu Glu Ile
1               5                   10                  15

Ser Ile Leu Thr Ala Gln Tyr Thr Thr Ser Tyr Asp Pro Glu Leu Thr
            20                  25                  30

Glu Ser Ser Gly Ser Ala Ser His Ile Asp Cys Arg Met Ser Pro Trp
        35                  40                  45

Ser Glu Trp Ser Gln Cys Asp Pro Cys Leu Arg Gln Met Phe Arg Ser
    50                  55                  60

Arg Ser Ile Glu Val Phe Gly Gln Phe Asn Gly Lys Arg Cys Thr Asp
65                  70                  75                  80

Ala Val Gly Asp Arg Arg Gln Cys Val Pro Thr Glu Pro Cys Glu Asp
                85                  90                  95

Ala Glu Asp Asp Cys Gly Asn Asp Phe Gln Cys Ser Thr Gly Arg Cys
            100                 105                 110

-continued

```
Ile Lys Met Arg Leu Arg Cys Asn Gly Asp Asn Asp Cys Gly Asp Phe
            115                 120                 125

Ser Asp Glu Asp Cys Glu Ser Glu Pro Arg Pro Cys Arg Asp
        130                 135                 140

Arg Val Glu Glu Ser Glu Leu Ala Arg Thr Ala Gly Tyr Gly Ile
145                 150                 155                 160

Asn Ile Leu Gly Met Asp Pro Leu Ser Thr Pro Phe Asp Asn Glu Phe
                165                 170                 175

Tyr Asn Gly Leu Cys Asn Arg Asp Arg Asp Gly Asn Thr Leu Thr Tyr
            180                 185                 190

Tyr Arg Arg Pro Trp Asn Val Ala Ser Leu Ile Tyr Glu Thr Lys Gly
        195                 200                 205

Glu Lys Asn Phe Arg Thr Glu His Tyr Glu Glu Gln Ile Glu Ala Phe
    210                 215                 220

Lys Ser Ile Ile Gln Glu Lys Thr Ser Asn Phe Asn Ala Ala Ile Ser
225                 230                 235                 240

Leu Lys Phe Thr Pro Thr Glu Thr Asn Lys Ala Glu Gln Cys Cys Glu
                245                 250                 255

Glu Thr Ala Ser Ser Ile Ser Leu His Gly Lys Gly Ser Phe Arg Phe
            260                 265                 270

Ser Tyr Ser Lys Asn Glu Thr Tyr Gln Leu Phe Leu Ser Tyr Ser Ser
        275                 280                 285

Lys Lys Glu Lys Met Phe Leu His Val Lys Gly Glu Ile His Leu Gly
    290                 295                 300

Arg Phe Val Met Arg Asn Arg Asp Val Val Leu Thr Thr Thr Phe Val
305                 310                 315                 320

Asp Asp Ile Lys Ala Leu Pro Thr Thr Tyr Glu Lys Gly Glu Tyr Phe
                325                 330                 335

Ala Phe Leu Glu Thr Tyr Gly Thr His Tyr Ser Ser Ser Gly Ser Leu
            340                 345                 350

Gly Gly Leu Tyr Glu Leu Ile Tyr Val Leu Asp Lys Ala Ser Met Lys
        355                 360                 365

Arg Lys Gly Val Glu Leu Lys Asp Ile Lys Arg Cys Leu Gly Tyr His
    370                 375                 380

Leu Asp Val Ser Leu Ala Phe Ser Glu Ile Ser Val Gly Ala Glu Phe
385                 390                 395                 400

Asn Lys Asp Asp Cys Val Lys Arg Gly Glu Gly Arg Ala Val Asn Ile
                405                 410                 415

Thr Ser Glu Asn Leu Ile Asp Asp Val Val Ser Leu Ile Arg Gly Gly
            420                 425                 430

Thr Arg Lys Tyr Ala Phe Glu Leu Lys Glu Lys Leu Leu Arg Gly Thr
        435                 440                 445

Val Ile Asp Val Thr Asp Phe Val Asn Trp Ala Ser Ser Ile Asn Asp
    450                 455                 460

Ala Pro Val Leu Ile Ser Gln Lys Leu Ser Pro Ile Tyr Asn Leu Val
465                 470                 475                 480

Pro Val Lys Met Lys Asn Ala His Leu Lys Lys Gln Asn Leu Glu Arg
                485                 490                 495

Ala Ile Glu Asp Tyr Ile Asn Glu Phe Ser Val Arg Lys Cys His Thr
            500                 505                 510

Cys Gln Asn Gly Gly Thr Val Ile Leu Met Asp Gly Lys Cys Leu Cys
        515                 520                 525

Ala Cys Pro Phe Lys Phe Glu Gly Ile Ala Cys Glu Ile Ser Lys Gln
```

```
                    530                 535                 540
Lys Ile Ser Glu Gly Leu Pro Ala Leu Glu Phe Pro Asn Glu Lys
545                 550                 555

<210> SEQ ID NO 35
<211> LENGTH: 946
<212> TYPE: PRT
<213> ORGANISM: Homo sapiens

<400> SEQUENCE: 35

Met Lys Arg Leu Thr Cys Phe Phe Ile Cys Phe Phe Leu Ser Glu Val
1               5                   10                  15

Ser Gly Phe Glu Ile Pro Ile Asn Gly Leu Ser Glu Phe Val Asp Tyr
                20                  25                  30

Glu Asp Leu Val Glu Leu Ala Pro Gly Lys Phe Gln Leu Val Ala Glu
            35                  40                  45

Asn Arg Arg Tyr Gln Arg Ser Leu Pro Gly Glu Ser Glu Glu Met Met
        50                  55                  60

Glu Glu Val Asp Gln Val Thr Leu Tyr Ser Tyr Lys Val Gln Ser Thr
65                  70                  75                  80

Ile Thr Ser Arg Met Ala Thr Thr Met Ile Gln Ser Lys Val Val Asn
                85                  90                  95

Asn Ser Pro Gln Pro Gln Asn Val Val Phe Asp Val Gln Ile Pro Lys
            100                 105                 110

Gly Ala Phe Ile Ser Asn Phe Ser Met Thr Val Asp Gly Lys Thr Phe
        115                 120                 125

Arg Ser Ser Ile Lys Glu Lys Thr Val Gly Arg Ala Leu Tyr Ala Gln
130                 135                 140

Ala Arg Ala Lys Gly Lys Thr Ala Gly Leu Val Arg Ser Ser Ala Leu
145                 150                 155                 160

Asp Met Glu Asn Phe Arg Thr Glu Val Asn Val Leu Pro Gly Ala Lys
                165                 170                 175

Val Gln Phe Glu Leu His Tyr Gln Glu Val Lys Trp Arg Lys Leu Gly
            180                 185                 190

Ser Tyr Glu His Arg Ile Tyr Leu Gln Pro Gly Arg Leu Ala Lys His
        195                 200                 205

Leu Glu Val Asp Val Trp Val Ile Glu Pro Gln Gly Leu Arg Phe Leu
210                 215                 220

His Val Pro Asp Thr Phe Glu Gly His Phe Asp Gly Val Pro Val Ile
225                 230                 235                 240

Ser Lys Gly Gln Gln Lys Ala His Val Ser Phe Lys Pro Thr Val Ala
                245                 250                 255

Gln Gln Arg Ile Cys Pro Asn Cys Arg Glu Thr Ala Val Asp Gly Glu
            260                 265                 270

Leu Val Val Leu Tyr Asp Val Lys Arg Glu Lys Ala Gly Glu Leu
        275                 280                 285

Glu Val Phe Asn Gly Tyr Phe Val His Phe Phe Ala Pro Asp Asn Leu
        290                 295                 300

Asp Pro Ile Pro Lys Asn Ile Leu Phe Val Ile Asp Val Ser Gly Ser
305                 310                 315                 320

Met Trp Gly Val Lys Met Lys Gln Thr Val Glu Ala Met Lys Thr Ile
                325                 330                 335

Leu Asp Asp Leu Arg Ala Glu Asp His Phe Ser Val Ile Asp Phe Asn
            340                 345                 350
```

-continued

```
Gln Asn Ile Arg Thr Trp Arg Asn Asp Leu Ile Ser Ala Thr Lys Thr
        355                 360                 365

Gln Val Ala Asp Ala Lys Arg Tyr Ile Glu Lys Ile Gln Pro Ser Gly
    370                 375                 380

Gly Thr Asn Ile Asn Glu Ala Leu Leu Arg Ala Ile Phe Ile Leu Asn
385                 390                 395                 400

Glu Ala Asn Asn Leu Gly Leu Leu Asp Pro Asn Ser Val Ser Leu Ile
                405                 410                 415

Ile Leu Val Ser Asp Gly Asp Pro Thr Val Gly Glu Leu Lys Leu Ser
            420                 425                 430

Lys Ile Gln Lys Asn Val Lys Glu Asn Ile Gln Asp Asn Ile Ser Leu
        435                 440                 445

Phe Ser Leu Gly Met Gly Phe Asp Val Asp Tyr Asp Phe Leu Lys Arg
    450                 455                 460

Leu Ser Asn Glu Asn His Gly Ile Ala Gln Arg Ile Tyr Gly Asn Gln
465                 470                 475                 480

Asp Thr Ser Ser Gln Leu Lys Lys Phe Tyr Asn Gln Val Ser Thr Pro
                485                 490                 495

Leu Leu Arg Asn Val Gln Phe Asn Tyr Pro His Thr Ser Val Thr Asp
            500                 505                 510

Val Thr Gln Asn Asn Phe His Asn Tyr Phe Gly Gly Ser Glu Ile Val
        515                 520                 525

Val Ala Gly Lys Phe Asp Pro Ala Lys Leu Asp Gln Ile Glu Ser Val
    530                 535                 540

Ile Thr Ala Thr Ser Ala Asn Thr Gln Leu Val Leu Glu Thr Leu Ala
545                 550                 555                 560

Gln Met Asp Asp Leu Gln Asp Phe Leu Ser Lys Asp Lys His Ala Asp
                565                 570                 575

Pro Asp Phe Thr Arg Lys Leu Trp Ala Tyr Leu Thr Ile Asn Gln Leu
            580                 585                 590

Leu Ala Glu Arg Ser Leu Ala Pro Thr Ala Ala Lys Arg Arg Ile
        595                 600                 605

Thr Arg Ser Ile Leu Gln Met Ser Leu Asp His His Ile Val Thr Pro
    610                 615                 620

Leu Thr Ser Leu Val Ile Glu Asn Glu Ala Gly Asp Glu Arg Met Leu
625                 630                 635                 640

Ala Asp Ala Pro Pro Gln Asp Pro Ser Cys Cys Ser Gly Ala Leu Tyr
                645                 650                 655

Tyr Gly Ser Lys Val Val Pro Asp Ser Thr Pro Ser Trp Ala Asn Pro
            660                 665                 670

Ser Pro Thr Pro Val Ile Ser Met Leu Ala Gln Gly Ser Gln Val Leu
        675                 680                 685

Glu Ser Thr Pro Pro His Val Met Arg Val Glu Asn Asp Pro His
    690                 695                 700

Phe Ile Ile Tyr Leu Pro Lys Ser Gln Lys Asn Ile Cys Phe Asn Ile
705                 710                 715                 720

Asp Ser Glu Pro Gly Lys Ile Leu Asn Leu Val Ser Asp Pro Glu Ser
                725                 730                 735

Gly Ile Val Val Asn Gly Gln Leu Val Gly Ala Lys Lys Pro Asn Asn
            740                 745                 750

Gly Lys Leu Ser Thr Tyr Phe Gly Lys Leu Gly Phe Tyr Phe Gln Ser
        755                 760                 765

Glu Asp Ile Lys Ile Glu Ile Ser Thr Glu Thr Ile Thr Leu Ser His
```

```
                770               775               780
Gly Ser Ser Thr Phe Ser Leu Ser Trp Ser Asp Thr Ala Gln Val Thr
785               790               795               800

Asn Gln Arg Val Gln Ile Ser Val Lys Lys Glu Lys Val Val Thr Ile
            805               810               815

Thr Leu Asp Lys Glu Met Ser Phe Ser Val Leu Leu His Arg Val Trp
                820               825               830

Lys Lys His Pro Val Asn Val Asp Phe Leu Gly Ile Tyr Ile Pro Pro
            835               840               845

Thr Asn Lys Phe Ser Pro Lys Ala His Gly Leu Ile Gly Gln Phe Met
        850               855               860

Gln Glu Pro Lys Ile His Ile Phe Asn Glu Arg Pro Gly Lys Asp Pro
865               870               875               880

Glu Lys Pro Glu Ala Ser Met Glu Val Lys Gly Gln Lys Leu Ile Ile
            885               890               895

Thr Arg Gly Leu Gln Lys Asp Tyr Arg Thr Asp Leu Val Phe Gly Thr
        900               905               910

Asp Val Thr Cys Trp Phe Val His Asn Ser Gly Lys Gly Phe Ile Asp
            915               920               925

Gly His Tyr Lys Asp Tyr Phe Val Pro Gln Leu Tyr Ser Phe Leu Lys
        930               935               940

Arg Pro
945

<210> SEQ ID NO 36
<211> LENGTH: 224
<212> TYPE: PRT
<213> ORGANISM: Homo sapiens

<400> SEQUENCE: 36

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190
```

Tyr Leu Gly Gly Pro Phe Ser Pro Asn Val Leu Asn Trp Arg Ala Leu
            195                 200                 205

Lys Tyr Glu Val Gln Gly Glu Val Phe Thr Lys Pro Gln Leu Trp Pro
    210                 215                 220

<210> SEQ ID NO 37
<211> LENGTH: 525
<212> TYPE: PRT
<213> ORGANISM: Homo sapiens

<400> SEQUENCE: 37

Met Lys Ala Leu Ile Ala Ala Leu Leu Leu Ile Thr Leu Gln Tyr Ser
1               5                   10                  15

Cys Ala Val Ser Pro Thr Asp Cys Ser Ala Val Glu Pro Glu Ala Glu
            20                  25                  30

Lys Ala Leu Asp Leu Ile Asn Lys Arg Arg Arg Asp Gly Tyr Leu Phe
        35                  40                  45

Gln Leu Leu Arg Ile Ala Asp Ala His Leu Asp Arg Val Glu Asn Thr
    50                  55                  60

Thr Val Tyr Tyr Leu Val Leu Asp Val Gln Glu Ser Asp Cys Ser Val
65                  70                  75                  80

Leu Ser Arg Lys Tyr Trp Asn Asp Cys Glu Pro Pro Asp Ser Arg Arg
                85                  90                  95

Pro Ser Glu Ile Val Ile Gly Gln Cys Lys Val Ile Ala Thr Arg His
            100                 105                 110

Ser His Glu Ser Gln Asp Leu Arg Val Ile Asp Phe Asn Cys Thr Thr
        115                 120                 125

Ser Ser Val Ser Ser Ala Leu Ala Asn Thr Lys Asp Ser Pro Val Leu
    130                 135                 140

Ile Asp Phe Phe Glu Asp Thr Glu Arg Tyr Arg Lys Gln Ala Asn Lys
145                 150                 155                 160

Ala Leu Glu Lys Tyr Lys Glu Glu Asn Asp Asp Phe Ala Ser Phe Arg
                165                 170                 175

Val Asp Arg Ile Glu Arg Val Ala Arg Val Arg Gly Gly Glu Gly Thr
            180                 185                 190

Gly Tyr Phe Val Asp Phe Ser Val Arg Asn Cys Pro Arg His His Phe
        195                 200                 205

Pro Arg His Pro Asn Val Phe Gly Phe Cys Arg Ala Asp Leu Phe Tyr
    210                 215                 220

Asp Val Glu Ala Leu Asp Leu Glu Ser Pro Lys Asn Leu Val Ile Asn
225                 230                 235                 240

Cys Glu Val Phe Asp Pro Gln Glu His Glu Asn Ile Asn Gly Val Pro
                245                 250                 255

Pro His Leu Gly His Pro Phe His Trp Gly Gly His Glu Arg Ser Ser
            260                 265                 270

Thr Thr Lys Pro Pro Phe Lys Pro His Gly Ser Arg Asp His His His
        275                 280                 285

Pro His Lys Pro His Glu His Gly Pro Pro Pro Pro Asp Glu Arg
    290                 295                 300

Asp His Ser His Gly Pro Pro Leu Pro Gln Gly Pro Pro Leu Leu
305                 310                 315                 320

Pro Met Ser Cys Ser Ser Cys Gln His Ala Thr Phe Gly Thr Asn Gly
                325                 330                 335

Ala Gln Arg His Ser His Asn Asn Asn Ser Ser Asp Leu His Pro His
            340                 345                 350

-continued

```
Lys His His Ser His Glu Gln His Pro His Gly His His Pro His Ala
        355                 360                 365
His His Pro His Glu His Asp Thr His Arg Gln His Pro His Gly His
    370                 375                 380
His Pro His Gly His His Pro His Gly His His Pro His Gly His His
385                 390                 395                 400
Pro His Gly His His Pro His Cys His Asp Phe Gln Asp Tyr Gly Pro
                405                 410                 415
Cys Asp Pro Pro His Asn Gln Gly His Cys Cys His Gly His Gly
            420                 425                 430
Pro Pro Pro Gly His Leu Arg Arg Gly Pro Gly Lys Gly Pro Arg
        435                 440                 445
Pro Phe His Cys Arg Gln Ile Gly Ser Val Tyr Arg Leu Pro Pro Leu
    450                 455                 460
Arg Lys Gly Glu Val Leu Pro Leu Pro Glu Ala Asn Phe Pro Ser Phe
465                 470                 475                 480
Pro Leu Pro His His Lys His Pro Leu Lys Pro Asp Asn Gln Pro Phe
                485                 490                 495
Pro Gln Ser Val Ser Glu Ser Cys Pro Gly Lys Phe Lys Ser Gly Phe
            500                 505                 510
Pro Gln Val Ser Met Phe Phe Thr His Thr Phe Pro Lys
        515                 520                 525
```

```
<210> SEQ ID NO 38
<211> LENGTH: 119
<212> TYPE: PRT
<213> ORGANISM: Homo sapiens

<400> SEQUENCE: 38

Met Ser Arg Ser Val Ala Leu Ala Val Leu Ala Leu Leu Ser Leu Ser
1               5                   10                  15
Gly Leu Glu Ala Ile Gln Arg Thr Pro Lys Ile Gln Val Tyr Ser Arg
            20                  25                  30
His Pro Ala Glu Asn Gly Lys Ser Asn Phe Leu Asn Cys Tyr Val Ser
        35                  40                  45
Gly Phe His Pro Ser Asp Ile Glu Val Asp Leu Leu Lys Asn Gly Glu
    50                  55                  60
Arg Ile Glu Lys Val Glu His Ser Asp Leu Ser Phe Ser Lys Asp Trp
65                  70                  75                  80
Ser Phe Tyr Leu Leu Tyr Tyr Thr Glu Phe Thr Pro Thr Glu Lys Asp
                85                  90                  95
Glu Tyr Ala Cys Arg Val Asn His Val Thr Leu Ser Gln Pro Lys Ile
            100                 105                 110
Val Lys Trp Asp Arg Asp Met
        115
```

```
<210> SEQ ID NO 39
<211> LENGTH: 782
<212> TYPE: PRT
<213> ORGANISM: Homo sapiens

<400> SEQUENCE: 39

Met Ala Pro His Arg Pro Ala Pro Ala Leu Leu Cys Ala Leu Ser Leu
1               5                   10                  15
Ala Leu Cys Ala Leu Ser Leu Pro Val Arg Ala Ala Thr Ala Ser Arg
            20                  25                  30
```

-continued

```
Gly Ala Ser Gln Ala Gly Ala Pro Gln Gly Arg Val Pro Glu Ala Arg
         35                  40                  45
Pro Asn Ser Met Val Val Glu His Pro Glu Phe Leu Lys Ala Gly Lys
     50                  55                  60
Glu Pro Gly Leu Gln Ile Trp Arg Val Glu Lys Phe Asp Leu Val Pro
 65                  70                  75                  80
Val Pro Thr Asn Leu Tyr Gly Asp Phe Phe Thr Gly Asp Ala Tyr Val
                 85                  90                  95
Ile Leu Lys Thr Val Gln Leu Arg Asn Gly Asn Leu Gln Tyr Asp Leu
                100                 105                 110
His Tyr Trp Leu Gly Asn Glu Cys Ser Gln Asp Glu Ser Gly Ala Ala
                115                 120                 125
Ala Ile Phe Thr Val Gln Leu Asp Asp Tyr Leu Asn Gly Arg Ala Val
                130                 135                 140
Gln His Arg Glu Val Gln Gly Phe Glu Ser Ala Thr Phe Leu Gly Tyr
145                 150                 155                 160
Phe Lys Ser Gly Leu Lys Tyr Lys Lys Gly Val Ala Ser Gly Phe
                165                 170                 175
Lys His Val Val Pro Asn Glu Val Val Gln Arg Leu Phe Gln Val
                180                 185                 190
Lys Gly Arg Arg Val Val Arg Ala Thr Glu Val Pro Val Ser Trp Glu
                195                 200                 205
Ser Phe Asn Asn Gly Asp Cys Phe Ile Leu Asp Leu Gly Asn Asn Ile
    210                 215                 220
His Gln Trp Cys Gly Ser Asn Ser Asn Arg Tyr Glu Arg Leu Lys Ala
225                 230                 235                 240
Thr Gln Val Ser Lys Gly Ile Arg Asp Asn Glu Arg Ser Gly Arg Ala
                245                 250                 255
Arg Val His Val Ser Glu Glu Gly Thr Glu Pro Glu Ala Met Leu Gln
                260                 265                 270
Val Leu Gly Pro Lys Pro Ala Leu Pro Ala Gly Thr Glu Asp Thr Ala
                275                 280                 285
Lys Glu Asp Ala Ala Asn Arg Lys Leu Ala Lys Leu Tyr Lys Val Ser
    290                 295                 300
Asn Gly Ala Gly Thr Met Ser Val Ser Leu Val Ala Asp Glu Asn Pro
305                 310                 315                 320
Phe Ala Gln Gly Ala Leu Lys Ser Glu Asp Cys Phe Ile Leu Asp His
                325                 330                 335
Gly Lys Asp Gly Lys Ile Phe Val Trp Lys Gly Lys Gln Ala Asn Thr
                340                 345                 350
Glu Glu Arg Lys Ala Ala Leu Lys Thr Ala Ser Asp Phe Ile Thr Lys
                355                 360                 365
Met Asp Tyr Pro Lys Gln Thr Gln Val Ser Val Leu Pro Glu Gly Gly
    370                 375                 380
Glu Thr Pro Leu Phe Lys Gln Phe Phe Lys Asn Trp Arg Asp Pro Asp
385                 390                 395                 400
Gln Thr Asp Gly Leu Gly Leu Ser Tyr Leu Ser Ser His Ile Ala Asn
                405                 410                 415
Val Glu Arg Val Pro Phe Asp Ala Ala Thr Leu His Thr Ser Thr Ala
                420                 425                 430
Met Ala Ala Gln His Gly Met Asp Asp Asp Gly Thr Gly Gln Lys Gln
    435                 440                 445
```

```
Ile Trp Arg Ile Glu Gly Ser Asn Lys Val Pro Val Asp Pro Ala Thr
450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
        515                 520                 525

Gly Lys Glu Pro Ala His Leu Met Ser Leu Phe Gly Gly Lys Pro Met
    530                 535                 540

Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
        595                 600                 605

Gly Ala Ser Glu Ala Glu Lys Thr Gly Ala Gln Glu Leu Leu Arg Val
    610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
        675                 680                 685

Met Gln Glu Asp Leu Ala Thr Asp Asp Val Met Leu Leu Asp Thr Trp
    690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
        755                 760                 765

Ser Val Asp Pro Leu Asp Arg Ala Met Ala Glu Leu Ala Ala
    770                 775                 780

<210> SEQ ID NO 40
<211> LENGTH: 638
<212> TYPE: PRT
<213> ORGANISM: Homo sapiens

<400> SEQUENCE: 40

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gly Tyr Cys Gln
        35                  40                  45
```

-continued

```
Met Arg Cys Thr Phe His Pro Arg Cys Leu Leu Phe Ser Phe Leu Pro
    50                  55                  60
Ala Ser Ser Ile Asn Asp Met Glu Lys Arg Phe Gly Cys Phe Leu Lys
65                  70                  75                  80
Asp Ser Val Thr Gly Thr Leu Pro Lys Val His Arg Thr Gly Ala Val
                85                  90                  95
Ser Gly His Ser Leu Lys Gln Cys Gly His Gln Ile Ser Ala Cys His
            100                 105                 110
Arg Asp Ile Tyr Lys Gly Val Asp Met Arg Gly Val Asn Phe Asn Val
        115                 120                 125
Ser Lys Val Ser Ser Val Glu Glu Cys Gln Lys Arg Cys Thr Asn Asn
    130                 135                 140
Ile Arg Cys Gln Phe Phe Ser Tyr Ala Thr Gln Thr Phe His Lys Ala
145                 150                 155                 160
Glu Tyr Arg Asn Asn Cys Leu Leu Lys Tyr Ser Pro Gly Gly Thr Pro
                165                 170                 175
Thr Ala Ile Lys Val Leu Ser Asn Val Glu Ser Gly Phe Ser Leu Lys
            180                 185                 190
Pro Cys Ala Leu Ser Glu Ile Gly Cys His Met Asn Ile Phe Gln His
        195                 200                 205
Leu Ala Phe Ser Asp Val Asp Val Ala Arg Val Leu Thr Pro Asp Ala
    210                 215                 220
Phe Val Cys Arg Thr Ile Cys Thr Tyr His Pro Asn Cys Leu Phe Phe
225                 230                 235                 240
Thr Phe Tyr Thr Asn Val Trp Lys Ile Glu Ser Gln Arg Asn Val Cys
                245                 250                 255
Leu Leu Lys Thr Ser Glu Ser Gly Thr Pro Ser Ser Ser Thr Pro Gln
            260                 265                 270
Glu Asn Thr Ile Ser Gly Tyr Ser Leu Leu Thr Cys Lys Arg Thr Leu
        275                 280                 285
Pro Glu Pro Cys His Ser Lys Ile Tyr Pro Gly Val Asp Phe Gly Gly
    290                 295                 300
Glu Glu Leu Asn Val Thr Phe Val Lys Gly Val Asn Val Cys Gln Glu
305                 310                 315                 320
Thr Cys Thr Lys Met Ile Arg Cys Gln Phe Phe Thr Tyr Ser Leu Leu
                325                 330                 335
Pro Glu Asp Cys Lys Glu Glu Lys Cys Lys Cys Phe Leu Arg Leu Ser
            340                 345                 350
Met Asp Gly Ser Pro Thr Arg Ile Ala Tyr Gly Thr Gln Gly Ser Ser
        355                 360                 365
Gly Tyr Ser Leu Arg Leu Cys Asn Thr Gly Asp Asn Ser Val Cys Thr
    370                 375                 380
Thr Lys Thr Ser Thr Arg Ile Val Gly Gly Thr Asn Ser Ser Trp Gly
385                 390                 395                 400
Glu Trp Pro Trp Gln Val Ser Leu Gln Val Lys Leu Thr Ala Gln Arg
                405                 410                 415
His Leu Cys Gly Gly Ser Leu Ile Gly His Gln Trp Val Leu Thr Ala
            420                 425                 430
Ala His Cys Phe Asp Gly Leu Pro Leu Gln Asp Val Trp Arg Ile Tyr
        435                 440                 445
Ser Gly Ile Leu Asn Leu Ser Asp Ile Thr Lys Asp Thr Pro Phe Ser
    450                 455                 460
```

```
Gln Ile Lys Glu Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
            485                 490                 495

Glu Phe Gln Lys Pro Ile Cys Leu Pro Ser Lys Gly Asp Thr Ser Thr
            500                 505                 510

Ile Tyr Thr Asn Cys Trp Val Thr Gly Trp Gly Phe Ser Lys Glu Lys
            515                 520                 525

Gly Glu Ile Gln Asn Ile Leu Gln Lys Val Asn Ile Pro Leu Val Thr
            530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Gly Lys Asp Ala Cys Lys Gly
                565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
            595                 600                 605

Gly Val Tyr Thr Lys Val Ala Glu Tyr Met Asp Trp Ile Leu Glu Lys
            610                 615                 620

Thr Gln Ser Ser Asp Gly Lys Ala Gln Met Gln Ser Pro Ala
625                 630                 635

<210> SEQ ID NO 41
<211> LENGTH: 291
<212> TYPE: PRT
<213> ORGANISM: Homo sapiens

<400> SEQUENCE: 41

Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Glu Asp Arg
130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205
```

```
Glu Tyr Gly Pro Cys Arg Arg Glu Met Glu Asp Thr Leu Asn His Leu
        210                 215                 220
Lys Phe Leu Asn Val Leu Ser Pro Arg Gly Val His Ile Pro Asn Cys
225                 230                 235                 240
Asp Lys Lys Gly Phe Tyr Lys Lys Gln Cys Arg Pro Ser Lys Gly
                245                 250                 255
Arg Lys Arg Gly Phe Cys Trp Cys Val Asp Lys Tyr Gly Gln Pro Leu
            260                 265                 270
Pro Gly Tyr Thr Thr Lys Gly Lys Glu Asp Val His Cys Tyr Ser Met
            275                 280                 285
Gln Ser Lys
        290

<210> SEQ ID NO 42
<211> LENGTH: 462
<212> TYPE: PRT
<213> ORGANISM: Homo sapiens

<400> SEQUENCE: 42

Met Ala Arg Val Leu Gly Ala Pro Val Ala Leu Gly Leu Trp Ser Leu
1               5                   10                  15
Cys Trp Ser Leu Ala Ile Ala Thr Pro Leu Pro Pro Thr Ser Ala His
            20                  25                  30
Gly Asn Val Ala Glu Gly Glu Thr Lys Pro Asp Pro Asp Val Thr Glu
        35                  40                  45
Arg Cys Ser Asp Gly Trp Ser Phe Asp Ala Thr Thr Leu Asp Asp Asn
    50                  55                  60
Gly Thr Met Leu Phe Phe Lys Gly Glu Phe Val Trp Lys Ser His Lys
65                  70                  75                  80
Trp Asp Arg Glu Leu Ile Ser Glu Arg Trp Lys Asn Phe Pro Ser Pro
                85                  90                  95
Val Asp Ala Ala Phe Arg Gln Gly His Asn Ser Val Phe Leu Ile Lys
            100                 105                 110
Gly Asp Lys Val Trp Val Tyr Pro Pro Glu Lys Lys Glu Lys Gly Tyr
        115                 120                 125
Pro Lys Leu Leu Gln Asp Glu Phe Pro Gly Ile Pro Ser Pro Leu Asp
    130                 135                 140
Ala Ala Val Glu Cys His Arg Gly Glu Cys Gln Ala Glu Gly Val Leu
145                 150                 155                 160
Phe Phe Gln Gly Asp Arg Glu Trp Phe Trp Asp Leu Ala Thr Gly Thr
                165                 170                 175
Met Lys Glu Arg Ser Trp Pro Ala Val Gly Asn Cys Ser Ser Ala Leu
            180                 185                 190
Arg Trp Leu Gly Arg Tyr Tyr Cys Phe Gln Gly Asn Gln Phe Leu Arg
        195                 200                 205
Phe Asp Pro Val Arg Gly Glu Val Pro Pro Arg Tyr Pro Arg Asp Val
    210                 215                 220
Arg Asp Tyr Phe Met Pro Cys Pro Gly Arg Gly His Gly His Arg Asn
225                 230                 235                 240
Gly Thr Gly His Gly Asn Ser Thr His His Gly Pro Glu Tyr Met Arg
                245                 250                 255
Cys Ser Pro His Leu Val Leu Ser Ala Leu Thr Ser Asp Asn His Gly
            260                 265                 270
Ala Thr Tyr Ala Phe Ser Gly Thr His Tyr Trp Arg Leu Asp Thr Ser
```

```
                275                 280                 285
    Arg Asp Gly Trp His Ser Trp Pro Ile Ala His Gln Trp Pro Gln Gly
        290                 295                 300

Pro Ser Ala Val Asp Ala Ala Phe Ser Trp Glu Glu Lys Leu Tyr Leu
    305                 310                 315                 320

Val Gln Gly Thr Gln Val Tyr Val Phe Leu Thr Lys Gly Gly Tyr Thr
                    325                 330                 335

Leu Val Ser Gly Tyr Pro Lys Arg Leu Glu Lys Glu Val Gly Thr Pro
                340                 345                 350

His Gly Ile Ile Leu Asp Ser Val Asp Ala Ala Phe Ile Cys Pro Gly
                355                 360                 365

Ser Ser Arg Leu His Ile Met Ala Gly Arg Arg Leu Trp Trp Leu Asp
            370                 375                 380

Leu Lys Ser Gly Ala Gln Ala Thr Trp Thr Glu Leu Pro Trp Pro His
    385                 390                 395                 400

Glu Lys Val Asp Gly Ala Leu Cys Met Glu Lys Ser Leu Gly Pro Asn
                    405                 410                 415

Ser Cys Ser Ala Asn Gly Pro Gly Leu Tyr Leu Ile His Gly Pro Asn
                420                 425                 430

Leu Tyr Cys Tyr Ser Asp Val Glu Lys Leu Asn Ala Ala Lys Ala Leu
                435                 440                 445

Pro Gln Pro Gln Asn Val Thr Ser Leu Leu Gly Cys Thr His
        450                 455                 460

<210> SEQ ID NO 43
<211> LENGTH: 12
<212> TYPE: PRT
<213> ORGANISM: Homo sapiens

<400> SEQUENCE: 43

Ile Asp Ala Val Tyr Glu Ala Pro Gln Glu Glu Lys
1               5                   10

<210> SEQ ID NO 44
<211> LENGTH: 19
<212> TYPE: PRT
<213> ORGANISM: Homo sapiens

<400> SEQUENCE: 44

Ile Ile Gly Tyr Thr Pro Asp Leu Asp Pro Glu Thr Val Asp Asp Ala
1               5                   10                  15

Phe Ala Arg

<210> SEQ ID NO 45
<211> LENGTH: 11
<212> TYPE: PRT
<213> ORGANISM: Homo sapiens

<400> SEQUENCE: 45

Asp Ser Tyr Val Gly Asp Glu Ala Gln Ser Lys
1               5                   10

<210> SEQ ID NO 46
<211> LENGTH: 16
<212> TYPE: PRT
<213> ORGANISM: Homo sapiens

<400> SEQUENCE: 46

Ser Tyr Glu Leu Pro Asp Gly Gln Val Ile Thr Ile Gly Asn Glu Arg
```

```
<210> SEQ ID NO 47
<211> LENGTH: 12
<212> TYPE: PRT
<213> ORGANISM: Homo sapiens

<400> SEQUENCE: 47

Thr Ser Leu Gly Ser Asp Ser Ser Thr Gln Ala Lys
1               5                   10

<210> SEQ ID NO 48
<211> LENGTH: 15
<212> TYPE: PRT
<213> ORGANISM: Homo sapiens

<400> SEQUENCE: 48

Gly Asp Ile Gly Glu Thr Gly Val Pro Gly Ala Glu Gly Pro Arg
1               5                   10                  15

<210> SEQ ID NO 49
<211> LENGTH: 15
<212> TYPE: PRT
<213> ORGANISM: Homo sapiens

<400> SEQUENCE: 49

Ile Phe Tyr Asn Gln Gln Asn His Tyr Asp Gly Ser Thr Gly Lys
1               5                   10                  15

<210> SEQ ID NO 50
<211> LENGTH: 16
<212> TYPE: PRT
<213> ORGANISM: Homo sapiens

<400> SEQUENCE: 50

Ile Ala Pro Gln Leu Ser Thr Glu Glu Leu Val Ser Leu Gly Glu Lys
1               5                   10                  15

<210> SEQ ID NO 51
<211> LENGTH: 9
<212> TYPE: PRT
<213> ORGANISM: Homo sapiens

<400> SEQUENCE: 51

Leu Pro Asn Asn Val Leu Gln Glu Lys
1               5

<210> SEQ ID NO 52
<211> LENGTH: 19
<212> TYPE: PRT
<213> ORGANISM: Homo sapiens

<400> SEQUENCE: 52

Ala Val Leu Asp Val Phe Glu Glu Gly Thr Glu Ala Ser Ala Ala Thr
1               5                   10                  15

Ala Val Lys

<210> SEQ ID NO 53
<211> LENGTH: 10
<212> TYPE: PRT
<213> ORGANISM: Homo sapiens

<400> SEQUENCE: 53

Asn Leu Ala Val Ser Gln Val Val His Lys
```

```
1               5                   10

<210> SEQ ID NO 54
<211> LENGTH: 14
<212> TYPE: PRT
<213> ORGANISM: Homo sapiens

<400> SEQUENCE: 54

Ile Thr Pro Asn Leu Ala Glu Phe Ala Phe Ser Leu Tyr Arg
1               5                   10

<210> SEQ ID NO 55
<211> LENGTH: 10
<212> TYPE: PRT
<213> ORGANISM: Homo sapiens

<400> SEQUENCE: 55

Leu Ser Ile Thr Gly Thr Tyr Asp Leu Lys
1               5                   10

<210> SEQ ID NO 56
<211> LENGTH: 11
<212> TYPE: PRT
<213> ORGANISM: Homo sapiens

<400> SEQUENCE: 56

Ala Thr Trp Ser Gly Ala Val Leu Ala Gly Arg
1               5                   10

<210> SEQ ID NO 57
<211> LENGTH: 10
<212> TYPE: PRT
<213> ORGANISM: Homo sapiens

<400> SEQUENCE: 57

Leu Glu Thr Pro Asp Phe Gln Leu Phe Lys
1               5                   10

<210> SEQ ID NO 58
<211> LENGTH: 7
<212> TYPE: PRT
<213> ORGANISM: Homo sapiens

<400> SEQUENCE: 58

Asp Phe Leu Gln Ser Leu Lys
1               5

<210> SEQ ID NO 59
<211> LENGTH: 13
<212> TYPE: PRT
<213> ORGANISM: Homo sapiens

<400> SEQUENCE: 59

Leu Gly Asn Gln Glu Pro Gly Gly Gln Thr Ala Leu Lys
1               5                   10

<210> SEQ ID NO 60
<211> LENGTH: 10
<212> TYPE: PRT
<213> ORGANISM: Homo sapiens

<400> SEQUENCE: 60

Ala Pro His Gly Pro Gly Leu Ile Tyr Arg
1               5                   10
```

<210> SEQ ID NO 61
<211> LENGTH: 10
<212> TYPE: PRT
<213> ORGANISM: Homo sapiens

<400> SEQUENCE: 61

His Thr Leu Asn Gln Ile Asp Glu Val Lys
1               5                   10

<210> SEQ ID NO 62
<211> LENGTH: 18
<212> TYPE: PRT
<213> ORGANISM: Homo sapiens

<400> SEQUENCE: 62

Leu Leu Ile Tyr Ala Val Leu Pro Thr Gly Asp Val Ile Gly Asp Ser
1               5                   10                  15

Ala Lys

<210> SEQ ID NO 63
<211> LENGTH: 14
<212> TYPE: PRT
<213> ORGANISM: Homo sapiens

<400> SEQUENCE: 63

Thr Glu His Pro Phe Thr Val Glu Glu Phe Val Leu Pro Lys
1               5                   10

<210> SEQ ID NO 64
<211> LENGTH: 12
<212> TYPE: PRT
<213> ORGANISM: Homo sapiens

<400> SEQUENCE: 64

Ala Leu Gln Asp Gln Leu Val Leu Val Ala Ala Lys
1               5                   10

<210> SEQ ID NO 65
<211> LENGTH: 11
<212> TYPE: PRT
<213> ORGANISM: Homo sapiens

<400> SEQUENCE: 65

Asp Asp Leu Tyr Val Ser Asp Ala Phe His Lys
1               5                   10

<210> SEQ ID NO 66
<211> LENGTH: 13
<212> TYPE: PRT
<213> ORGANISM: Homo sapiens

<400> SEQUENCE: 66

Phe Ala Thr Thr Phe Tyr Gln His Leu Ala Asp Ser Lys
1               5                   10

<210> SEQ ID NO 67
<211> LENGTH: 11
<212> TYPE: PRT
<213> ORGANISM: Homo sapiens

<400> SEQUENCE: 67

Ala Thr Glu His Leu Ser Thr Leu Ser Glu Lys
1               5                   10

<210> SEQ ID NO 68
<211> LENGTH: 9
<212> TYPE: PRT
<213> ORGANISM: Homo sapiens

<400> SEQUENCE: 68

Ser Pro Glu Leu Gln Ala Glu Ala Lys
1               5

<210> SEQ ID NO 69
<211> LENGTH: 12
<212> TYPE: PRT
<213> ORGANISM: Homo sapiens

<400> SEQUENCE: 69

Ser Leu Ala Pro Tyr Ala Gln Asp Thr Gln Glu Lys
1               5                   10

<210> SEQ ID NO 70
<211> LENGTH: 9
<212> TYPE: PRT
<213> ORGANISM: Homo sapiens

<400> SEQUENCE: 70

Phe Pro Glu Val Asp Val Leu Thr Lys
1               5

<210> SEQ ID NO 71
<211> LENGTH: 19
<212> TYPE: PRT
<213> ORGANISM: Homo sapiens

<400> SEQUENCE: 71

Ile Leu Gly Glu Glu Leu Gly Phe Ala Ser Leu His Asp Leu Gln Leu
1               5                   10                  15

Leu Gly Lys

<210> SEQ ID NO 72
<211> LENGTH: 9
<212> TYPE: PRT
<213> ORGANISM: Homo sapiens

<400> SEQUENCE: 72

Thr Ala Ala Gln Asn Leu Tyr Glu Lys
1               5

<210> SEQ ID NO 73
<211> LENGTH: 9
<212> TYPE: PRT
<213> ORGANISM: Homo sapiens

<400> SEQUENCE: 73

Thr Tyr Leu Pro Ala Val Asp Glu Lys
1               5

<210> SEQ ID NO 74
<211> LENGTH: 12
<212> TYPE: PRT
<213> ORGANISM: Homo sapiens

<400> SEQUENCE: 74

Phe Ser Glu Phe Trp Asp Leu Asp Pro Glu Val Arg
1               5                   10

```
<210> SEQ ID NO 75
<211> LENGTH: 11
<212> TYPE: PRT
<213> ORGANISM: Homo sapiens

<400> SEQUENCE: 75

Gly Trp Val Thr Asp Gly Phe Ser Ser Leu Lys
1               5                   10

<210> SEQ ID NO 76
<211> LENGTH: 15
<212> TYPE: PRT
<213> ORGANISM: Homo sapiens

<400> SEQUENCE: 76

Val Thr Glu Pro Ile Ser Ala Glu Ser Gly Glu Gln Val Glu Arg
1               5                   10                  15

<210> SEQ ID NO 77
<211> LENGTH: 13
<212> TYPE: PRT
<213> ORGANISM: Homo sapiens

<400> SEQUENCE: 77

Trp Trp Thr Gln Ala Gln Ala His Asp Leu Val Ile Lys
1               5                   10

<210> SEQ ID NO 78
<211> LENGTH: 14
<212> TYPE: PRT
<213> ORGANISM: Homo sapiens

<400> SEQUENCE: 78

Phe Val Thr Val Gln Thr Ile Ser Gly Thr Gly Ala Leu Arg
1               5                   10

<210> SEQ ID NO 79
<211> LENGTH: 9
<212> TYPE: PRT
<213> ORGANISM: Homo sapiens

<400> SEQUENCE: 79

Ala Thr Val Val Tyr Gln Gly Glu Arg
1               5

<210> SEQ ID NO 80
<211> LENGTH: 17
<212> TYPE: PRT
<213> ORGANISM: Homo sapiens

<400> SEQUENCE: 80

Pro Asp Asn Gly Phe Val Asn Tyr Pro Ala Lys Pro Thr Leu Tyr Tyr
1               5                   10                  15

Lys

<210> SEQ ID NO 81
<211> LENGTH: 6
<212> TYPE: PRT
<213> ORGANISM: Homo sapiens

<400> SEQUENCE: 81

Ile Gln Val Tyr Ser Arg
1               5
```

```
<210> SEQ ID NO 82
<211> LENGTH: 10
<212> TYPE: PRT
<213> ORGANISM: Homo sapiens

<400> SEQUENCE: 82

Val Asn His Val Thr Leu Ser Gln Pro Lys
1               5                   10

<210> SEQ ID NO 83
<211> LENGTH: 11
<212> TYPE: PRT
<213> ORGANISM: Homo sapiens

<400> SEQUENCE: 83

Ala Leu Glu Gln Asp Leu Pro Val Asn Ile Lys
1               5                   10

<210> SEQ ID NO 84
<211> LENGTH: 20
<212> TYPE: PRT
<213> ORGANISM: Homo sapiens

<400> SEQUENCE: 84

Ser Val Val Leu Ile Pro Leu Gly Ala Val Asp Asp Gly Glu His Ser
1               5                   10                  15

Gln Asn Glu Lys
            20

<210> SEQ ID NO 85
<211> LENGTH: 6
<212> TYPE: PRT
<213> ORGANISM: Homo sapiens

<400> SEQUENCE: 85

Ala Phe Val Phe Pro Lys
1               5

<210> SEQ ID NO 86
<211> LENGTH: 10
<212> TYPE: PRT
<213> ORGANISM: Homo sapiens

<400> SEQUENCE: 86

Glu Ser Asp Thr Ser Tyr Val Ser Leu Lys
1               5                   10

<210> SEQ ID NO 87
<211> LENGTH: 11
<212> TYPE: PRT
<213> ORGANISM: Homo sapiens

<400> SEQUENCE: 87

Glu Asp Val Tyr Val Val Gly Thr Val Leu Arg
1               5                   10

<210> SEQ ID NO 88
<211> LENGTH: 12
<212> TYPE: PRT
<213> ORGANISM: Homo sapiens

<400> SEQUENCE: 88

Leu Ser Leu Glu Ile Glu Gln Leu Glu Leu Gln Arg
1               5                   10
```

```
<210> SEQ ID NO 89
<211> LENGTH: 8
<212> TYPE: PRT
<213> ORGANISM: Homo sapiens

<400> SEQUENCE: 89

Tyr Glu Ile Val Val Glu Ala Arg
1               5

<210> SEQ ID NO 90
<211> LENGTH: 10
<212> TYPE: PRT
<213> ORGANISM: Homo sapiens

<400> SEQUENCE: 90

Tyr Thr Phe Val Val Pro Glu Asp Thr Arg
1               5                   10

<210> SEQ ID NO 91
<211> LENGTH: 14
<212> TYPE: PRT
<213> ORGANISM: Homo sapiens

<400> SEQUENCE: 91

Glu Ser Ile Ser Val Ser Ser Glu Gln Leu Ala Gln Phe Arg
1               5                   10

<210> SEQ ID NO 92
<211> LENGTH: 9
<212> TYPE: PRT
<213> ORGANISM: Homo sapiens

<400> SEQUENCE: 92

Val Leu Asp Ala Leu Gln Ala Ile Lys
1               5

<210> SEQ ID NO 93
<211> LENGTH: 15
<212> TYPE: PRT
<213> ORGANISM: Homo sapiens

<400> SEQUENCE: 93

Glu Ala Leu Ile Gln Phe Leu Glu Gln Val His Gln Gly Ile Lys
1               5                   10                  15

<210> SEQ ID NO 94
<211> LENGTH: 9
<212> TYPE: PRT
<213> ORGANISM: Homo sapiens

<400> SEQUENCE: 94

Ile Val Gln Leu Ile Gln Asp Thr Arg
1               5

<210> SEQ ID NO 95
<211> LENGTH: 7
<212> TYPE: PRT
<213> ORGANISM: Homo sapiens

<400> SEQUENCE: 95

Leu Val Gly Gly Leu His Arg
1               5
```

```
<210> SEQ ID NO 96
<211> LENGTH: 13
<212> TYPE: PRT
<213> ORGANISM: Homo sapiens

<400> SEQUENCE: 96

Gly Ala Tyr Pro Leu Ser Ile Glu Pro Ile Gly Val Arg
1               5                   10

<210> SEQ ID NO 97
<211> LENGTH: 10
<212> TYPE: PRT
<213> ORGANISM: Homo sapiens

<400> SEQUENCE: 97

Ile Tyr His Ser His Ile Asp Ala Pro Lys
1               5                   10

<210> SEQ ID NO 98
<211> LENGTH: 11
<212> TYPE: PRT
<213> ORGANISM: Homo sapiens

<400> SEQUENCE: 98

Glu Leu Asp Glu Ser Leu Gln Val Ala Glu Arg
1               5                   10

<210> SEQ ID NO 99
<211> LENGTH: 16
<212> TYPE: PRT
<213> ORGANISM: Homo sapiens

<400> SEQUENCE: 99

Glu Pro Gln Asp Thr Tyr His Tyr Leu Pro Phe Ser Leu Pro His Arg
1               5                   10                  15

<210> SEQ ID NO 100
<211> LENGTH: 14
<212> TYPE: PRT
<213> ORGANISM: Homo sapiens

<400> SEQUENCE: 100

Leu Ala Asn Leu Thr Gln Gly Glu Asp Gln Tyr Tyr Leu Arg
1               5                   10

<210> SEQ ID NO 101
<211> LENGTH: 9
<212> TYPE: PRT
<213> ORGANISM: Homo sapiens

<400> SEQUENCE: 101

Ser Ala Leu Val Leu Gln Tyr Leu Arg
1               5

<210> SEQ ID NO 102
<211> LENGTH: 8
<212> TYPE: PRT
<213> ORGANISM: Homo sapiens

<400> SEQUENCE: 102

Val Ser Val Ser Gln Thr Ser Lys
1               5

<210> SEQ ID NO 103
<211> LENGTH: 10
```

```
<212> TYPE: PRT
<213> ORGANISM: Homo sapiens

<400> SEQUENCE: 103

Ala Glu Val Asp Asp Val Ile Gln Val Arg
1               5                   10

<210> SEQ ID NO 104
<211> LENGTH: 23
<212> TYPE: PRT
<213> ORGANISM: Homo sapiens

<400> SEQUENCE: 104

Val Ala Gln Val Ile Ile Pro Ser Thr Tyr Val Pro Gly Thr Thr Asn
1               5                   10                  15

His Asp Ile Ala Leu Leu Arg
            20

<210> SEQ ID NO 105
<211> LENGTH: 10
<212> TYPE: PRT
<213> ORGANISM: Homo sapiens

<400> SEQUENCE: 105

Val Ser Gln Tyr Ile Glu Trp Leu Gln Lys
1               5                   10

<210> SEQ ID NO 106
<211> LENGTH: 20
<212> TYPE: PRT
<213> ORGANISM: Homo sapiens

<400> SEQUENCE: 106

Asn Leu Phe Leu Thr Asn Leu Asp Asn Leu His Glu Asn Asn Thr His
1               5                   10                  15

Asn Gln Glu Lys
            20

<210> SEQ ID NO 107
<211> LENGTH: 11
<212> TYPE: PRT
<213> ORGANISM: Homo sapiens

<400> SEQUENCE: 107

Glu Thr Tyr Asp Phe Asp Ile Ala Val Leu Arg
1               5                   10

<210> SEQ ID NO 108
<211> LENGTH: 9
<212> TYPE: PRT
<213> ORGANISM: Homo sapiens

<400> SEQUENCE: 108

Thr Gly Ile Val Ser Gly Phe Gly Arg
1               5

<210> SEQ ID NO 109
<211> LENGTH: 18
<212> TYPE: PRT
<213> ORGANISM: Homo sapiens

<400> SEQUENCE: 109

Leu His Glu Ala Phe Ser Pro Val Ser Tyr Gln His Asp Leu Ala Leu
1               5                   10                  15
```

Leu Arg

<210> SEQ ID NO 110
<211> LENGTH: 9
<212> TYPE: PRT
<213> ORGANISM: Homo sapiens

<400> SEQUENCE: 110

Val Val Gly Gly Leu Val Ala Leu Arg
1               5

<210> SEQ ID NO 111
<211> LENGTH: 25
<212> TYPE: PRT
<213> ORGANISM: Homo sapiens

<400> SEQUENCE: 111

Ala Val Pro Pro Asn Asn Ser Asn Ala Ala Glu Asp Asp Leu Pro Thr
1               5                   10                  15

Val Glu Leu Gln Gly Val Val Pro Arg
            20                  25

<210> SEQ ID NO 112
<211> LENGTH: 12
<212> TYPE: PRT
<213> ORGANISM: Homo sapiens

<400> SEQUENCE: 112

Ser Thr Val Leu Thr Ile Pro Glu Ile Ile Ile Lys
1               5                   10

<210> SEQ ID NO 113
<211> LENGTH: 9
<212> TYPE: PRT
<213> ORGANISM: Homo sapiens

<400> SEQUENCE: 113

Ile Gln Thr His Ser Thr Thr Tyr Arg
1               5

<210> SEQ ID NO 114
<211> LENGTH: 11
<212> TYPE: PRT
<213> ORGANISM: Homo sapiens

<400> SEQUENCE: 114

Leu Ile Glu Asn Gly Tyr Phe His Pro Val Lys
1               5                   10

<210> SEQ ID NO 115
<211> LENGTH: 7
<212> TYPE: PRT
<213> ORGANISM: Homo sapiens

<400> SEQUENCE: 115

Pro Ala Phe Ser Ala Ile Arg
1               5

<210> SEQ ID NO 116
<211> LENGTH: 10
<212> TYPE: PRT
<213> ORGANISM: Homo sapiens

<400> SEQUENCE: 116

Ser Leu Gly Phe Cys Asp Thr Thr Asn Lys
1               5                   10

<210> SEQ ID NO 117
<211> LENGTH: 9
<212> TYPE: PRT
<213> ORGANISM: Homo sapiens

<400> SEQUENCE: 117

Phe Gln Ser Val Phe Thr Val Thr Arg
1               5

<210> SEQ ID NO 118
<211> LENGTH: 12
<212> TYPE: PRT
<213> ORGANISM: Homo sapiens

<400> SEQUENCE: 118

Thr Asn Gln Val Asn Ser Gly Gly Val Leu Leu Arg
1               5                   10

<210> SEQ ID NO 119
<211> LENGTH: 7
<212> TYPE: PRT
<213> ORGANISM: Homo sapiens

<400> SEQUENCE: 119

Gly Leu Thr Leu His Leu Lys
1               5

<210> SEQ ID NO 120
<211> LENGTH: 7
<212> TYPE: PRT
<213> ORGANISM: Homo sapiens

<400> SEQUENCE: 120

Gly Tyr Gly Phe Tyr Thr Lys
1               5

<210> SEQ ID NO 121
<211> LENGTH: 7
<212> TYPE: PRT
<213> ORGANISM: Homo sapiens

<400> SEQUENCE: 121

Ser Tyr Pro Pro Asp Leu Arg
1               5

<210> SEQ ID NO 122
<211> LENGTH: 18
<212> TYPE: PRT
<213> ORGANISM: Homo sapiens

<400> SEQUENCE: 122

Thr Leu Asp Glu Phe Thr Ile Ile Gln Asn Leu Gln Pro Gln Tyr Gln
1               5                   10                  15

Phe Arg

<210> SEQ ID NO 123
<211> LENGTH: 8
<212> TYPE: PRT
<213> ORGANISM: Homo sapiens

<400> SEQUENCE: 123

Val Ser Val His Pro Asp Tyr Arg
1               5

<210> SEQ ID NO 124
<211> LENGTH: 8
<212> TYPE: PRT
<213> ORGANISM: Homo sapiens

<400> SEQUENCE: 124

Ser Asp Phe Ser Asn Glu Glu Arg
1               5

<210> SEQ ID NO 125
<211> LENGTH: 11
<212> TYPE: PRT
<213> ORGANISM: Homo sapiens

<400> SEQUENCE: 125

Thr Asn Phe Asp Asn Asp Ile Ala Leu Val Arg
1               5                   10

<210> SEQ ID NO 126
<211> LENGTH: 9
<212> TYPE: PRT
<213> ORGANISM: Homo sapiens

<400> SEQUENCE: 126

Asp His Glu Asn Glu Leu Leu Asn Lys
1               5

<210> SEQ ID NO 127
<211> LENGTH: 9
<212> TYPE: PRT
<213> ORGANISM: Homo sapiens

<400> SEQUENCE: 127

His Ala Phe Ile Leu Gln Asp Thr Lys
1               5

<210> SEQ ID NO 128
<211> LENGTH: 9
<212> TYPE: PRT
<213> ORGANISM: Homo sapiens

<400> SEQUENCE: 128

Thr Gly Leu Gln Glu Val Glu Val Lys
1               5

<210> SEQ ID NO 129
<211> LENGTH: 9
<212> TYPE: PRT
<213> ORGANISM: Homo sapiens

<400> SEQUENCE: 129

Asp His Ala Val Asp Leu Ile Gln Lys
1               5

<210> SEQ ID NO 130
<211> LENGTH: 10
<212> TYPE: PRT
<213> ORGANISM: Homo sapiens

<400> SEQUENCE: 130

Val Gly Asp Thr Leu Asn Leu Asn Leu Arg

<210> SEQ ID NO 131
<211> LENGTH: 15
<212> TYPE: PRT
<213> ORGANISM: Homo sapiens

<400> SEQUENCE: 131

Val Leu Ser Leu Ala Gln Glu Gln Val Gly Gly Ser Pro Glu Lys
1               5                   10                  15

<210> SEQ ID NO 132
<211> LENGTH: 9
<212> TYPE: PRT
<213> ORGANISM: Homo sapiens

<400> SEQUENCE: 132

Gly Phe Val Val Ala Gly Pro Ser Arg
1               5

<210> SEQ ID NO 133
<211> LENGTH: 15
<212> TYPE: PRT
<213> ORGANISM: Homo sapiens

<400> SEQUENCE: 133

Glu Leu Ser His Leu Pro Ser Leu Tyr Asp Tyr Ser Ala Tyr Arg
1               5                   10                  15

<210> SEQ ID NO 134
<211> LENGTH: 20
<212> TYPE: PRT
<213> ORGANISM: Homo sapiens

<400> SEQUENCE: 134

Leu Ile Asp Gln Tyr Gly Thr His Tyr Leu Gln Ser Gly Ser Leu Gly
1               5                   10                  15

Gly Glu Tyr Arg
            20

<210> SEQ ID NO 135
<211> LENGTH: 11
<212> TYPE: PRT
<213> ORGANISM: Homo sapiens

<400> SEQUENCE: 135

Ser Tyr Thr Ser His Thr Asn Glu Ile His Lys
1               5                   10

<210> SEQ ID NO 136
<211> LENGTH: 15
<212> TYPE: PRT
<213> ORGANISM: Homo sapiens

<400> SEQUENCE: 136

Ser Leu Pro Val Ser Asp Ser Val Leu Ser Gly Phe Glu Gln Arg
1               5                   10                  15

<210> SEQ ID NO 137
<211> LENGTH: 16
<212> TYPE: PRT
<213> ORGANISM: Homo sapiens

<400> SEQUENCE: 137

Val Gln Glu Ala His Leu Thr Glu Asp Gln Ile Phe Tyr Phe Pro Lys
1               5                   10                  15

<210> SEQ ID NO 138
<211> LENGTH: 11
<212> TYPE: PRT
<213> ORGANISM: Homo sapiens

<400> SEQUENCE: 138

Leu Ser Pro Ile Tyr Asn Leu Val Pro Val Lys
1               5                   10

<210> SEQ ID NO 139
<211> LENGTH: 9
<212> TYPE: PRT
<213> ORGANISM: Homo sapiens

<400> SEQUENCE: 139

Val Val Glu Glu Ser Glu Leu Ala Arg
1               5

<210> SEQ ID NO 140
<211> LENGTH: 10
<212> TYPE: PRT
<213> ORGANISM: Homo sapiens

<400> SEQUENCE: 140

Glu Glu Leu Leu Pro Ala Gln Asp Ile Lys
1               5                   10

<210> SEQ ID NO 141
<211> LENGTH: 10
<212> TYPE: PRT
<213> ORGANISM: Homo sapiens

<400> SEQUENCE: 141

Thr His His Asp Gly Ala Ile Thr Glu Arg
1               5                   10

<210> SEQ ID NO 142
<211> LENGTH: 12
<212> TYPE: PRT
<213> ORGANISM: Homo sapiens

<400> SEQUENCE: 142

Ser Ser Asn Leu Ile Ile Leu Glu Glu His Leu Lys
1               5                   10

<210> SEQ ID NO 143
<211> LENGTH: 11
<212> TYPE: PRT
<213> ORGANISM: Homo sapiens

<400> SEQUENCE: 143

Ser Ser Gln Glu Ser Tyr Ala His Gly Thr Lys
1               5                   10

<210> SEQ ID NO 144
<211> LENGTH: 13
<212> TYPE: PRT
<213> ORGANISM: Homo sapiens

<400> SEQUENCE: 144

His Gly Asn Thr Asp Ser Glu Gly Ile Val Glu Val Lys
1               5                   10

```
<210> SEQ ID NO 145
<211> LENGTH: 8
<212> TYPE: PRT
<213> ORGANISM: Homo sapiens

<400> SEQUENCE: 145

Ile Val Ile Glu Tyr Val Asp Arg
1               5

<210> SEQ ID NO 146
<211> LENGTH: 14
<212> TYPE: PRT
<213> ORGANISM: Homo sapiens

<400> SEQUENCE: 146

Ala Gln Leu Leu Gln Gly Leu Gly Phe Asn Leu Thr Glu Arg
1               5                   10

<210> SEQ ID NO 147
<211> LENGTH: 8
<212> TYPE: PRT
<213> ORGANISM: Homo sapiens

<400> SEQUENCE: 147

His Leu Val Ala Leu Ser Pro Lys
1               5

<210> SEQ ID NO 148
<211> LENGTH: 9
<212> TYPE: PRT
<213> ORGANISM: Homo sapiens

<400> SEQUENCE: 148

Thr Leu Asp Glu Ile Leu Gln Glu Lys
1               5

<210> SEQ ID NO 149
<211> LENGTH: 13
<212> TYPE: PRT
<213> ORGANISM: Homo sapiens

<400> SEQUENCE: 149

Thr Ser Asn Leu Leu Leu Ser His Ala Gly Ile Leu Lys
1               5                   10

<210> SEQ ID NO 150
<211> LENGTH: 11
<212> TYPE: PRT
<213> ORGANISM: Homo sapiens

<400> SEQUENCE: 150

Ala Leu Asp Phe Ala Val Gly Glu Tyr Asn Lys
1               5                   10

<210> SEQ ID NO 151
<211> LENGTH: 6
<212> TYPE: PRT
<213> ORGANISM: Homo sapiens

<400> SEQUENCE: 151

Ala Leu Gln Val Val Arg
1               5
```

<210> SEQ ID NO 152
<211> LENGTH: 12
<212> TYPE: PRT
<213> ORGANISM: Homo sapiens

<400> SEQUENCE: 152

Glu Leu Pro Ser Leu Gln His Pro Asn Glu Gln Lys
1               5                   10

<210> SEQ ID NO 153
<211> LENGTH: 13
<212> TYPE: PRT
<213> ORGANISM: Homo sapiens

<400> SEQUENCE: 153

Asn Val Ala Leu Val Ser Gly Asp Thr Glu Asn Ala Lys
1               5                   10

<210> SEQ ID NO 154
<211> LENGTH: 8
<212> TYPE: PRT
<213> ORGANISM: Homo sapiens

<400> SEQUENCE: 154

Leu Val Val Leu Pro Phe Pro Lys
1               5

<210> SEQ ID NO 155
<211> LENGTH: 8
<212> TYPE: PRT
<213> ORGANISM: Homo sapiens

<400> SEQUENCE: 155

Val Asn Asp Ala Gln Glu Tyr Arg
1               5

<210> SEQ ID NO 156
<211> LENGTH: 14
<212> TYPE: PRT
<213> ORGANISM: Homo sapiens

<400> SEQUENCE: 156

Ala His Tyr Gly Gly Phe Thr Val Gln Asn Glu Ala Asn Lys
1               5                   10

<210> SEQ ID NO 157
<211> LENGTH: 13
<212> TYPE: PRT
<213> ORGANISM: Homo sapiens

<400> SEQUENCE: 157

Gln Gly Phe Gly Asn Val Ala Thr Asn Thr Asp Gly Lys
1               5                   10

<210> SEQ ID NO 158
<211> LENGTH: 13
<212> TYPE: PRT
<213> ORGANISM: Homo sapiens

<400> SEQUENCE: 158

Tyr Glu Ala Ser Ile Leu Thr His Asp Ser Ser Ile Arg
1               5                   10

<210> SEQ ID NO 159
<211> LENGTH: 18

```
<212> TYPE: PRT
<213> ORGANISM: Homo sapiens

<400> SEQUENCE: 159

His Thr Ser Val Gln Thr Thr Ser Gly Ser Gly Pro Phe Thr Asp
1               5                   10                  15

Val Arg

<210> SEQ ID NO 160
<211> LENGTH: 19
<212> TYPE: PRT
<213> ORGANISM: Homo sapiens

<400> SEQUENCE: 160

Ser Ser Pro Val Val Ile Asp Ala Ser Thr Ala Ile Asp Ala Pro Ser
1               5                   10                  15

Asn Leu Arg

<210> SEQ ID NO 161
<211> LENGTH: 10
<212> TYPE: PRT
<213> ORGANISM: Homo sapiens

<400> SEQUENCE: 161

Gly Tyr His Leu Asn Glu Glu Gly Thr Arg
1               5                   10

<210> SEQ ID NO 162
<211> LENGTH: 17
<212> TYPE: PRT
<213> ORGANISM: Homo sapiens

<400> SEQUENCE: 162

Ser Gln Glu Thr Gly Asp Leu Asp Val Gly Gly Leu Gln Glu Thr Asp
1               5                   10                  15

Lys

<210> SEQ ID NO 163
<211> LENGTH: 10
<212> TYPE: PRT
<213> ORGANISM: Homo sapiens

<400> SEQUENCE: 163

Thr Gly Tyr Tyr Phe Asp Gly Ile Ser Arg
1               5                   10

<210> SEQ ID NO 164
<211> LENGTH: 8
<212> TYPE: PRT
<213> ORGANISM: Homo sapiens

<400> SEQUENCE: 164

Thr Gly Ala Gln Glu Leu Leu Arg
1               5

<210> SEQ ID NO 165
<211> LENGTH: 14
<212> TYPE: PRT
<213> ORGANISM: Homo sapiens

<400> SEQUENCE: 165

Pro Gly Gly Gly Phe Val Pro Asn Phe Gln Leu Phe Glu Lys
1               5                   10
```

<210> SEQ ID NO 166
<211> LENGTH: 9
<212> TYPE: PRT
<213> ORGANISM: Homo sapiens

<400> SEQUENCE: 166

Val Gly Tyr Val Ser Gly Trp Gly Arg
1               5

<210> SEQ ID NO 167
<211> LENGTH: 16
<212> TYPE: PRT
<213> ORGANISM: Homo sapiens

<400> SEQUENCE: 167

Thr Tyr Phe Pro His Phe Asp Leu Ser His Gly Ser Ala Gln Val Lys
1               5                   10                  15

<210> SEQ ID NO 168
<211> LENGTH: 15
<212> TYPE: PRT
<213> ORGANISM: Homo sapiens

<400> SEQUENCE: 168

Val Gly Ala His Ala Gly Glu Tyr Gly Ala Glu Ala Leu Glu Arg
1               5                   10                  15

<210> SEQ ID NO 169
<211> LENGTH: 15
<212> TYPE: PRT
<213> ORGANISM: Homo sapiens

<400> SEQUENCE: 169

Leu Tyr Leu Val Gln Gly Thr Gln Val Tyr Val Phe Leu Thr Lys
1               5                   10                  15

<210> SEQ ID NO 170
<211> LENGTH: 11
<212> TYPE: PRT
<213> ORGANISM: Homo sapiens

<400> SEQUENCE: 170

Asn Phe Pro Ser Pro Val Asp Ala Ala Phe Arg
1               5                   10

<210> SEQ ID NO 171
<211> LENGTH: 14
<212> TYPE: PRT
<213> ORGANISM: Homo sapiens

<400> SEQUENCE: 171

Gly Glu Thr His Glu Gln Val His Ser Ile Leu His Phe Lys
1               5                   10

<210> SEQ ID NO 172
<211> LENGTH: 9
<212> TYPE: PRT
<213> ORGANISM: Homo sapiens

<400> SEQUENCE: 172

Asn Tyr Asn Leu Val Glu Ser Leu Lys
1               5

```
<210> SEQ ID NO 173
<211> LENGTH: 9
<212> TYPE: PRT
<213> ORGANISM: Homo sapiens

<400> SEQUENCE: 173

Ser Val Asn Asp Leu Tyr Ile Gln Lys
1               5

<210> SEQ ID NO 174
<211> LENGTH: 10
<212> TYPE: PRT
<213> ORGANISM: Homo sapiens

<400> SEQUENCE: 174

Ser Pro Leu Asn Asp Phe Gln Val Leu Arg
1               5                   10

<210> SEQ ID NO 175
<211> LENGTH: 9
<212> TYPE: PRT
<213> ORGANISM: Homo sapiens

<400> SEQUENCE: 175

Asp Gly Tyr Leu Phe Gln Leu Leu Arg
1               5

<210> SEQ ID NO 176
<211> LENGTH: 8
<212> TYPE: PRT
<213> ORGANISM: Homo sapiens

<400> SEQUENCE: 176

Phe Leu Asn Val Leu Ser Pro Arg
1               5

<210> SEQ ID NO 177
<211> LENGTH: 11
<212> TYPE: PRT
<213> ORGANISM: Homo sapiens

<400> SEQUENCE: 177

Tyr Gly Gln Pro Leu Pro Gly Tyr Thr Thr Lys
1               5                   10

<210> SEQ ID NO 178
<211> LENGTH: 15
<212> TYPE: PRT
<213> ORGANISM: Homo sapiens

<400> SEQUENCE: 178

Asn Leu Ile Ala Ala Val Ala Pro Gly Ala Phe Leu Gly Leu Lys
1               5                   10                  15

<210> SEQ ID NO 179
<211> LENGTH: 16
<212> TYPE: PRT
<213> ORGANISM: Homo sapiens

<400> SEQUENCE: 179

Val Ala Gly Leu Leu Glu Asp Thr Phe Pro Gly Leu Leu Gly Leu Arg
1               5                   10                  15

<210> SEQ ID NO 180
<211> LENGTH: 15
```

```
<212> TYPE: PRT
<213> ORGANISM: Homo sapiens

<400> SEQUENCE: 180

Glu Thr Ala Val Asp Gly Glu Leu Val Val Leu Tyr Asp Val Lys
1               5                   10                  15

<210> SEQ ID NO 181
<211> LENGTH: 20
<212> TYPE: PRT
<213> ORGANISM: Homo sapiens

<400> SEQUENCE: 181

Phe Leu His Val Pro Asp Thr Phe Glu Gly His Phe Asp Gly Val Pro
1               5                   10                  15

Val Ile Ser Lys
            20

<210> SEQ ID NO 182
<211> LENGTH: 16
<212> TYPE: PRT
<213> ORGANISM: Homo sapiens

<400> SEQUENCE: 182

Ser Pro Glu Gln Gln Glu Thr Val Leu Asp Gly Asn Leu Ile Ile Arg
1               5                   10                  15

<210> SEQ ID NO 183
<211> LENGTH: 9
<212> TYPE: PRT
<213> ORGANISM: Homo sapiens

<400> SEQUENCE: 183

Ile Ser Thr Leu Ser Cys Glu Asn Lys
1               5

<210> SEQ ID NO 184
<211> LENGTH: 18
<212> TYPE: PRT
<213> ORGANISM: Homo sapiens

<400> SEQUENCE: 184

Ile Ile Thr Gly Leu Leu Glu Phe Glu Val Tyr Leu Glu Tyr Leu Gln
1               5                   10                  15

Asn Arg

<210> SEQ ID NO 185
<211> LENGTH: 12
<212> TYPE: PRT
<213> ORGANISM: Homo sapiens

<400> SEQUENCE: 185

Val Gly Ser Ala Leu Phe Leu Ser His Asn Leu Lys
1               5                   10

<210> SEQ ID NO 186
<211> LENGTH: 19
<212> TYPE: PRT
<213> ORGANISM: Homo sapiens

<400> SEQUENCE: 186

Asp Ile Pro Thr Asn Ser Pro Glu Leu Glu Glu Thr Leu Thr His Thr
1               5                   10                  15
```

Ile Thr Lys

<210> SEQ ID NO 187
<211> LENGTH: 11
<212> TYPE: PRT
<213> ORGANISM: Homo sapiens

<400> SEQUENCE: 187

Thr Val Gly Ser Asp Thr Phe Tyr Ser Phe Lys
1               5                   10

<210> SEQ ID NO 188
<211> LENGTH: 10
<212> TYPE: PRT
<213> ORGANISM: Homo sapiens

<400> SEQUENCE: 188

Asp Leu Leu His Val Leu Ala Phe Ser Lys
1               5                   10

<210> SEQ ID NO 189
<211> LENGTH: 10
<212> TYPE: PRT
<213> ORGANISM: Homo sapiens

<400> SEQUENCE: 189

Tyr Ser Glu Asn Ser Thr Thr Val Ile Arg
1               5                   10

<210> SEQ ID NO 190
<211> LENGTH: 19
<212> TYPE: PRT
<213> ORGANISM: Homo sapiens

<400> SEQUENCE: 190

Gly Leu Gln Tyr Ala Ala Gln Glu Gly Leu Leu Ala Leu Gln Ser Glu
1               5                   10                  15

Leu Leu Arg

<210> SEQ ID NO 191
<211> LENGTH: 11
<212> TYPE: PRT
<213> ORGANISM: Homo sapiens

<400> SEQUENCE: 191

Ile Thr Leu Pro Asp Phe Thr Gly Asp Leu Arg
1               5                   10

<210> SEQ ID NO 192
<211> LENGTH: 19
<212> TYPE: PRT
<213> ORGANISM: Homo sapiens

<400> SEQUENCE: 192

Leu Gly Ser Phe Glu Gly Leu Val Asn Leu Thr Phe Ile His Leu Gln
1               5                   10                  15

His Asn Arg

<210> SEQ ID NO 193
<211> LENGTH: 18
<212> TYPE: PRT
<213> ORGANISM: Homo sapiens

<400> SEQUENCE: 193

Leu Pro Ser Gly Leu Pro Val Ser Leu Leu Thr Leu Tyr Leu Asp Asn
1               5                   10                  15

Asn Lys

<210> SEQ ID NO 194
<211> LENGTH: 11
<212> TYPE: PRT
<213> ORGANISM: Homo sapiens

<400> SEQUENCE: 194

Ser Leu Glu Asp Leu Gln Leu Thr His Asn Lys
1               5                   10

<210> SEQ ID NO 195
<211> LENGTH: 14
<212> TYPE: PRT
<213> ORGANISM: Homo sapiens

<400> SEQUENCE: 195

Ser Leu Glu Tyr Leu Asp Leu Ser Phe Asn Gln Ile Ala Arg
1               5                   10

<210> SEQ ID NO 196
<211> LENGTH: 13
<212> TYPE: PRT
<213> ORGANISM: Homo sapiens

<400> SEQUENCE: 196

Phe Asn Ser Val Pro Leu Thr Asp Thr Gly His Glu Arg
1               5                   10

<210> SEQ ID NO 197
<211> LENGTH: 15
<212> TYPE: PRT
<213> ORGANISM: Homo sapiens

<400> SEQUENCE: 197

Ala Pro Gly Glu Leu Glu His Gly Leu Ile Thr Phe Ser Thr Arg
1               5                   10                  15

<210> SEQ ID NO 198
<211> LENGTH: 12
<212> TYPE: PRT
<213> ORGANISM: Homo sapiens

<400> SEQUENCE: 198

Thr Glu Gly Gln Phe Val Asp Leu Thr Gly Asn Arg
1               5                   10

<210> SEQ ID NO 199
<211> LENGTH: 15
<212> TYPE: PRT
<213> ORGANISM: Homo sapiens

<400> SEQUENCE: 199

Leu Gly Leu Gly Ala Asp Val Ala Gln Val Thr Gly Ala Leu Arg
1               5                   10                  15

<210> SEQ ID NO 200
<211> LENGTH: 11
<212> TYPE: PRT
<213> ORGANISM: Homo sapiens

<400> SEQUENCE: 200

```
Ser Leu Gly Pro Ala Leu Leu Leu Gln Lys
1               5                   10

<210> SEQ ID NO 201
<211> LENGTH: 15
<212> TYPE: PRT
<213> ORGANISM: Homo sapiens

<400> SEQUENCE: 201

Phe Val Gly Thr Pro Glu Val Asn Gln Thr Thr Leu Tyr Gln Arg
1               5                   10                  15

<210> SEQ ID NO 202
<211> LENGTH: 12
<212> TYPE: PRT
<213> ORGANISM: Homo sapiens

<400> SEQUENCE: 202

Gly Phe Gln Ala Leu Gly Asp Ala Ala Asp Ile Arg
1               5                   10

<210> SEQ ID NO 203
<211> LENGTH: 8
<212> TYPE: PRT
<213> ORGANISM: Homo sapiens

<400> SEQUENCE: 203

Glu Leu Thr Leu Glu Asp Leu Lys
1               5

<210> SEQ ID NO 204
<211> LENGTH: 10
<212> TYPE: PRT
<213> ORGANISM: Homo sapiens

<400> SEQUENCE: 204

Phe Pro Ala Ile Gln Asn Leu Ala Leu Arg
1               5                   10

<210> SEQ ID NO 205
<211> LENGTH: 18
<212> TYPE: PRT
<213> ORGANISM: Homo sapiens

<400> SEQUENCE: 205

Ser Thr Leu Ser Val Gly Val Ser Gly Thr Leu Val Leu Leu Gln Gly
1               5                   10                  15

Ala Arg

<210> SEQ ID NO 206
<211> LENGTH: 10
<212> TYPE: PRT
<213> ORGANISM: Homo sapiens

<400> SEQUENCE: 206

Ile Ala Asn Val Phe Thr Asn Ala Phe Arg
1               5                   10

<210> SEQ ID NO 207
<211> LENGTH: 12
<212> TYPE: PRT
<213> ORGANISM: Homo sapiens

<400> SEQUENCE: 207
```

Val Val Leu Glu Gly Gly Ile Asp Pro Ile Leu Arg
1               5                   10

<210> SEQ ID NO 208
<211> LENGTH: 15
<212> TYPE: PRT
<213> ORGANISM: Homo sapiens

<400> SEQUENCE: 208

Ala Ala Pro Ala Pro Ala Pro Pro Glu Pro Glu Arg Pro Lys
1               5                   10                  15

<210> SEQ ID NO 209
<211> LENGTH: 17
<212> TYPE: PRT
<213> ORGANISM: Homo sapiens

<400> SEQUENCE: 209

Pro Ser Leu Ser His Leu Leu Ser Gln Tyr Tyr Gly Ala Gly Val Ala
1               5                   10                  15
Arg

<210> SEQ ID NO 210
<211> LENGTH: 13
<212> TYPE: PRT
<213> ORGANISM: Homo sapiens

<400> SEQUENCE: 210

Thr Asp Cys Pro Gly Asp Ala Leu Phe Asp Leu Leu Arg
1               5                   10

<210> SEQ ID NO 211
<211> LENGTH: 16
<212> TYPE: PRT
<213> ORGANISM: Homo sapiens

<400> SEQUENCE: 211

Ala Leu Pro Ala Val Glu Thr Gln Ala Pro Thr Ser Leu Ala Thr Lys
1               5                   10                  15

<210> SEQ ID NO 212
<211> LENGTH: 10
<212> TYPE: PRT
<213> ORGANISM: Homo sapiens

<400> SEQUENCE: 212

Ala Thr Ala Val Val Asp Gly Ala Phe Lys
1               5                   10

<210> SEQ ID NO 213
<211> LENGTH: 8
<212> TYPE: PRT
<213> ORGANISM: Homo sapiens

<400> SEQUENCE: 213

Gly Leu Phe Ile Ile Asp Gly Lys
1               5

<210> SEQ ID NO 214
<211> LENGTH: 14
<212> TYPE: PRT
<213> ORGANISM: Homo sapiens

<400> SEQUENCE: 214

Ser Ser Gly Leu Val Ser Asn Ala Pro Gly Val Gln Ile Arg
1               5                   10

<210> SEQ ID NO 215
<211> LENGTH: 11
<212> TYPE: PRT
<213> ORGANISM: Homo sapiens

<400> SEQUENCE: 215

Ala Val Glu Pro Gln Leu Gln Glu Glu Glu Arg
1               5                   10

<210> SEQ ID NO 216
<211> LENGTH: 15
<212> TYPE: PRT
<213> ORGANISM: Homo sapiens

<400> SEQUENCE: 216

Phe Leu Glu Gln Glu Leu Glu Thr Ile Thr Ile Pro Asp Leu Arg
1               5                   10                  15

<210> SEQ ID NO 217
<211> LENGTH: 12
<212> TYPE: PRT
<213> ORGANISM: Homo sapiens

<400> SEQUENCE: 217

Thr Ser Leu Glu Asp Phe Tyr Leu Asp Glu Glu Arg
1               5                   10

<210> SEQ ID NO 218
<211> LENGTH: 10
<212> TYPE: PRT
<213> ORGANISM: Homo sapiens

<400> SEQUENCE: 218

Thr Val Gln Ala Val Leu Thr Val Pro Lys
1               5                   10

<210> SEQ ID NO 219
<211> LENGTH: 12
<212> TYPE: PRT
<213> ORGANISM: Homo sapiens

<400> SEQUENCE: 219

Val Ser Glu Gly Asn His Asp Ile Ala Leu Ile Lys
1               5                   10

<210> SEQ ID NO 220
<211> LENGTH: 10
<212> TYPE: PRT
<213> ORGANISM: Homo sapiens

<400> SEQUENCE: 220

Leu Leu Asp Ser Leu Pro Ser Asp Thr Arg
1               5                   10

<210> SEQ ID NO 221
<211> LENGTH: 11
<212> TYPE: PRT
<213> ORGANISM: Homo sapiens

<400> SEQUENCE: 221

Ala Val Val Glu Val Asp Glu Ser Gly Thr Arg

-continued

<210> SEQ ID NO 222
<211> LENGTH: 11
<212> TYPE: PRT
<213> ORGANISM: Homo sapiens

<400> SEQUENCE: 222

Phe Ser Ile Glu Gly Ser Tyr Gln Leu Glu Lys
1               5                   10

<210> SEQ ID NO 223
<211> LENGTH: 22
<212> TYPE: PRT
<213> ORGANISM: Homo sapiens

<400> SEQUENCE: 223

Val Ile Leu Gly Ala His Gln Glu Val Asn Leu Glu Pro His Val Gln
1               5                   10                  15

Glu Ile Glu Val Ser Arg
            20

<210> SEQ ID NO 224
<211> LENGTH: 13
<212> TYPE: PRT
<213> ORGANISM: Homo sapiens

<400> SEQUENCE: 224

Asp Glu Ile Ser Thr Thr Asp Ala Ile Phe Val Gln Arg
1               5                   10

<210> SEQ ID NO 225
<211> LENGTH: 10
<212> TYPE: PRT
<213> ORGANISM: Homo sapiens

<400> SEQUENCE: 225

Phe Ser Leu Glu Thr Glu Val Asp Leu Arg
1               5                   10

<210> SEQ ID NO 226
<211> LENGTH: 12
<212> TYPE: PRT
<213> ORGANISM: Homo sapiens

<400> SEQUENCE: 226

Ala Phe Ile Gln Leu Trp Ala Phe Asp Ala Val Lys
1               5                   10

<210> SEQ ID NO 227
<211> LENGTH: 8
<212> TYPE: PRT
<213> ORGANISM: Homo sapiens

<400> SEQUENCE: 227

Glu Thr Leu Leu Gln Asp Phe Arg
1               5

<210> SEQ ID NO 228
<211> LENGTH: 9
<212> TYPE: PRT
<213> ORGANISM: Homo sapiens

<400> SEQUENCE: 228

```
His His Gly Pro Thr Ile Thr Ala Lys
1               5

<210> SEQ ID NO 229
<211> LENGTH: 11
<212> TYPE: PRT
<213> ORGANISM: Homo sapiens

<400> SEQUENCE: 229

Glu Thr Ser Asn Phe Gly Phe Ser Leu Leu Arg
1               5                   10

<210> SEQ ID NO 230
<211> LENGTH: 10
<212> TYPE: PRT
<213> ORGANISM: Homo sapiens

<400> SEQUENCE: 230

Leu Phe Asp Glu Ile Asn Pro Glu Thr Lys
1               5                   10

<210> SEQ ID NO 231
<211> LENGTH: 11
<212> TYPE: PRT
<213> ORGANISM: Homo sapiens

<400> SEQUENCE: 231

Asp Gln Tyr Tyr Asn Ile Asp Val Pro Ser Arg
1               5                   10

<210> SEQ ID NO 232
<211> LENGTH: 17
<212> TYPE: PRT
<213> ORGANISM: Homo sapiens

<400> SEQUENCE: 232

Gly Phe Gly Gly Leu Thr Gly Gln Ile Val Ala Ala Leu Ser Thr Ala
1               5                   10                  15

Lys

<210> SEQ ID NO 233
<211> LENGTH: 10
<212> TYPE: PRT
<213> ORGANISM: Homo sapiens

<400> SEQUENCE: 233

Glu Leu Leu Glu Ser Tyr Ile Asp Gly Arg
1               5                   10

<210> SEQ ID NO 234
<211> LENGTH: 12
<212> TYPE: PRT
<213> ORGANISM: Homo sapiens

<400> SEQUENCE: 234

Glu Thr Ala Ala Ser Leu Leu Gln Ala Gly Tyr Lys
1               5                   10

<210> SEQ ID NO 235
<211> LENGTH: 10
<212> TYPE: PRT
<213> ORGANISM: Homo sapiens

<400> SEQUENCE: 235
```

Tyr Trp Gly Val Ala Ser Phe Leu Gln Lys
1               5                   10

<210> SEQ ID NO 236
<211> LENGTH: 8
<212> TYPE: PRT
<213> ORGANISM: Homo sapiens

<400> SEQUENCE: 236

Ala Glu Phe Ala Glu Val Ser Lys
1               5

<210> SEQ ID NO 237
<211> LENGTH: 10
<212> TYPE: PRT
<213> ORGANISM: Homo sapiens

<400> SEQUENCE: 237

Leu Val Asn Glu Val Thr Glu Phe Ala Lys
1               5                   10

<210> SEQ ID NO 238
<211> LENGTH: 8
<212> TYPE: PRT
<213> ORGANISM: Homo sapiens

<400> SEQUENCE: 238

Phe Arg Pro Asp Gly Leu Pro Lys
1               5

<210> SEQ ID NO 239
<211> LENGTH: 9
<212> TYPE: PRT
<213> ORGANISM: Homo sapiens

<400> SEQUENCE: 239

Gly Pro Gly Gly Val Trp Ala Ala Lys
1               5

<210> SEQ ID NO 240
<211> LENGTH: 12
<212> TYPE: PRT
<213> ORGANISM: Homo sapiens

<400> SEQUENCE: 240

Ala Tyr Ser Leu Phe Ser Tyr Asn Thr Gln Gly Arg
1               5                   10

<210> SEQ ID NO 241
<211> LENGTH: 10
<212> TYPE: PRT
<213> ORGANISM: Homo sapiens

<400> SEQUENCE: 241

Ile Gln Asn Ile Leu Thr Glu Glu Pro Lys
1               5                   10

<210> SEQ ID NO 242
<211> LENGTH: 9
<212> TYPE: PRT
<213> ORGANISM: Homo sapiens

<400> SEQUENCE: 242

Ser Phe Asn Pro Asn Ser Pro Gly Lys
1               5

<210> SEQ ID NO 243
<211> LENGTH: 14
<212> TYPE: PRT
<213> ORGANISM: Homo sapiens

<400> SEQUENCE: 243

Ile Ala Leu Gly Gly Leu Leu Phe Pro Ala Ser Asn Leu Arg
1               5                   10

<210> SEQ ID NO 244
<211> LENGTH: 8
<212> TYPE: PRT
<213> ORGANISM: Homo sapiens

<400> SEQUENCE: 244

Val Val Leu Ser Gln Gly Ser Lys
1               5

<210> SEQ ID NO 245
<211> LENGTH: 21
<212> TYPE: PRT
<213> ORGANISM: Homo sapiens

<400> SEQUENCE: 245

Gly Gly Thr Leu Gly Thr Pro Gln Thr Gly Ser Glu Asn Asp Ala Leu
1               5                   10                  15

Tyr Glu Tyr Leu Arg
            20

<210> SEQ ID NO 246
<211> LENGTH: 8
<212> TYPE: PRT
<213> ORGANISM: Homo sapiens

<400> SEQUENCE: 246

Ala Val Leu His Ile Gly Glu Lys
1               5

<210> SEQ ID NO 247
<211> LENGTH: 15
<212> TYPE: PRT
<213> ORGANISM: Homo sapiens

<400> SEQUENCE: 247

Phe Ser Ile Ser Ala Thr Tyr Asp Leu Gly Ala Thr Leu Leu Lys
1               5                   10                  15

<210> SEQ ID NO 248
<211> LENGTH: 19
<212> TYPE: PRT
<213> ORGANISM: Homo sapiens

<400> SEQUENCE: 248

Thr Leu Tyr Glu Thr Glu Val Phe Ser Thr Asp Phe Ser Asn Ile Ser
1               5                   10                  15

Ala Ala Lys

<210> SEQ ID NO 249
<211> LENGTH: 20
<212> TYPE: PRT
<213> ORGANISM: Homo sapiens

<400> SEQUENCE: 249

Ile Pro Val Val Leu Pro Glu Asp Glu Gly Ile Tyr Thr Ala Phe Ala
1               5                   10                  15

Ser Asn Ile Lys
            20

<210> SEQ ID NO 250
<211> LENGTH: 19
<212> TYPE: PRT
<213> ORGANISM: Homo sapiens

<400> SEQUENCE: 250

Val Ala Gly Glu Ser Ala Glu Pro Glu Pro Glu Pro Glu Ala Asp Tyr
1               5                   10                  15

Tyr Ala Lys

<210> SEQ ID NO 251
<211> LENGTH: 10
<212> TYPE: PRT
<213> ORGANISM: Homo sapiens

<400> SEQUENCE: 251

Val Glu Gln His Val Glu Leu Tyr Gln Lys
1               5                   10

<210> SEQ ID NO 252
<211> LENGTH: 13
<212> TYPE: PRT
<213> ORGANISM: Homo sapiens

<400> SEQUENCE: 252

Ala Ala Asp Asp Thr Trp Glu Pro Phe Ala Ser Gly Lys
1               5                   10

<210> SEQ ID NO 253
<211> LENGTH: 13
<212> TYPE: PRT
<213> ORGANISM: Homo sapiens

<400> SEQUENCE: 253

Gly Ser Pro Ala Ile Asn Val Ala Val His Val Phe Arg
1               5                   10

<210> SEQ ID NO 254
<211> LENGTH: 13
<212> TYPE: PRT
<213> ORGANISM: Homo sapiens

<400> SEQUENCE: 254

Leu His Ile Asp Glu Met Asp Ser Val Pro Thr Val Arg
1               5                   10

<210> SEQ ID NO 255
<211> LENGTH: 16
<212> TYPE: PRT
<213> ORGANISM: Homo sapiens

<400> SEQUENCE: 255

Leu Ala Gly Leu Gly Leu Gln Gln Leu Asp Glu Gly Leu Phe Ser Arg
1               5                   10                  15

<210> SEQ ID NO 256
<211> LENGTH: 15
<212> TYPE: PRT

-continued

<213> ORGANISM: Homo sapiens

<400> SEQUENCE: 256

Ser Leu Thr Leu Gly Ile Glu Pro Val Ser Pro Thr Ser Leu Arg
1               5                   10                  15

<210> SEQ ID NO 257
<211> LENGTH: 10
<212> TYPE: PRT
<213> ORGANISM: Homo sapiens

<400> SEQUENCE: 257

Tyr Leu Gln Gly Ser Ser Val Gln Leu Arg
1               5                   10

<210> SEQ ID NO 258
<211> LENGTH: 8
<212> TYPE: PRT
<213> ORGANISM: Homo sapiens

<400> SEQUENCE: 258

Glu Leu Pro Glu His Thr Val Lys
1               5

<210> SEQ ID NO 259
<211> LENGTH: 10
<212> TYPE: PRT
<213> ORGANISM: Homo sapiens

<400> SEQUENCE: 259

Thr His Leu Pro Glu Val Phe Leu Ser Lys
1               5                   10

<210> SEQ ID NO 260
<211> LENGTH: 7
<212> TYPE: PRT
<213> ORGANISM: Homo sapiens

<400> SEQUENCE: 260

Leu Gly Glu Tyr Asp Leu Arg
1               5

<210> SEQ ID NO 261
<211> LENGTH: 8
<212> TYPE: PRT
<213> ORGANISM: Homo sapiens

<400> SEQUENCE: 261

Thr Phe Val Leu Asn Phe Ile Lys
1               5

<210> SEQ ID NO 262
<211> LENGTH: 10
<212> TYPE: PRT
<213> ORGANISM: Homo sapiens

<400> SEQUENCE: 262

Tyr Leu Asp Trp Ile His Gly His Ile Arg
1               5                   10

<210> SEQ ID NO 263
<211> LENGTH: 11
<212> TYPE: PRT
<213> ORGANISM: Homo sapiens -continued

```
<400> SEQUENCE: 263

Ser Phe Gln Thr Gly Leu Phe Thr Ala Ala Arg
1               5                   10

<210> SEQ ID NO 264
<211> LENGTH: 8
<212> TYPE: PRT
<213> ORGANISM: Homo sapiens

<400> SEQUENCE: 264

Val Tyr Phe Ala Gly Phe Pro Arg
1               5

<210> SEQ ID NO 265
<211> LENGTH: 10
<212> TYPE: PRT
<213> ORGANISM: Homo sapiens

<400> SEQUENCE: 265

Asp Phe Ala Glu His Leu Leu Ile Pro Arg
1               5                   10

<210> SEQ ID NO 266
<211> LENGTH: 9
<212> TYPE: PRT
<213> ORGANISM: Homo sapiens

<400> SEQUENCE: 266

Glu Asn Phe Val Leu Thr Thr Ala Lys
1               5

<210> SEQ ID NO 267
<211> LENGTH: 15
<212> TYPE: PRT
<213> ORGANISM: Homo sapiens

<400> SEQUENCE: 267

Asp Val Trp Gly Ile Glu Gly Pro Ile Asp Ala Ala Phe Thr Arg
1               5                   10                  15

<210> SEQ ID NO 268
<211> LENGTH: 12
<212> TYPE: PRT
<213> ORGANISM: Homo sapiens

<400> SEQUENCE: 268

Phe Glu Asp Gly Val Leu Asp Pro Asp Tyr Pro Arg
1               5                   10

<210> SEQ ID NO 269
<211> LENGTH: 18
<212> TYPE: PRT
<213> ORGANISM: Homo sapiens

<400> SEQUENCE: 269

Ile Gly Trp Pro Asn Ala Pro Ile Leu Ile Gln Asp Phe Glu Thr Leu
1               5                   10                  15

Pro Arg

<210> SEQ ID NO 270
<211> LENGTH: 13
<212> TYPE: PRT
<213> ORGANISM: Homo sapiens
```

-continued

<400> SEQUENCE: 270

Ile Leu Ala Gly Pro Ala Gly Asp Ser Asn Val Val Lys
1               5                   10

<210> SEQ ID NO 271
<211> LENGTH: 10
<212> TYPE: PRT
<213> ORGANISM: Homo sapiens

<400> SEQUENCE: 271

Ala Gly Glu Val Gln Glu Pro Glu Leu Arg
1               5                   10

<210> SEQ ID NO 272
<211> LENGTH: 12
<212> TYPE: PRT
<213> ORGANISM: Homo sapiens

<400> SEQUENCE: 272

Tyr Ser Leu Thr Tyr Ile Tyr Thr Gly Leu Ser Lys
1               5                   10

<210> SEQ ID NO 273
<211> LENGTH: 224
<212> TYPE: PRT
<213> ORGANISM: Homo sapiens

<400> SEQUENCE: 273

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
                20                  25                  30

Ser Asp Thr Ser Tyr Val Ser Leu Lys Ala Pro Leu Thr Lys Pro Leu
            35                  40                  45

Lys Ala Phe Thr Val Cys Leu His Phe Tyr Thr Glu Leu Ser Ser Thr
        50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
210                 215                 220

<210> SEQ ID NO 274

```
<211> LENGTH: 76
<212> TYPE: PRT
<213> ORGANISM: Homo sapiens

<400> SEQUENCE: 274

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Thr Pro
        35                  40                  45

Gly Val Trp Lys Ser Arg Glu Val Ala Thr Gly Ile Arg Gly His
    50                  55                  60

Arg Lys Met Val Leu Tyr Thr Leu Arg Ala Pro Arg
65                  70                  75

<210> SEQ ID NO 275
<211> LENGTH: 396
<212> TYPE: PRT
<213> ORGANISM: Homo sapiens

<400> SEQUENCE: 275

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270
```

```
Asp Val Arg Gly Asn Leu Arg Gly Asn Thr Glu Gly Leu Gln Lys Ser
    275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Gln Gln Gln
    370                 375                 380

Gln Glu Gln Val Gln Met Leu Ala Pro Leu Glu Ser
385                 390                 395

<210> SEQ ID NO 276
<211> LENGTH: 2386
<212> TYPE: PRT
<213> ORGANISM: Homo sapiens

<400> SEQUENCE: 276

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
```

-continued

```
                245                 250                 255
Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
            325                 330                 335

Gly Asn Gly Val Ser Cys Gln Glu Thr Ala Val Thr Gln Thr Tyr Gly
        340                 345                 350

Gly Asn Ser Asn Gly Glu Pro Cys Val Leu Pro Phe Thr Tyr Asn Gly
    355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
        420                 425                 430

Asp Cys Thr Ser Glu Gly Arg Arg Asp Asn Met Lys Trp Cys Gly Thr
    435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
            485                 490                 495

Thr Cys Val Gly Asn Gly Arg Gly Glu Trp Thr Cys Ile Ala Tyr Ser
        500                 505                 510

Gln Leu Arg Asp Gln Cys Ile Val Asp Asp Ile Thr Tyr Asn Val Asn
    515                 520                 525

Asp Thr Phe His Lys Arg His Glu Glu Gly His Met Leu Asn Cys Thr
530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
        580                 585                 590

Gly Ile Gly Glu Trp His Cys Gln Pro Leu Gln Thr Tyr Pro Ser Ser
    595                 600                 605

Ser Gly Pro Val Glu Val Phe Ile Thr Glu Thr Pro Ser Gln Pro Asn
610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys
        660                 665                 670
```

-continued

```
Pro Gly Val Val Tyr Glu Gly Gln Leu Ile Ser Ile Gln Gln Tyr Gly
        675                 680                 685

His Gln Glu Val Thr Arg Phe Asp Phe Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Gly Asp Glu Pro Gln Tyr Leu Asp Leu
                755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Arg Trp Ser
                820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro  Thr Asn Leu Gln Phe  Val Asn Glu
                995                1000                1005

Thr Asp  Ser Thr Val Leu Val  Arg Trp Thr Pro Pro  Arg Ala Gln
    1010                1015                1020

Ile Thr  Gly Tyr Arg Leu Thr  Val Gly Leu Thr Arg  Arg Gly Gln
    1025                1030                1035

Pro Arg  Gln Tyr Asn Val Gly  Pro Ser Val Ser Lys  Tyr Pro Leu
    1040                1045                1050

Arg Asn  Leu Gln Pro Ala Ser  Glu Tyr Thr Val Ser  Leu Val Ala
        1055                1060                1065

Ile Lys  Gly Asn Gln Glu Ser  Pro Lys Ala Thr Gly  Val Phe Thr
    1070                1075                1080
```

```
Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
1100                1105                1110

Gly Phe Lys Leu Gly Val Arg Pro Ser Gln Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Pro Thr Asp Leu Arg Phe Thr Asn Ile
    1265                1270                1275

Gly Pro Asp Thr Met Arg Val Thr Trp Ala Pro Pro Pro Ser Ile
    1280                1285                1290

Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
```

-continued

```
            1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635

Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
    1685                1690                1695

Thr Val Ser Val Val Ala Leu His Asp Asp Met Glu Ser Gln Pro
    1700                1705                1710

Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr
    1730                1735                1740

Pro Pro Asn Val Gln Leu Thr Gly Tyr Arg Val Arg Val Thr Pro
    1745                1750                1755

Lys Glu Lys Thr Gly Pro Met Lys Glu Ile Asn Leu Ala Pro Asp
    1760                1765                1770

Ser Ser Ser Val Val Val Ser Gly Leu Met Val Ala Thr Lys Tyr
    1775                1780                1785

Glu Val Ser Val Tyr Ala Leu Lys Asp Thr Leu Thr Ser Arg Pro
    1790                1795                1800

Ala Gln Gly Val Val Thr Thr Leu Glu Asn Val Ser Pro Pro Arg
    1805                1810                1815

Arg Ala Arg Val Thr Asp Ala Thr Glu Thr Thr Ile Thr Ile Ser
    1820                1825                1830

Trp Arg Thr Lys Thr Glu Thr Ile Thr Gly Phe Gln Val Asp Ala
    1835                1840                1845

Val Pro Ala Asn Gly Gln Thr Pro Ile Gln Arg Thr Ile Lys Pro
    1850                1855                1860

Asp Val Arg Ser Tyr Thr Ile Thr Gly Leu Gln Pro Gly Thr Asp
    1865                1870                1875
```

```
Tyr Lys Ile Tyr Leu Tyr Thr Leu Asn Asp Asn Ala Arg Ser Ser
1880            1885            1890

Pro Val Val Ile Asp Ala Ser Thr Ala Ile Asp Ala Pro Ser Asn
1895            1900            1905

Leu Arg Phe Leu Ala Thr Thr Pro Asn Ser Leu Leu Val Ser Trp
1910            1915            1920

Gln Pro Pro Arg Ala Arg Ile Thr Gly Tyr Ile Ile Lys Tyr Glu
1925            1930            1935

Lys Pro Gly Ser Pro Pro Arg Glu Val Val Pro Arg Pro Arg Pro
1940            1945            1950

Gly Val Thr Glu Ala Thr Ile Thr Gly Leu Glu Pro Gly Thr Glu
1955            1960            1965

Tyr Thr Ile Tyr Val Ile Ala Leu Lys Asn Asn Gln Lys Ser Glu
1970            1975            1980

Pro Leu Ile Gly Arg Lys Lys Thr Asp Glu Leu Pro Gln Leu Val
1985            1990            1995

Thr Leu Pro His Pro Asn Leu His Gly Pro Glu Ile Leu Asp Val
2000            2005            2010

Pro Ser Thr Val Gln Lys Thr Pro Phe Val Thr His Pro Gly Tyr
2015            2020            2025

Asp Thr Gly Asn Gly Ile Gln Leu Pro Gly Thr Ser Gly Gln Gln
2030            2035            2040

Pro Ser Val Gly Gln Gln Met Ile Phe Glu Glu His Gly Phe Arg
2045            2050            2055

Arg Thr Thr Pro Pro Thr Thr Ala Thr Pro Ile Arg His Arg Pro
2060            2065            2070

Arg Pro Tyr Pro Pro Asn Val Gly Glu Glu Ile Gln Ile Gly His
2075            2080            2085

Ile Pro Arg Glu Asp Val Asp Tyr His Leu Tyr Pro His Gly Pro
2090            2095            2100

Gly Leu Asn Pro Asn Ala Ser Thr Gly Gln Glu Ala Leu Ser Gln
2105            2110            2115

Thr Thr Ile Ser Trp Ala Pro Phe Gln Asp Thr Ser Glu Tyr Ile
2120            2125            2130

Ile Ser Cys His Pro Val Gly Thr Asp Glu Glu Pro Leu Gln Phe
2135            2140            2145

Arg Val Pro Gly Thr Ser Thr Ser Ala Thr Leu Thr Gly Leu Thr
2150            2155            2160

Arg Gly Ala Thr Tyr Asn Val Ile Val Glu Ala Leu Lys Asp Gln
2165            2170            2175

Gln Arg His Lys Val Arg Glu Glu Val Val Thr Val Gly Asn Ser
2180            2185            2190

Val Asn Glu Gly Leu Asn Gln Pro Thr Asp Asp Ser Cys Phe Asp
2195            2200            2205

Pro Tyr Thr Val Ser His Tyr Ala Val Gly Asp Glu Trp Glu Arg
2210            2215            2220

Met Ser Glu Ser Gly Phe Lys Leu Leu Cys Gln Cys Leu Gly Phe
2225            2230            2235

Gly Ser Gly His Phe Arg Cys Asp Ser Ser Arg Trp Cys His Asp
2240            2245            2250

Asn Gly Val Asn Tyr Lys Ile Gly Glu Lys Trp Asp Arg Gln Gly
2255            2260            2265
```

```
Glu Asn Gly Gln Met Met Ser Cys Thr Cys Leu Gly Asn Gly Lys
2270                2275                2280

Gly Glu Phe Lys Cys Asp Pro His Glu Ala Thr Cys Tyr Asp Asp
2285                2290                2295

Gly Lys Thr Tyr His Val Gly Glu Gln Trp Gln Lys Glu Tyr Leu
2300                2305                2310

Gly Ala Ile Cys Ser Cys Thr Cys Phe Gly Gly Gln Arg Gly Trp
2315                2320                2325

Arg Cys Asp Asn Cys Arg Arg Pro Gly Gly Glu Pro Ser Pro Glu
2330                2335                2340

Gly Thr Thr Gly Gln Ser Tyr Asn Gln Tyr Ser Gln Arg Tyr His
2345                2350                2355

Gln Arg Thr Asn Thr Asn Val Asn Cys Pro Ile Glu Cys Phe Met
2360                2365                2370

Pro Leu Asp Val Gln Ala Asp Arg Glu Asp Ser Arg Glu
2375                2380                2385

<210> SEQ ID NO 277
<211> LENGTH: 481
<212> TYPE: PRT
<213> ORGANISM: Homo sapiens

<400> SEQUENCE: 277

Met Gly Ala Leu Ala Arg Ala Leu Pro Ser Ile Leu Leu Ala Leu Leu
1               5                   10                  15

Leu Thr Ser Thr Pro Glu Ala Leu Gly Ala Asn Pro Gly Leu Val Ala
            20                  25                  30

Arg Ile Thr Asp Lys Gly Leu Gln Tyr Ala Gln Glu Gly Leu Leu
        35                  40                  45

Ala Leu Gln Ser Glu Leu Leu Arg Ile Thr Leu Pro Asp Phe Thr Gly
    50                  55                  60

Asp Leu Arg Ile Pro His Val Gly Arg Gly Arg Tyr Glu Phe His Ser
65                  70                  75                  80

Leu Asn Ile His Ser Cys Glu Leu Leu His Ser Ala Leu Arg Pro Val
                85                  90                  95

Pro Gly Gln Gly Leu Ser Leu Ser Ile Ser Asp Ser Ser Ile Arg Val
            100                 105                 110

Gln Gly Arg Trp Lys Val Arg Lys Ser Phe Phe Lys Leu Gln Gly Ser
        115                 120                 125

Phe Asp Val Ser Val Lys Gly Ile Ser Ile Ser Val Asn Leu Leu Leu
130                 135                 140

Gly Ser Glu Ser Ser Gly Arg Pro Thr Val Thr Ala Ser Ser Cys Ser
145                 150                 155                 160

Ser Asp Ile Ala Asp Val Glu Val Asp Met Ser Gly Asp Leu Gly Trp
                165                 170                 175

Leu Leu Asn Leu Phe His Asn Gln Ile Glu Ser Lys Phe Gln Lys Val
            180                 185                 190

Leu Glu Ser Arg Ile Cys Glu Met Ile Gln Lys Ser Val Ser Ser Asp
        195                 200                 205

Leu Gln Pro Tyr Leu Gln Thr Leu Pro Val Thr Thr Glu Ile Asp Ser
    210                 215                 220

Phe Ala Asp Ile Asp Tyr Ser Leu Val Glu Ala Pro Arg Ala Thr Ala
225                 230                 235                 240

Gln Met Leu Glu Val Met Phe Lys Gly Glu Ile Phe His Arg Asn His
                245                 250                 255
```

-continued

```
Arg Ser Pro Val Thr Leu Leu Ala Ala Val Met Ser Leu Pro Glu Glu
            260                 265                 270

His Asn Lys Met Val Tyr Phe Ala Ile Ser Asp Tyr Val Phe Asn Thr
        275                 280                 285

Ala Ser Leu Val Tyr His Glu Glu Gly Tyr Leu Asn Phe Ser Ile Thr
    290                 295                 300

Asp Asp Met Ile Pro Pro Asp Ser Asn Ile Arg Leu Thr Thr Lys Ser
305                 310                 315                 320

Phe Arg Pro Phe Val Pro Arg Leu Ala Arg Leu Tyr Pro Asn Met Asn
                325                 330                 335

Leu Glu Leu Gln Gly Ser Val Pro Ser Ala Pro Leu Leu Asn Phe Ser
            340                 345                 350

Pro Gly Asn Leu Ser Val Asp Pro Tyr Met Glu Ile Asp Ala Phe Val
        355                 360                 365

Leu Leu Pro Ser Ser Ser Lys Glu Pro Val Phe Arg Leu Ser Val Ala
    370                 375                 380

Thr Asn Val Ser Ala Thr Leu Thr Phe Asn Thr Ser Lys Ile Thr Gly
385                 390                 395                 400

Phe Leu Lys Pro Gly Lys Val Lys Val Glu Leu Lys Glu Ser Lys Val
                405                 410                 415

Gly Leu Phe Asn Ala Glu Leu Leu Glu Ala Leu Leu Asn Tyr Tyr Ile
            420                 425                 430

Leu Asn Thr Phe Tyr Pro Lys Phe Asn Asp Lys Leu Ala Glu Gly Phe
        435                 440                 445

Pro Leu Pro Leu Leu Lys Arg Val Gln Leu Tyr Asp Leu Gly Leu Gln
    450                 455                 460

Ile His Lys Asp Phe Leu Phe Leu Gly Ala Asn Val Gln Tyr Met Arg
465                 470                 475                 480

Val
```